(12) United States Patent
Maher et al.

(10) Patent No.: US 12,357,293 B2
(45) Date of Patent: Jul. 15, 2025

(54) METHOD OF FACILITATING ACCESS TO A NEONATE THROUGH A CAESAREAN INCISION IN THE WOMAN'S ABDOMEN BY OPENING THE INCISION

(71) Applicant: University of Galway, Galway (IE)

(72) Inventors: Marie-Therese Maher, Gort (IE); Padraig Maher, Moycullen (IE); Barry McCann, Gort (IE)

(73) Assignee: NUA SURGICAL LIMITED, Galway (IE)

( * ) Notice: Subject to any disclaimer, the term of this patent is extended or adjusted under 35 U.S.C. 154(b) by 897 days.

(21) Appl. No.: 17/531,237

(22) Filed: Nov. 19, 2021

(65) Prior Publication Data

US 2022/0257230 A1 Aug. 18, 2022

Related U.S. Application Data

(63) Continuation of application No. 17/086,054, filed on Oct. 30, 2020, now Pat. No. 11,259,791.

(30) Foreign Application Priority Data

Oct. 30, 2019 (EP) ..................................... 19206358

(51) Int. Cl.
*A61B 17/02* (2006.01)
*A61B 17/42* (2006.01)

(52) U.S. Cl.
CPC ...... *A61B 17/0293* (2013.01); *A61B 17/0281* (2013.01); *A61B 17/42* (2013.01)

(58) Field of Classification Search
CPC . A61B 17/0281; A61B 17/0293; A61B 17/42; A61B 2017/0287

(Continued)

(56) References Cited

U.S. PATENT DOCUMENTS 2,473,266 A 6/1949 Wexler
4,421,107 A 12/1983 Estes et al.
(Continued)

FOREIGN PATENT DOCUMENTS

WO WO 2011/158046 A1 12/2011
WO WO 2018/119473 A1 6/2018

OTHER PUBLICATIONS

Extended European Search Report issued on May 11, 2020 in counterpart European Patent Application No. 19206358.4 (9 pages, in English).

*Primary Examiner* — Eduardo C Robert
*Assistant Examiner* — Christina Negrellirodriguez
(74) *Attorney, Agent, or Firm* — Brown Rudnick LLP; Adam M. Schoen

(57) ABSTRACT

A method of facilitating access to a neonate through a caesarean incision in the woman's abdomen by opening the incision, includes providing a supporting ring dimensioned to allow delivery of a neonate through the ring and comprising a non-adjustable pelvic-region retractor and handle fixed to the supporting ring and articulating the supporting ring to insert the non-adjustable pelvic-region retractor into the incision to cover and hold back the woman's bladder with the supporting ring disposed over the woman's abdomen. A first adjustable saddle-shaped retractor is then inserted into the incision to cup a first section of abdominal tissue on an abdominal side of the incision, before attaching the first adjustable saddle-shaped retractor to the supporting ring while it is cupping the first section of abdominal tissue at a first position spaced apart from the non-adjustable pelvic-region retractor to anchor the supporting ring to the woman and partially open the incision.

20 Claims, 64 Drawing Sheets

(58) Field of Classification Search
USPC .................................... 600/206, 233, 208
See application file for complete search history.

(56) References Cited

U.S. PATENT DOCUMENTS

| | | | |
|---|---|---|---|
| 5,967,973 A * | 10/1999 | Sherts | A61M 1/77 600/233 |
| 6,464,634 B1 * | 10/2002 | Fraser | A61B 17/0293 600/233 |
| 6,582,364 B2 | 6/2003 | Butler et al. | |
| 2004/0260153 A1 | 12/2004 | Pulford et al. | |
| 2007/0161866 A1 | 7/2007 | Fowler, Jr. et al. | |
| 2011/0021879 A1 | 1/2011 | Hart et al. | |
| 2019/0254651 A1 * | 8/2019 | Coale | A61M 29/00 |
| 2021/0128135 A1 * | 5/2021 | Maher | A61B 17/42 |

* cited by examiner

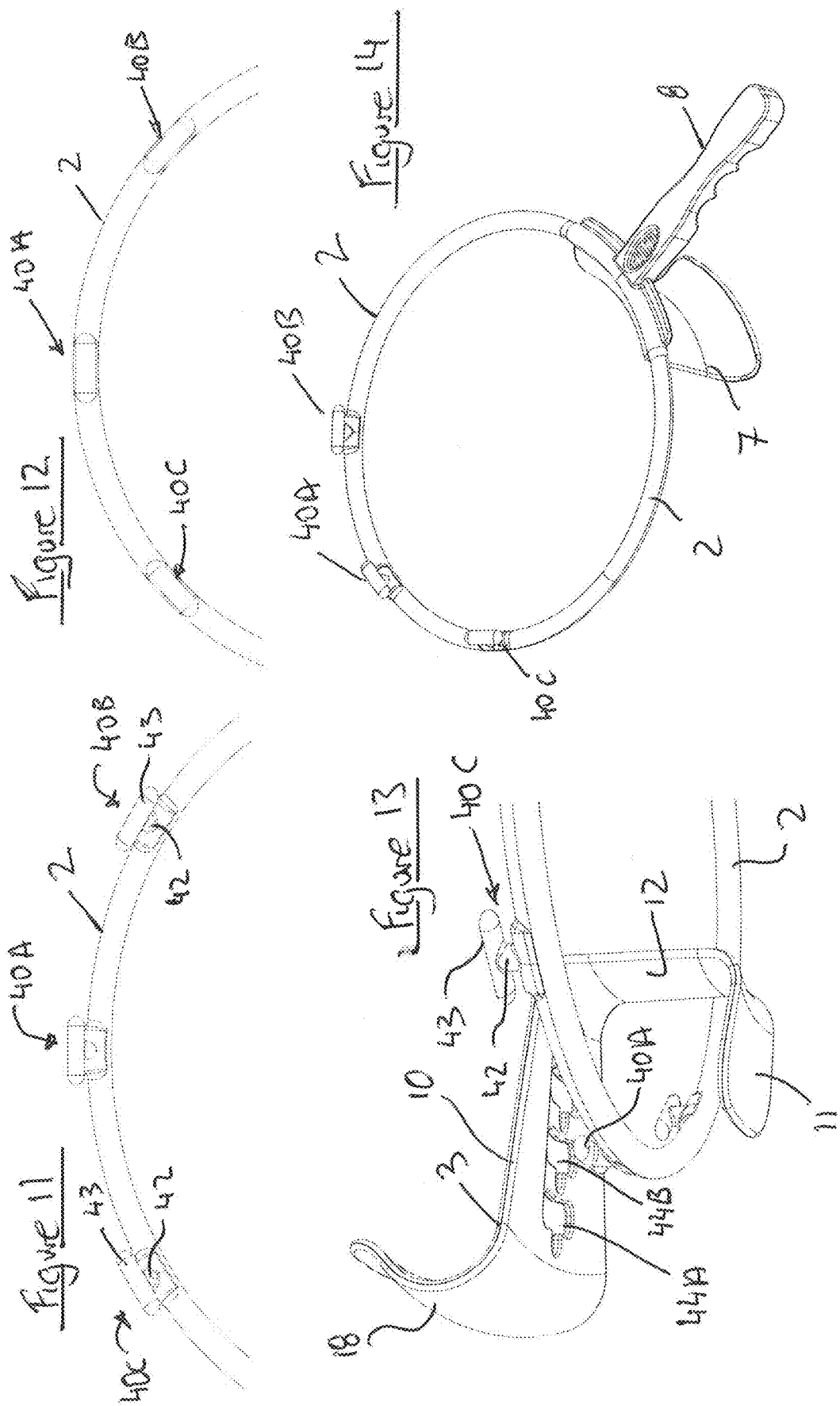

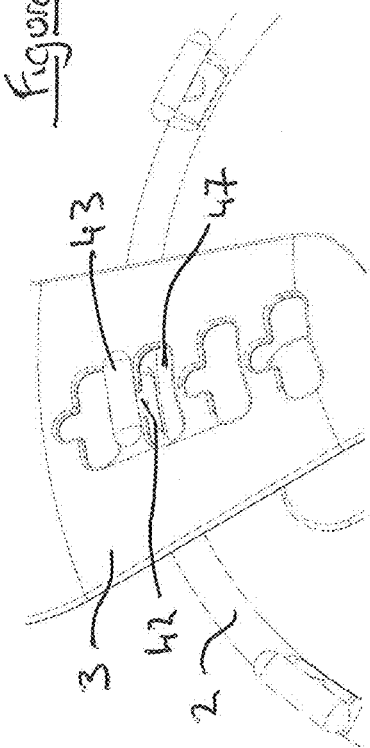
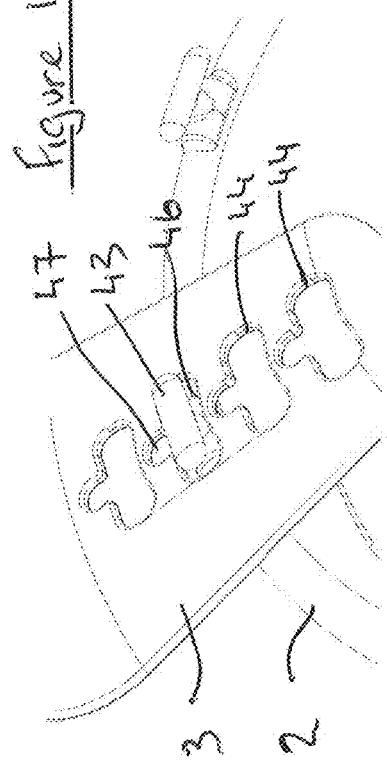
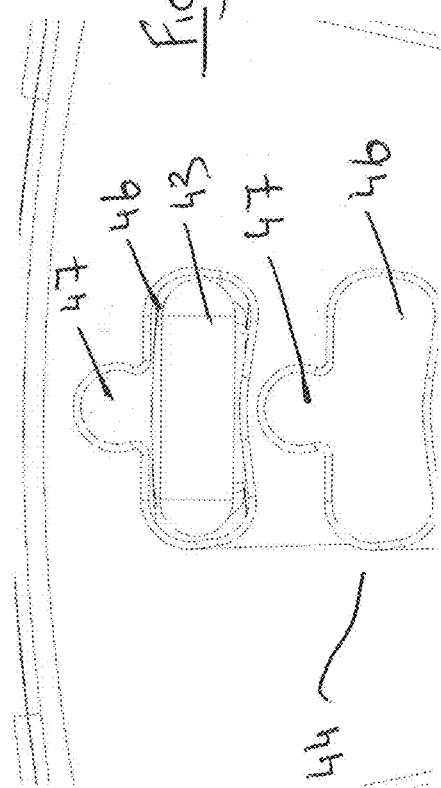

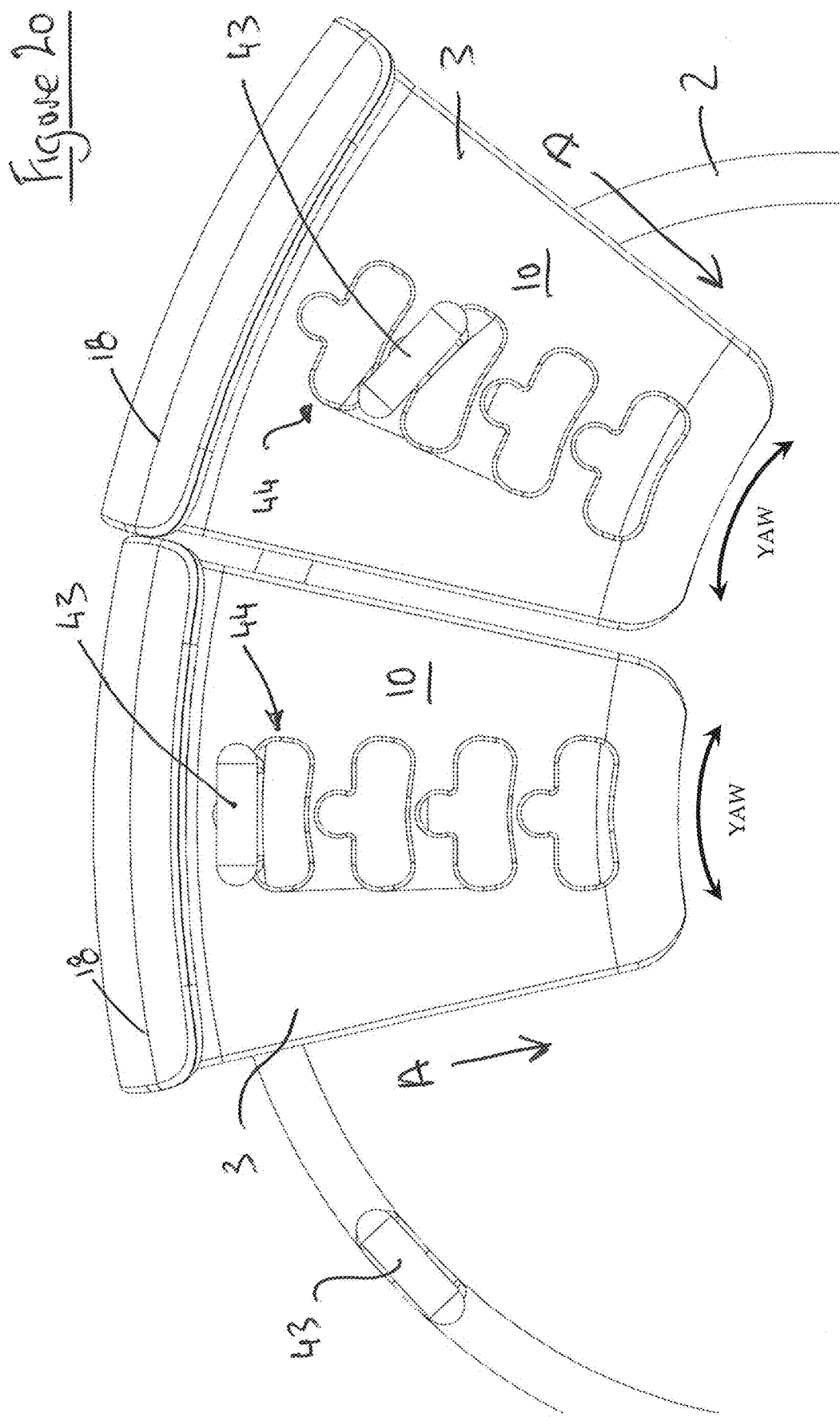

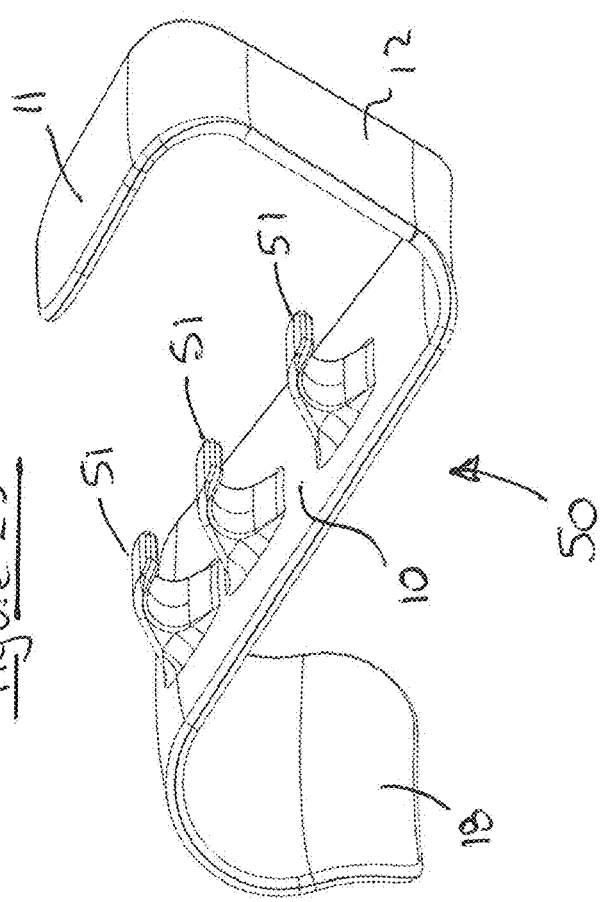
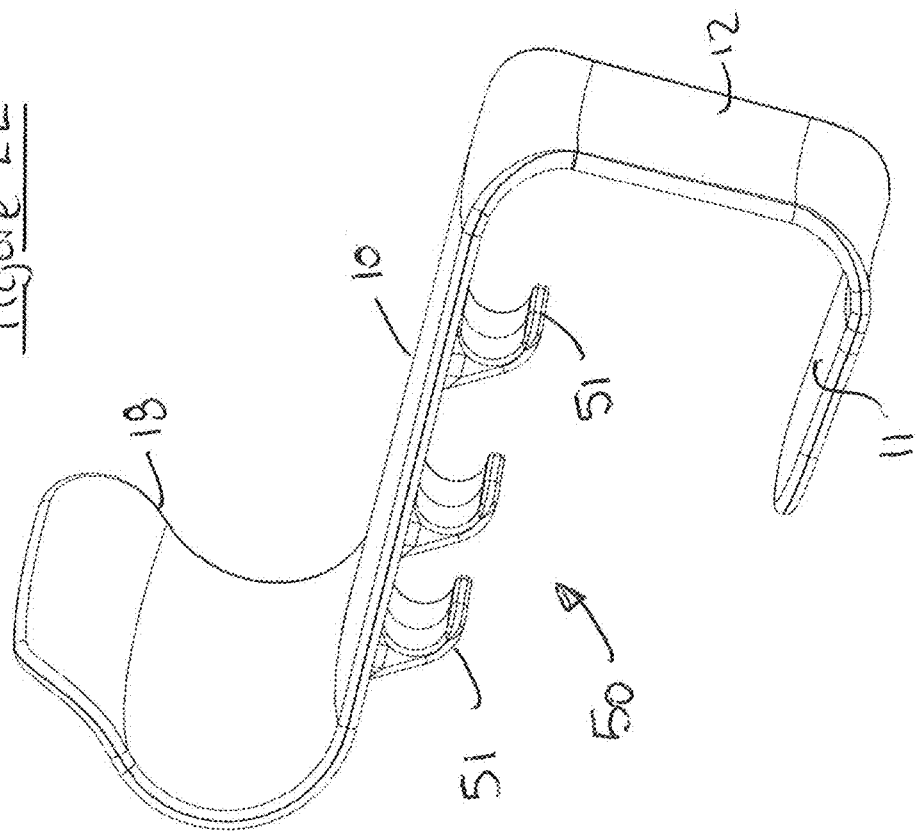

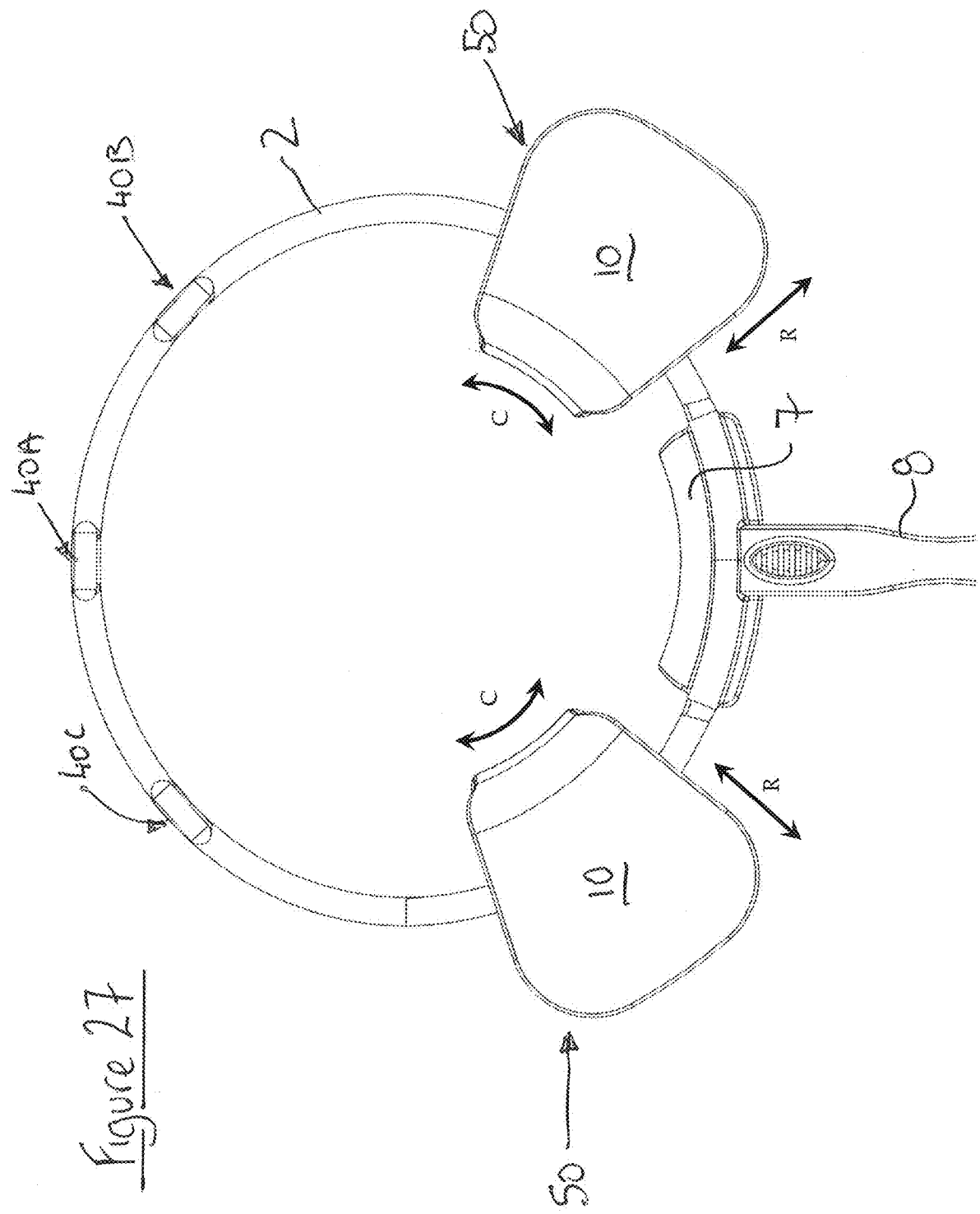

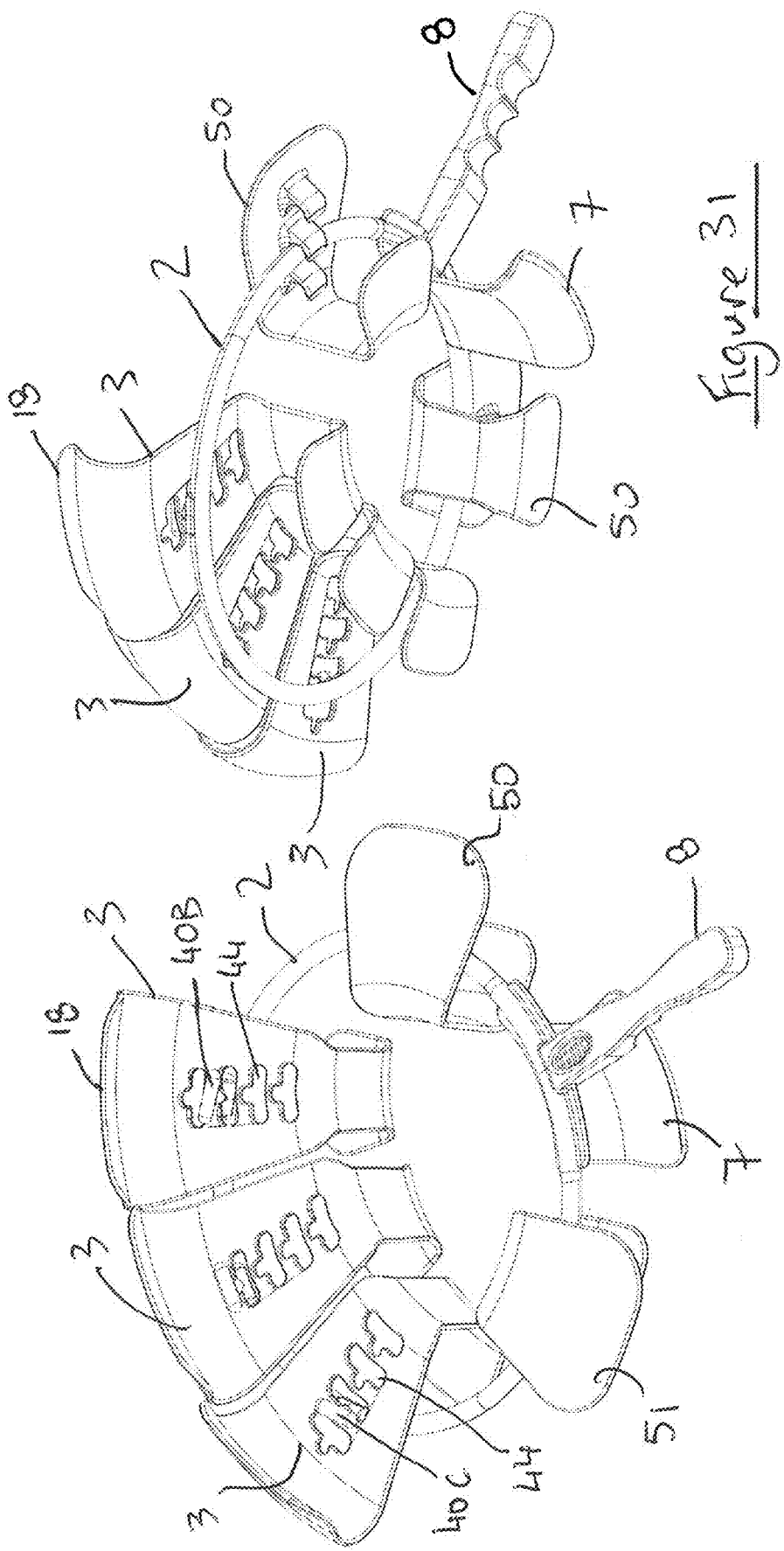

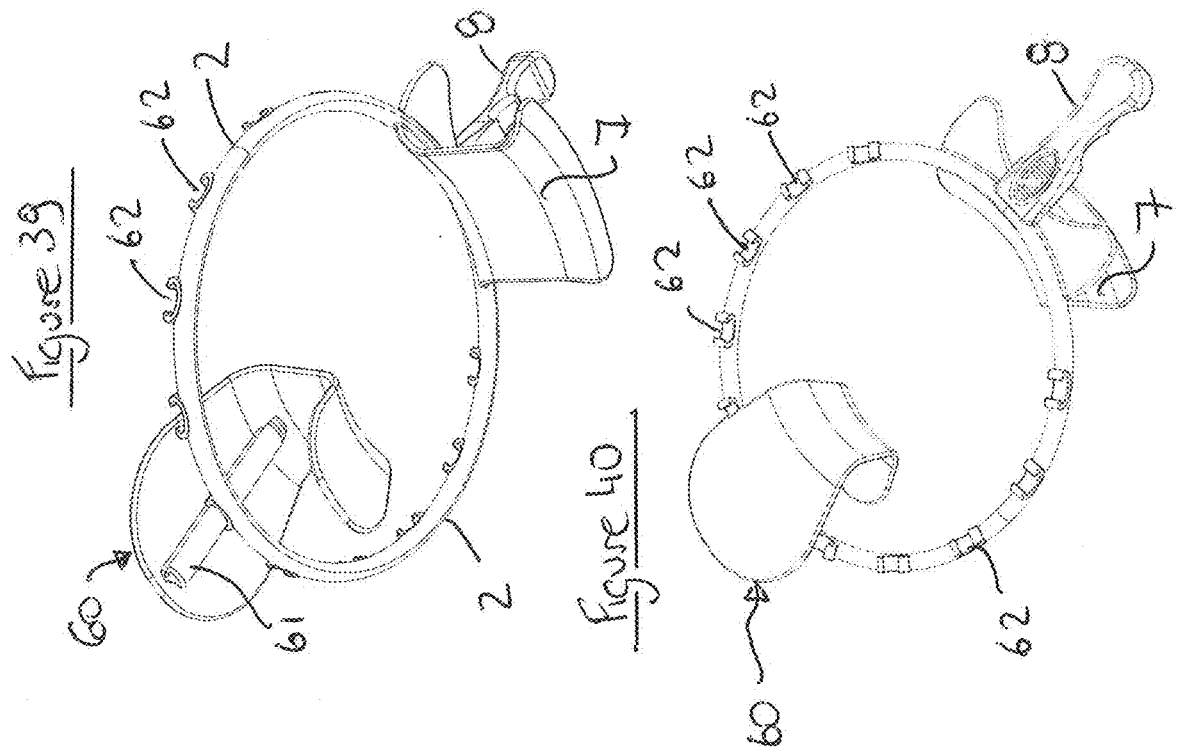
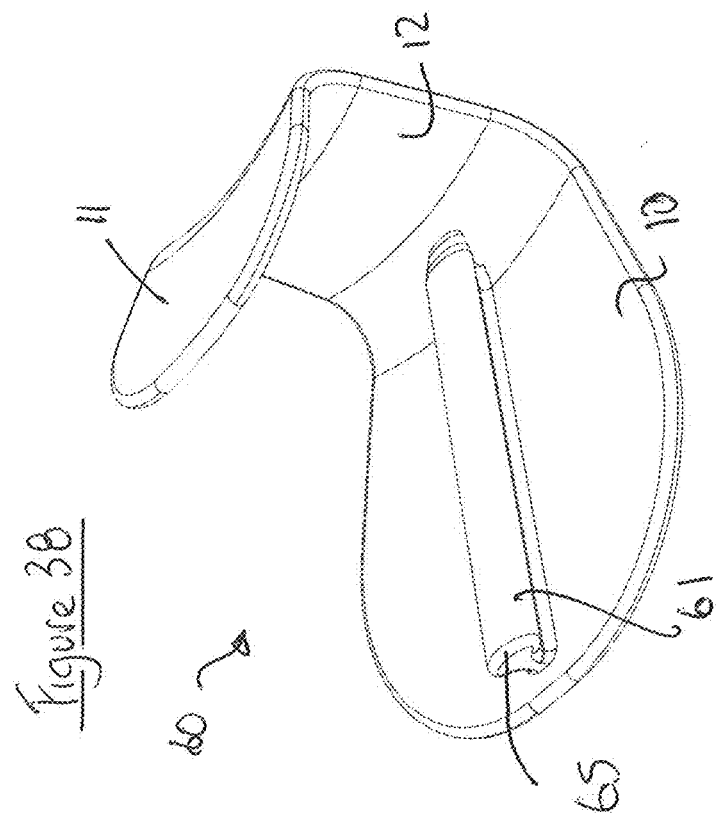

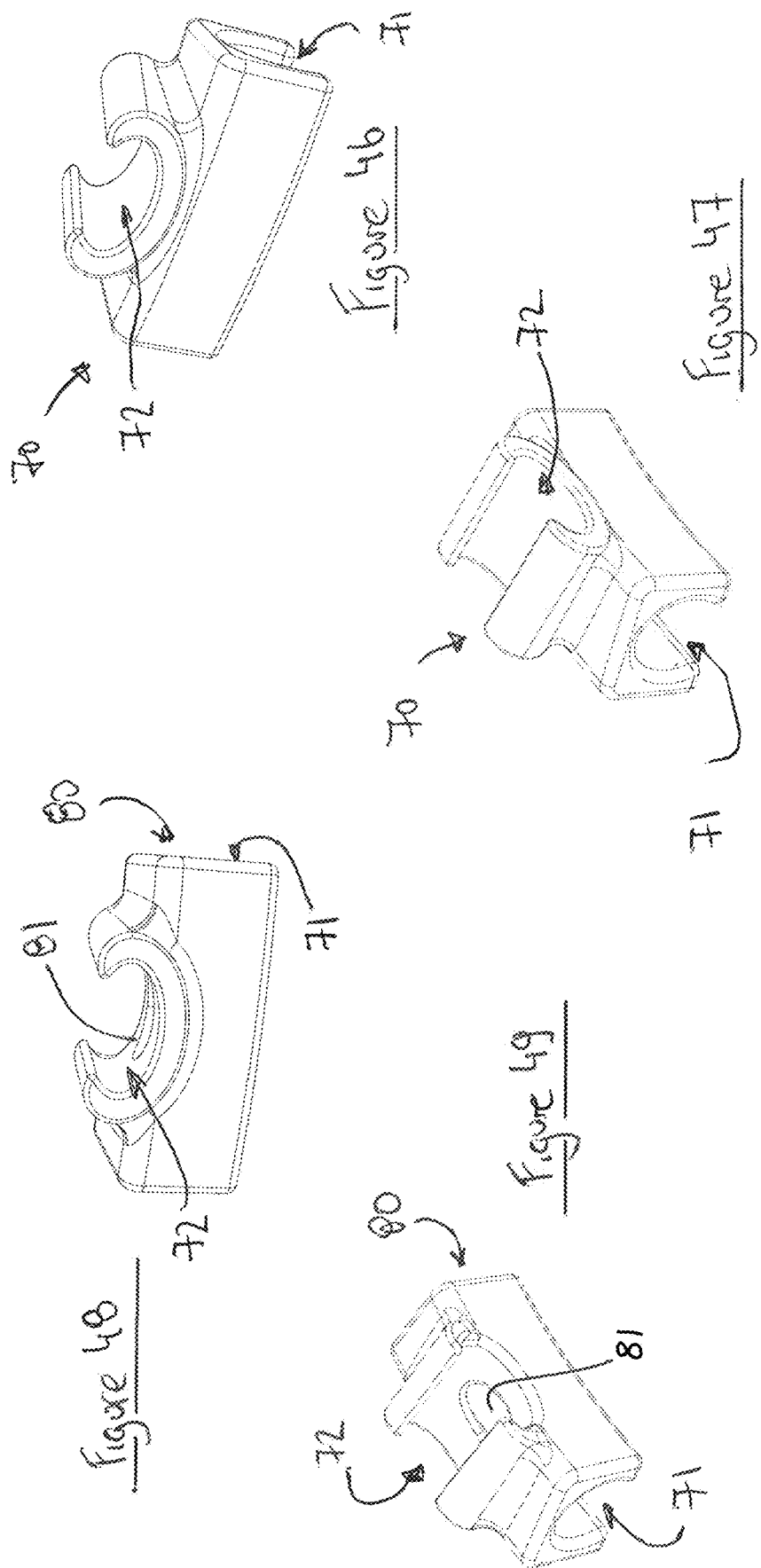

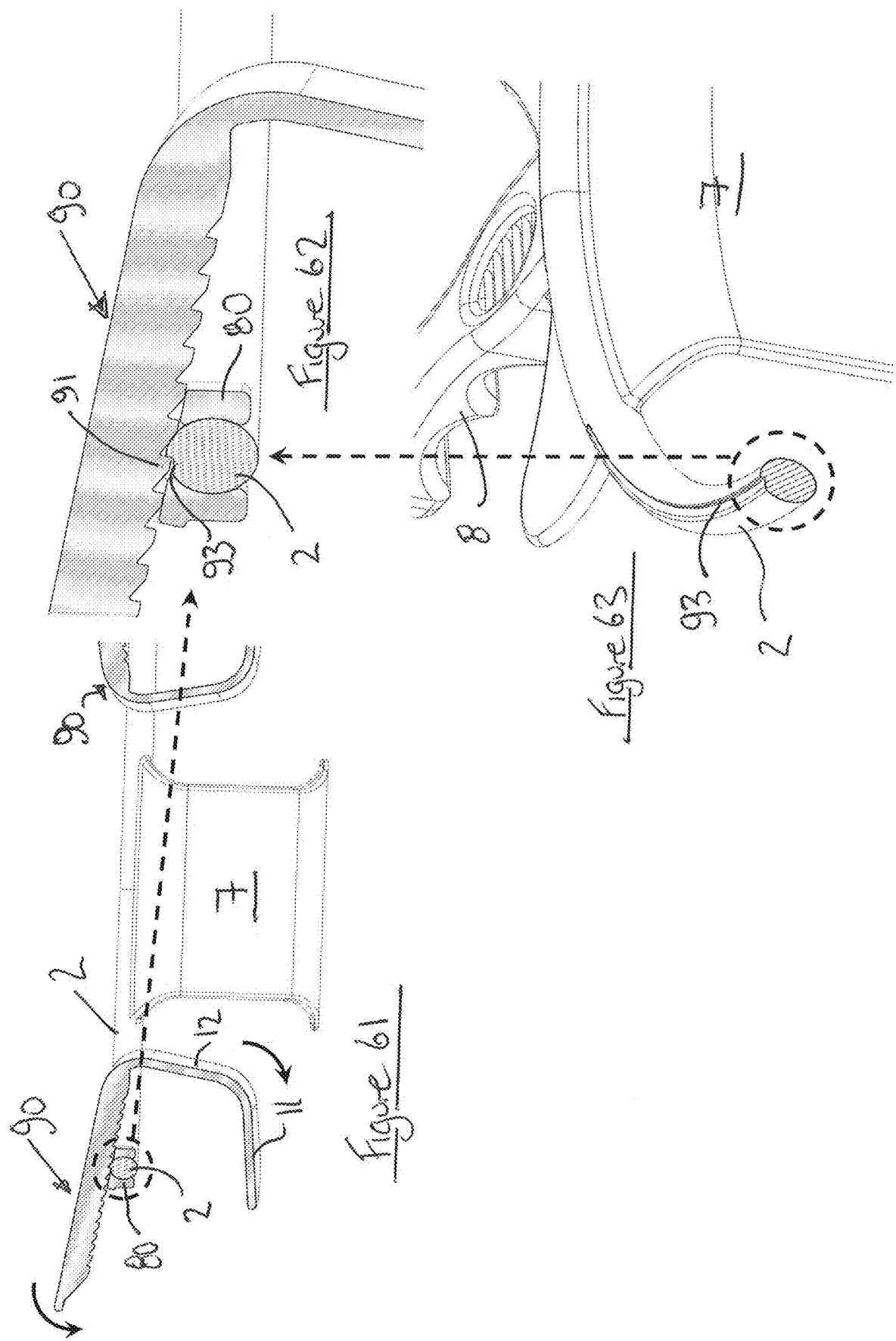

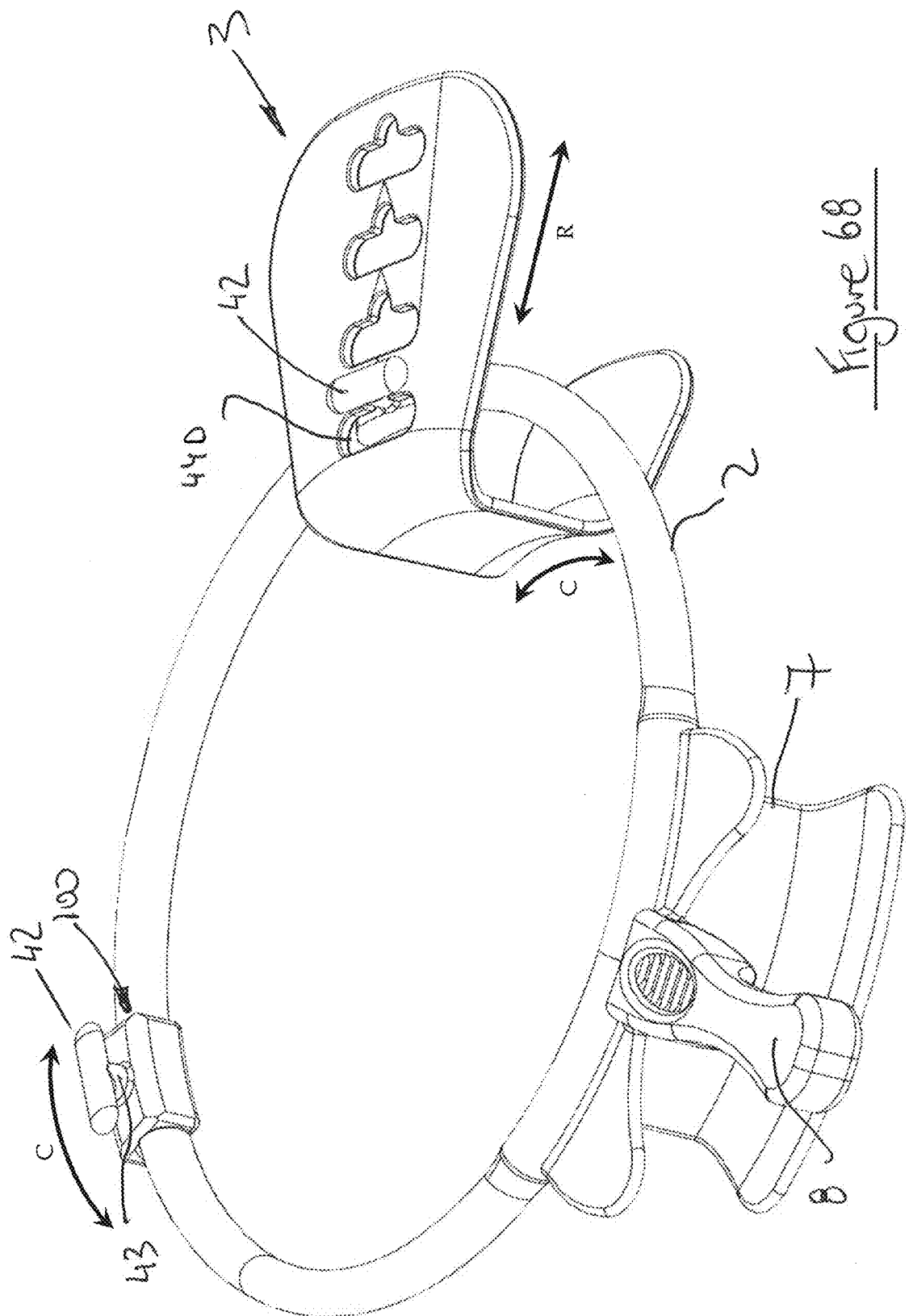

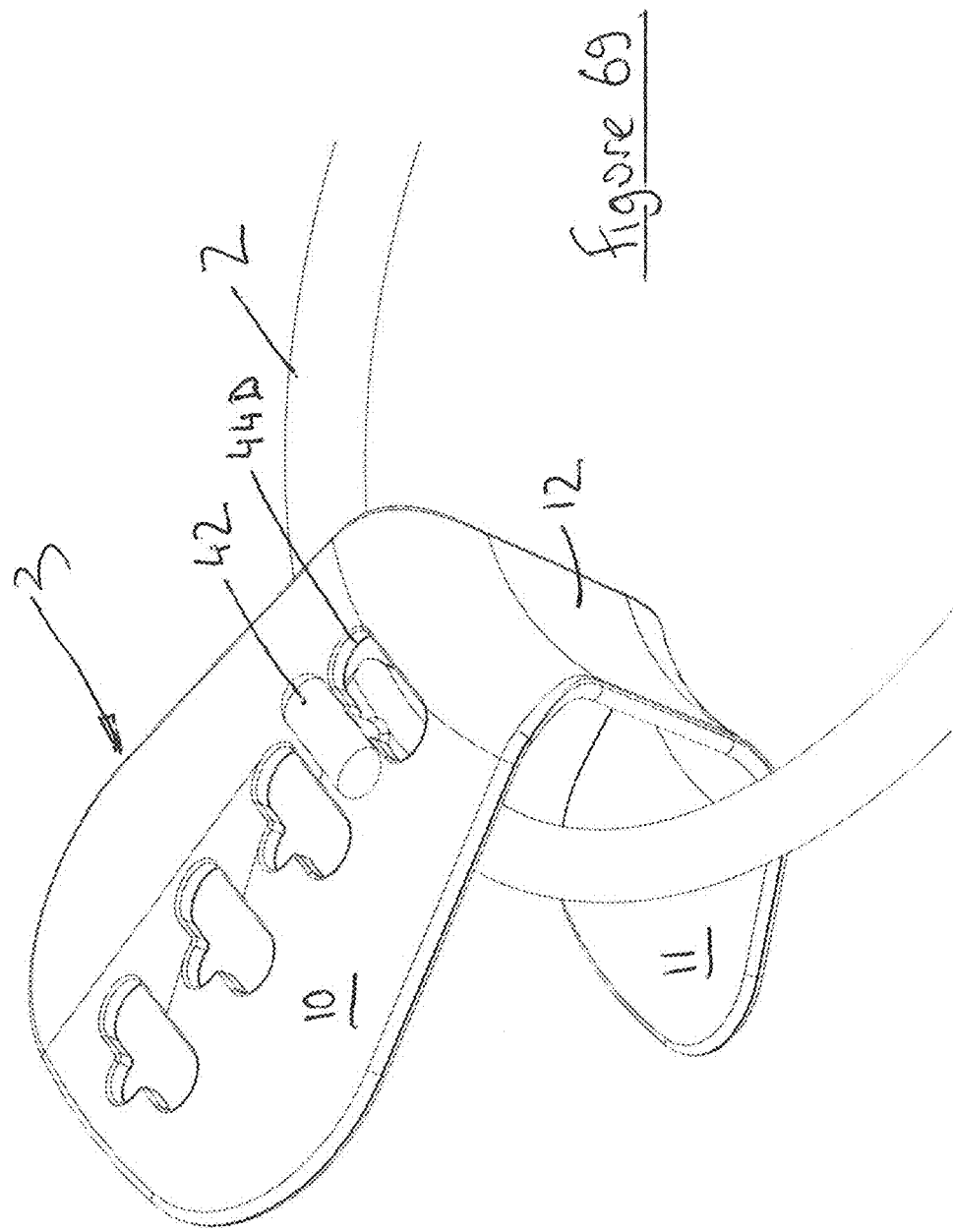

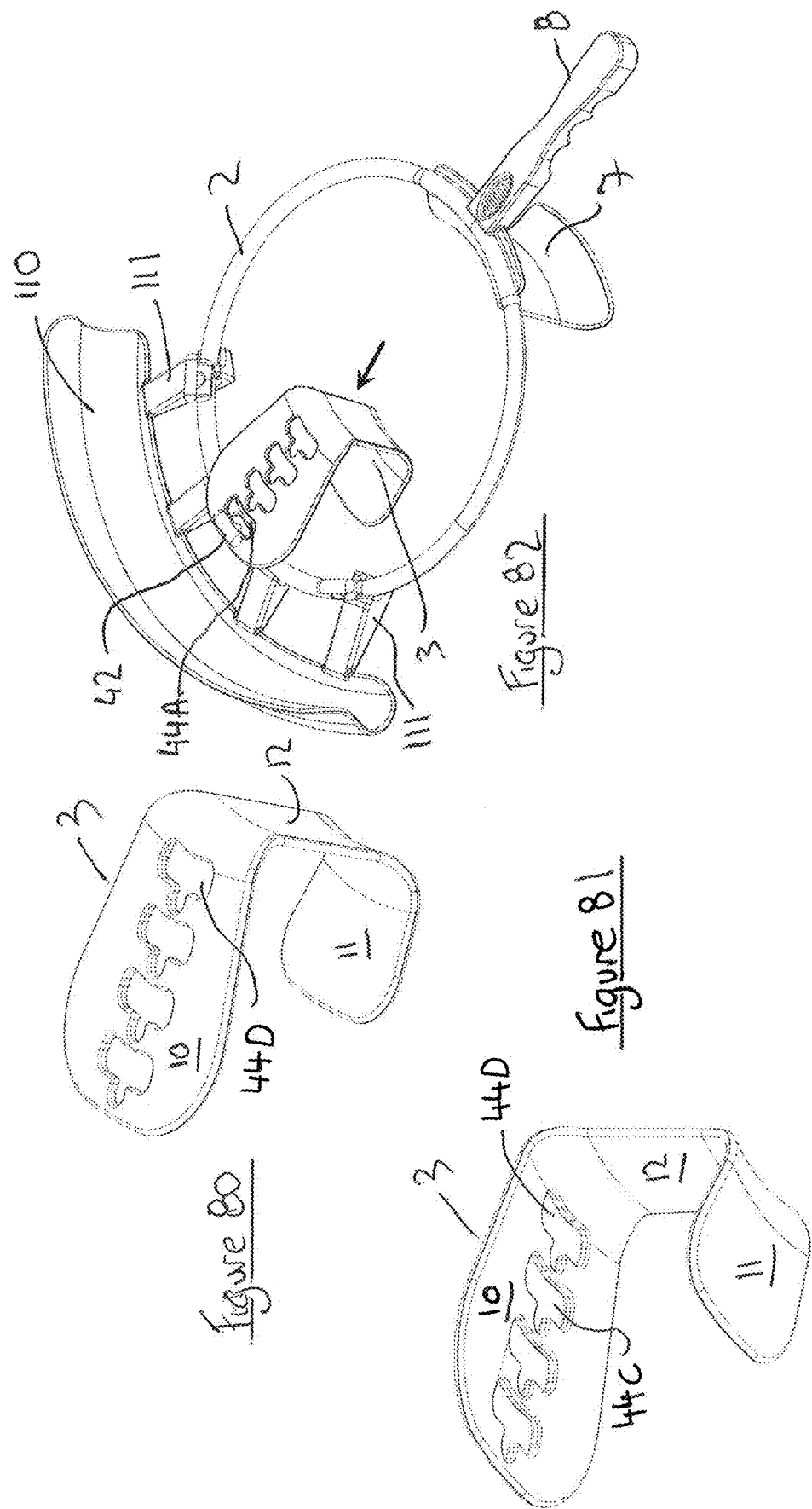

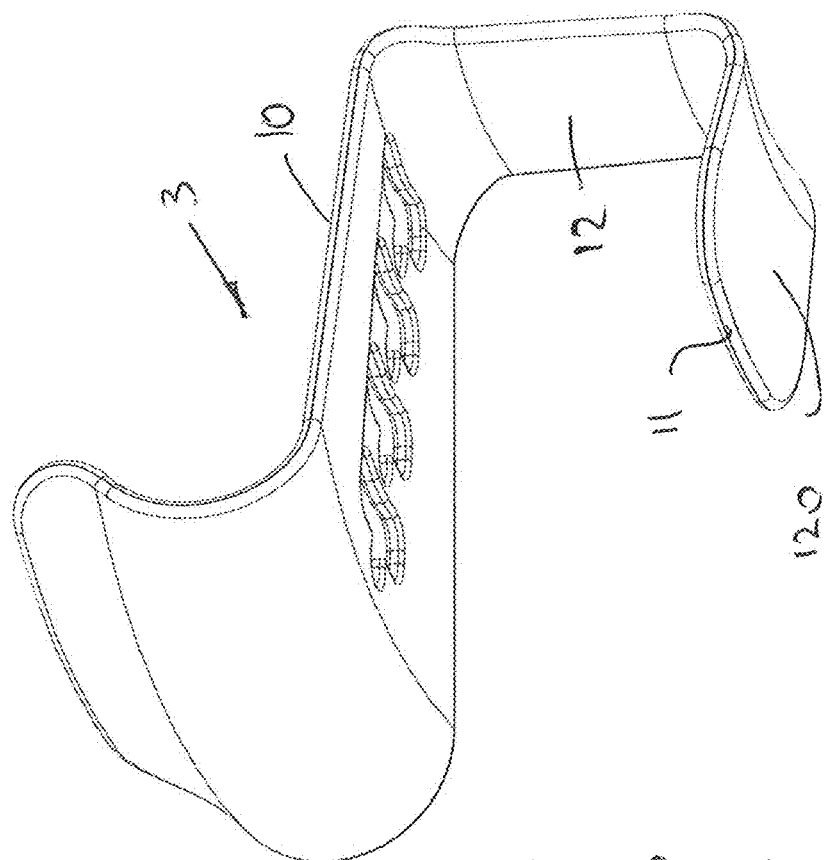
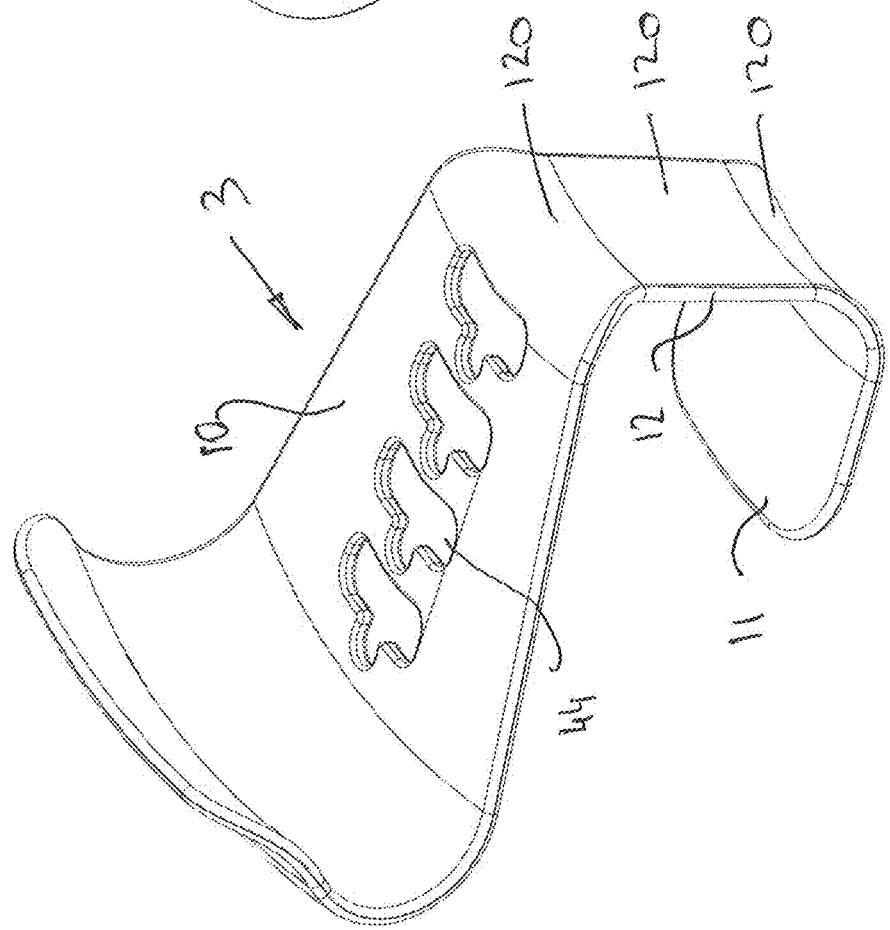

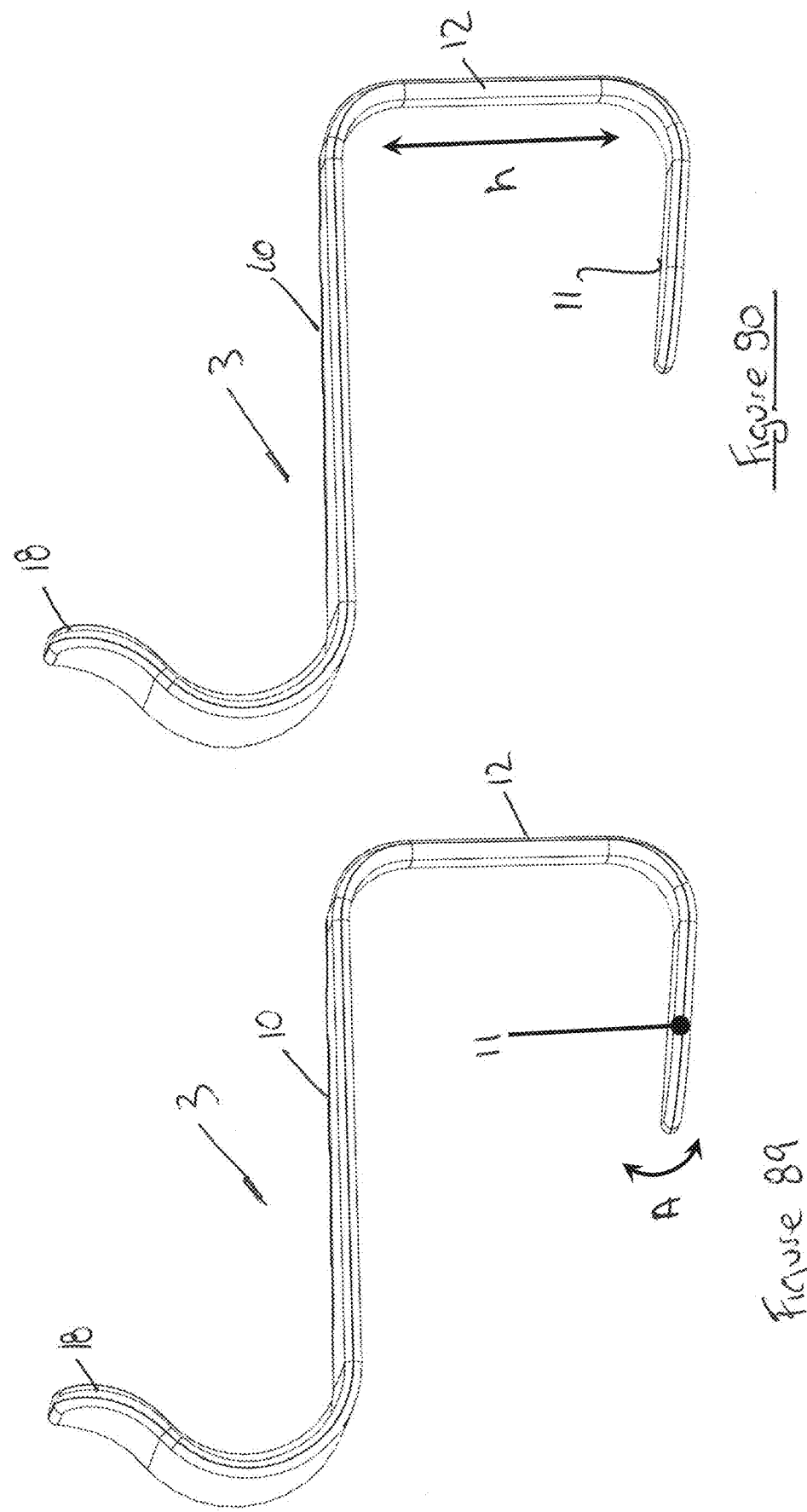

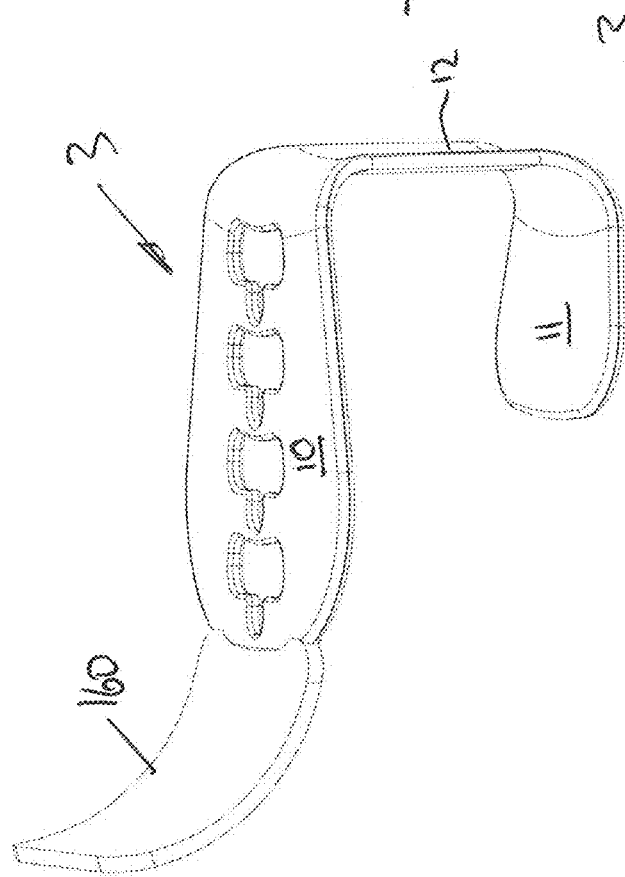
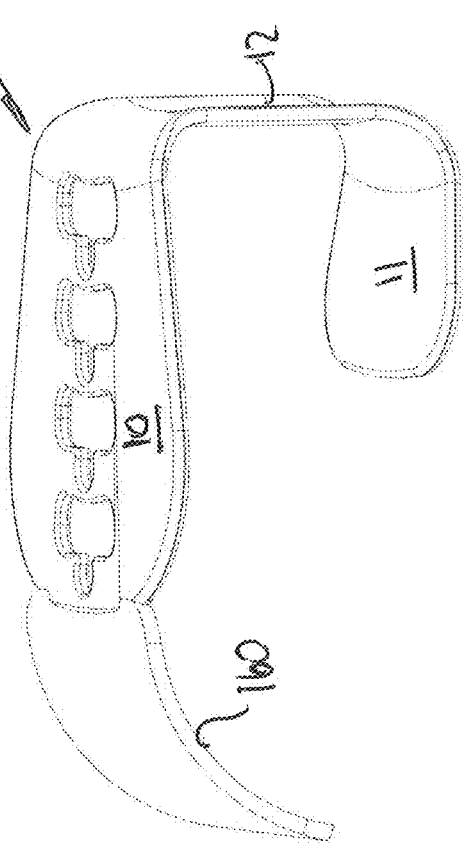

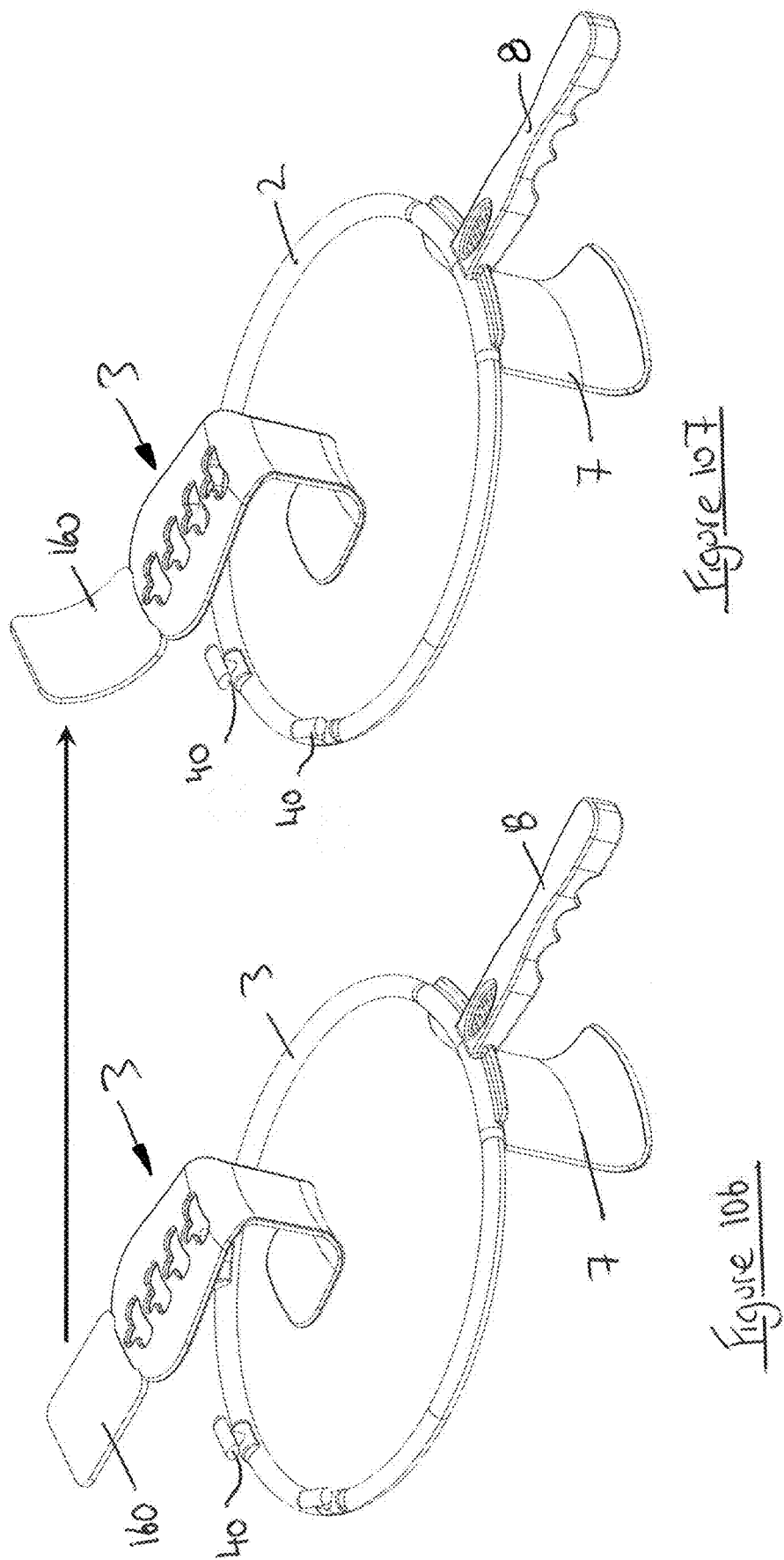

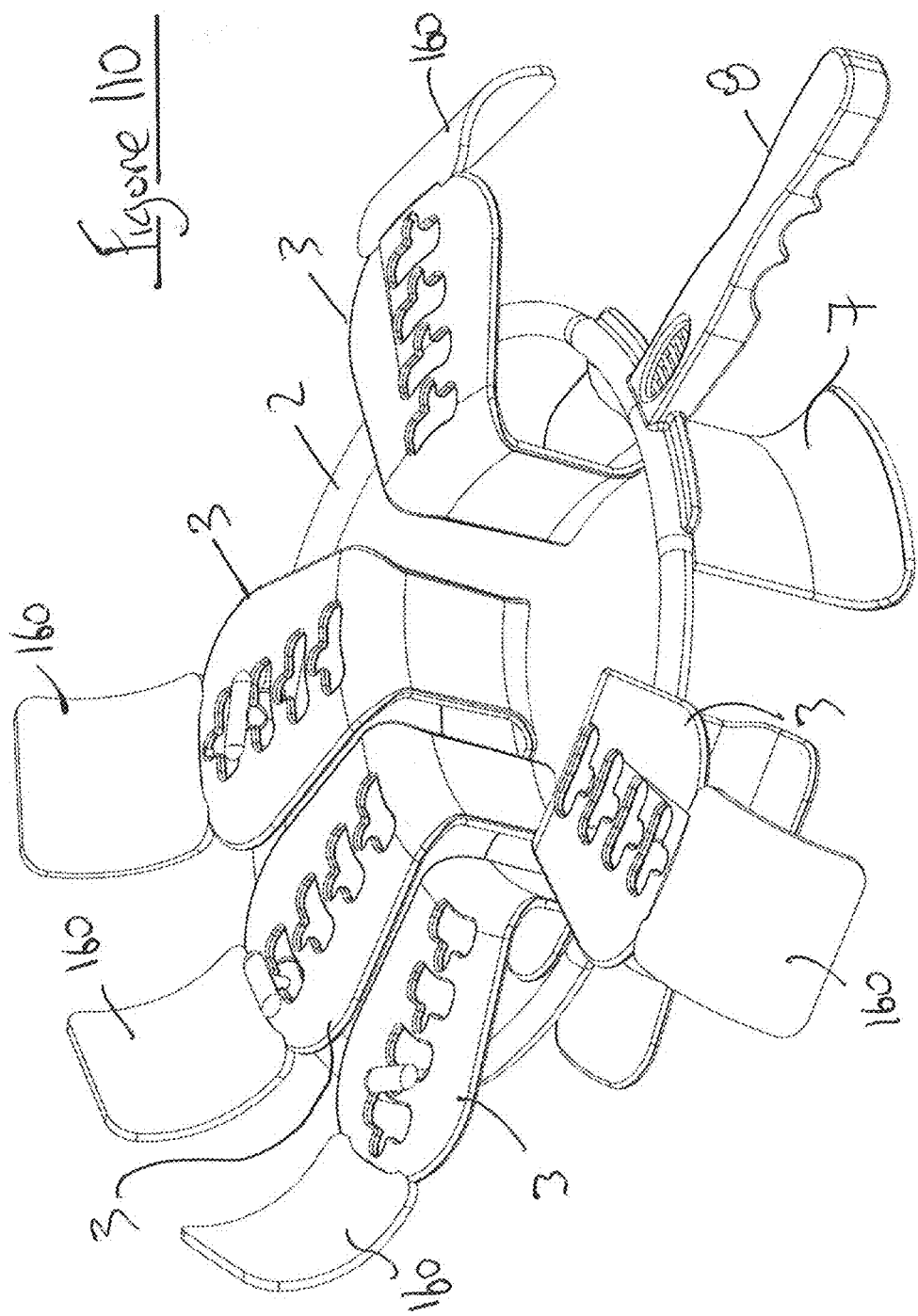

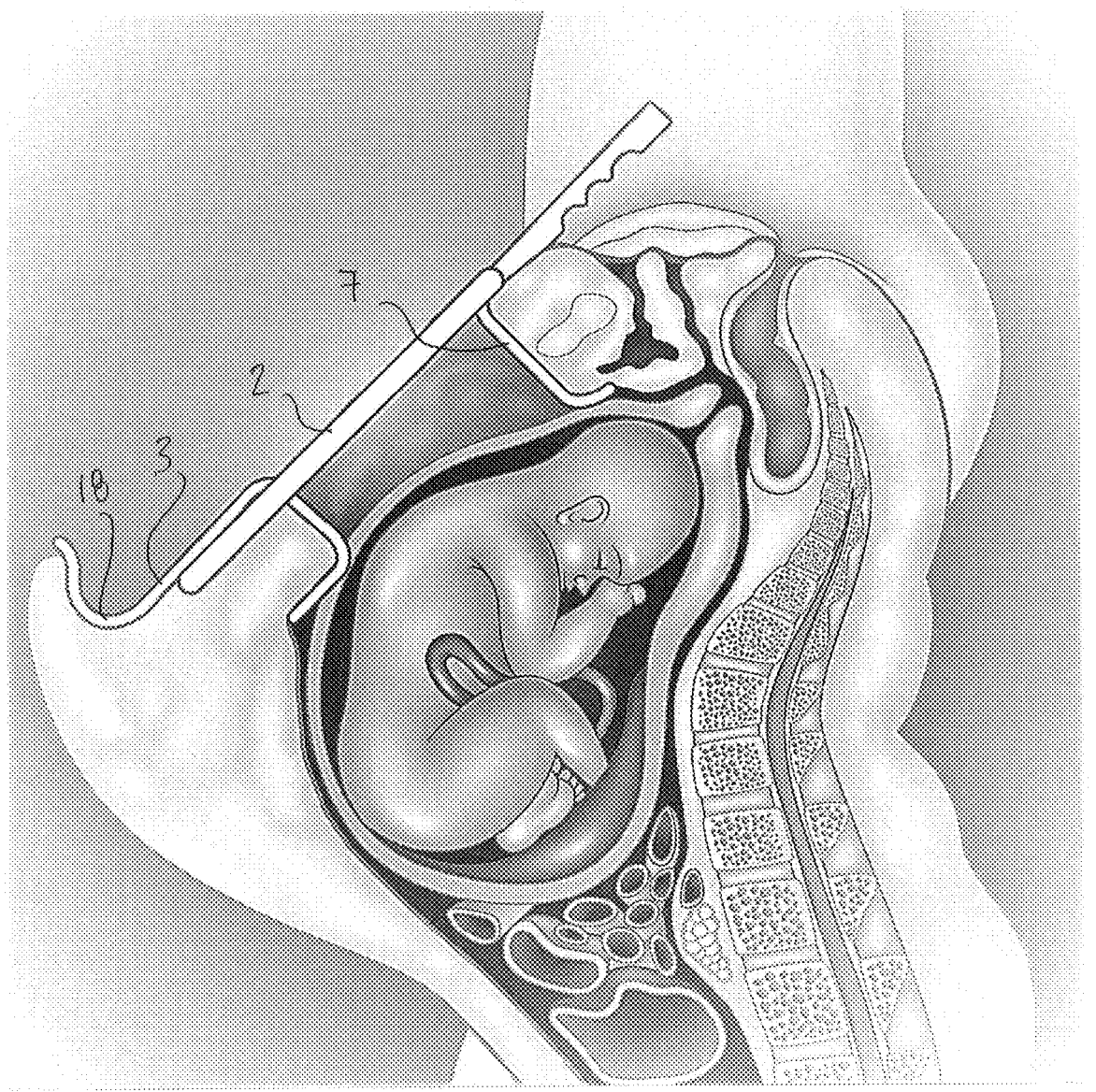
Fig. III

METHOD OF FACILITATING ACCESS TO A NEONATE THROUGH A CAESAREAN INCISION IN THE WOMAN'S ABDOMEN BY OPENING THE INCISION

CROSS REFERENCE TO RELATED APPLICATIONS

This application is a continuation of U.S. application Ser. No. 17/086,054, filed Oct. 30, 2020, which claims priority to European Application No. 19206358.4, filed Oct. 30, 2019, the entire disclosure of each of which is hereby incorporated herein by reference in its entirety.

FIELD OF THE INVENTION

The present invention relates to a method of facilitating access to a neonate through a caesarean incision in the woman's abdomen by opening the incision.

BACKGROUND TO THE INVENTION

Caesarean Section is a surgical procedure to achieve delivery of a neonate through an open abdominal incision (laparotomy) and an incision in the uterus (hysterotomy).

There are a number of techniques a surgeon may employ to achieve a caesarean delivery. One such technique is a Pfannenstiel-Kerr method. The Pfannensiel skin incision is slightly curved and located approximately 3 centimetres above the patient's symphysis pubis. The surgeon must then incise through the subcutaneous layer, which can vary from 2 centimetres to 5 centimetres thick, depending on the patient BMI, until the fascia is reached. The fascia is then incised, and the underlying rectus muscle is separated in the midline, in order to reach the peritoneum layer. Entry into the peritoneal cavity is achieved through opening the peritoneum layer. In a gravid woman, the uterus is often encountered at this point, upon entry into the abdomen.

It's typically at this point in the procedure, where the use of a hand-held metal retractor is used to assist in the management of the abdominal tissues. A retractor such as a Doyen retractor, which is often referred to as a 'bladder blade' is inserted into the open abdominal cavity. It is positioned at the lower end of the incision, just above the symphysis pubis and is used to protect the bladder from accidental injury during the procedure.

Additional hand-held metal retractors are typically also used to retract the abdominal wall tissue in order to access and visualise the uterus. Once the incision has been made in the uterus and delivery of the neonate has been achieved, the surgeon needs to repair the uterus. The time from when the surgeon accesses the peritoneal cavity, to delivery of the neonate and subsequent repair of the uterus, can typically range from 20 minutes to 40 minutes. Delivery of the neonate often occurs within the first 5 minutes of this time period.

During this time, it is important to maintain good visualisation and access of the uterus within the abdominal cavity in order to ensure a successful outcome for the patient. The use of hand-held metal retractors to hold open the incision space has a number of disadvantages. Each retractor requires the use of an assistant's hand to withdraw the tissue. With the duration of the requirement to withdraw the abdominal tissue, in the region of 20 to 40 minutes, the assistant experiences fatigue and strain, which is exacerbated when dealing with a high BMI patient. Additional assistants are typically required for a high BMI patient, but there is restricted space for them to work, due to the nature of the primary surgeon standing on one side of the operating table and the main assistant standing on the opposite side of the operating table.

Another disadvantage of the hand-held metal retractors is that they cannot be used to hold open the incision during the delivery of the neonate, due to the risk of injury to the neonate. They must therefore be removed and substituted for assistant's hands, during neonate delivery. The hand-held metal retractors are then reinserted into the abdominal cavity for the repair of the uterus. This constant switching in and out of the hand-held metal retractors, along with the assistant's hands in the abdominal cavity, leads to a higher risk of bacteria transfer into the incision site and subsequently increases the risk of the patient acquiring a Surgical Site Infection (SSI) as a result of the procedure.

In the case of a high BMI or obese patient, further assistance is often sought from additional medical staff, to use their hands to pull back & hold the abdominal tissue out of the way of the performing surgeon, as required. This can provide immediate effectiveness for the surgeon but costs time & money for additional staff and causes physical strain & fatigue for those staff, as they are often placed in awkward positions to manage the abdominal flesh while also keeping out of the way of the lead surgeon and primary assistant. With the increasing number of assistant's hand inside the patients abdominal cavity, there is a proportional increase to the risk of bacteria transfer into the incision site and subsequently an increase to the risk of the patient acquiring a Surgical Site Infection (SSI) as a result of the procedure. There are also self-retaining metal retractors available, such as the Balfour retractor or the Collins retractor, but these are not typically used for caesarean sections as they are unsuitable for delivery of the neonate through them, when deployed in the patient. They also take time to set up and have been designed for use in standard abdominal surgery, not caesarean sections.

An alternative option to the hand-held and self-retaining metal retractors are the plastic double-ring disposable retractors, consisting of an inner & outer ring held together with a hammock of clear flexible film which protects the wound edge. The primary competitors in this area are the Alexis O Retractor (by Applied Medical), SurgiSleeve (by Medtronic) and OB/Mobius (by Cooper Surgical). All of these competitors achieve retraction of the surgical space in a similar way. However, these products are adapted from other surgeries so none of them address the particular clinical & ergonomic needs of caesarean surgery.

In the double-ring disposable retractor, the retraction is achieved by inserting the inner ring completely inside the abdominal cavity and subsequently tightening the outer ring towards the patient's abdomen. The achieved opening is a function of how tight the outer ring can be twisted in order to create sufficient tension in the clear flexible 'hammock' material, between the inner and outer ring, in order to hold back the abdominal wall at the incision site. The double-ring disposable retractor products keep the incision site symmetrically held open and are safe to deliver a baby through, however they lose their effectiveness when dealing with high BMI or obese patients because they are not capable of effectively holding back a dense wall of abdominal tissue. This is because the retraction forces required to hold back the abdominal wall, on a high BMI or obese patient, are difficult to achieve with the double-ring method. The inner ring has an increased risk of 'pop out' from the abdominal cavity due to the degree of tension required between the rings, in order to achieve good visualisation of the uterus.

A further disadvantage of the double-ring disposable retractor is that they also hinder the surgeon if, during the procedure, the surgeon needs access to the underlying abdominal tissue, for example, to either cauterise a bleeding vessel or to increase an incision length in the fascia. In this scenario, the surgeon would need to completely remove the double-ring retractor and subsequently must reinsert it, leading to an increase in procedure time and an increased risk of bacteria transfer into the incision site.

A further disadvantage of the self-retaining metal retractors and the double-ring disposable retractors is that neither of these addresses the problem of managing the overhanging pannus, which is a particular problem when dealing with high BMI or obese patients. On certain high BMI or obese patients, the overhanging abdominal pannus can encroach on the surgical incision site during the procedure. This leads to an increased risk of bacteria transfer into the incision site and subsequently increases the risk of the patient acquiring a Surgical Site Infection (SSI) as a result of the procedure.

The encroachment of the overhanging pannus onto the surgical incision site also hinders the requirement for good visualisation of the uterus and therefore needs to be held back during the procedure. Some techniques employed to achieve this involve taping of the pannus to the patient's chest or otherwise anchoring the pannus to the operating table, towards the patient head, in order to keep the surgical incision site clear.

U.S. Pat. No. 4,421,107 describes a self-retaining metal surgical retractor comprising a supporting ring and a plurality of radially adjustable retractor paddles attached to the ring at defined positions are the ring. During use, the retractor is placed over the incision, and the paddles engage the incision before being radially retracted to open the incision while attached to the ring. The circumferential position of the paddles on the ring cannot be adjusted during the surgery.

U.S. Pat. No. 6,582,364 describes a double-ring disposable surgical retractor whereby the inner ring is inserted into the abdominal cavity via the incision site and the flexible tubular shaped connecting material is tensioned between the inner and the outer ring, in order to achieve retraction of the incision site.

Surgical access system including abdominal surgery access systems are described in US2011/021879, US2019/254651, U.S. Pat. No. 2,473,266, WO2011158046 and WO2018/119473. Many of the systems disclosed describe supporting rings and tissue retracting arms configured for adjustable attachment to the supporting ring. Many of the devices employ long metal retraction blades which would be unsuitable for a Caesarean section procedure and delivery of a neonate. In addition, the mechanisms for coupling the blades to the supporting ring are complicated and require two hands to operate. In addition, in all devices the retraction blades are clamped tightly to the supporting ring.

The challenges described above, in relation to caesarean delivery on high BMI and obese patients are not being addressed by the current devices on the market. These challenges need to be overcome in order to improve surgical outcomes for the female patient, the safe delivery of the neonate and to improve the ergonomics of the procedure for the surgeon and the accompanying assistant.

It is the object of the invention to overcome these challenges by providing a device and method of use, which will facilitate positive patient outcomes and improve the ergonomics of the caesarean delivery procedure for the surgeon. The existing devices do not adequately address these challenges.

It is an object of the invention to overcome at least one of the above-referenced problems.

SUMMARY OF THE INVENTION

The Applicant has addressed the problems of the prior art by providing a surgical access system having a supporting ring and one or more self-retaining retractors detachable mountable to the ring. In one aspect, the supporting ring comprises a non-adjustable retractor and an adjacent handle that are usually integrally formed with the supporting ring, where the non-adjustable retractor is configured to cover and hold back the bladder of the woman during the procedure. The combination of the non-adjustable retractor and handle allows a surgeon easily articulate and partially anchor the supporting ring to the patient on a pelvic side of the incision with the non-adjustable retractor covering the woman's bladder, and then use the detachable retractor to cup a section of tissue on an abdominal side of the incision and retract the tissue manually before attaching the detachable retractor to the ring in a tissue retraction position, thereby fully anchoring the ring to the opened incision. Additional detachable retractors may then be used to further open the incision.

In one aspect, coupling elements are provided to attach the or each detachable retractor to the ring that are configured to allow a degree of play between the retractor and the ring when they are attached together in a tissue retracting position, in particular allowing pitch and/or yaw of the retractor. This has been found to be highly beneficial in the context of a Caesarean section procedure, where the retractors are configured to be secured radially allowing the safe securement of the incision in an open orientation while allowing controlled pitch and yaw movement of the retractors during the procedure, which allows positional adjustment of the retractors during delivery of the neonate minimising the risk of trauma to the neonate. In one aspect, the retractors have a proximal upwardly depending lip configured to deflect panniculus of a woman, especially an obese woman.

In a first aspect, the invention provides a surgical access system adapted to facilitate access to a surgical site through an incision in a patient's body by opening the incision, comprising:

a supporting ring;

at least one retractor configured to cup and manually retract a section of abdominal tissue at the incision; and coupling elements configured for retrofitting the or each retractor to the supporting ring in a tissue-retracting position.

In any embodiment, the system is adapted to facilitate access to a neonate through a Caesarean incision in the patient's abdomen and the supporting ring is dimensioned to allow delivery of a neonate through the ring. The system may be adapted to perform other surgeries, especially abdominal surgeries.

In any embodiment, the or each retractor is a saddle-shaped retractor.

In any embodiment, the or each retractor is a radially adjustable retractor.

In any embodiment, the system comprises a non-adjustable saddle-shaped retractor fixed (e.g. integrally formed) to the supporting ring and optionally an outwardly projecting handle fixed to the supporting ring adjacent the fixed saddle-shaped retractor.

In any embodiment the fixed retractor and handle are disposed in a facing relationship on the ring.

In any embodiment, the non-adjustable saddle-shaped retractor is a pelvic region retractor configured to cover and hold back the woman's bladder during a caesarean section.

In any embodiment, the coupling element for the or each retractor comprises a first formation disposed on the supporting ring and a corresponding second formation on the retractor configured for coupling with the first formation.

In any embodiment, the first formation is positioned on a top surface of the retractor facing away from the skin of the patient during use.

In any embodiment, the first formation is detachably attachable to the supporting ring (e.g. it can be configured for snap-fit engagement with the supporting ring, typically at any point along the ring).

In any embodiment, the first formation is integrally formed with the supporting ring.

In any embodiment, the first and second formations are configured to allow the retractor pitch and/or yaw relative to the supporting ring when the retractor is fitted to the ring in a tissue retracting position. This allows the retractor when attached to the ring to positionally adjust during a surgical procedure to adjust the size and shape of access to the surgical site. It is especially useful during a caesarean section procedure when delivering a neonate through the caesarean incision as the ability of the retractors to positionally adjust relative to the supporting ring lowers the risk of trauma to the neonate during delivery.

In any embodiment, the formations of the coupling element are configured to allow the retractor pitch and yaw relative to the supporting ring when the retractor is fitted to the ring in a tissue retracting position.

In any embodiment, the formations of the coupling element are configured to allow the retractor pitch outwardly by up to 10° or 15°.

In any embodiment, the formations of the coupling element are configured to allow the retractor pitch inwardly by up to 5° or 10°.

In any embodiment, the formations of the coupling element are configured to allow the retractor yaw by +/−45°

In any embodiment, the formations of the coupling element are configured to allow the retractor roll relative to the supporting ring when the retractor is fitted to the ring in a tissue retracting position.

In any embodiment, the formations of the coupling element are configured to allow the retractor roll on each side by up to 2°.

In any embodiment the supporting ring has an elliptical profile. Other profiles include circular and oval.

In any embodiment, the system comprises at least two radially adjustable saddle-shaped retractors.

In any embodiment, the system comprises at least three radially adjustable saddle-shaped retractors.

In any embodiment, the system comprises at least one and preferably two, three or four retractors that are each radially adjustable and circumferentially adjustable.

In any embodiment, the system is configured for attachment of a radially adjustable retractor to the supporting ring at a position on the ring diametrically opposed to the fixed retractor. Thus, when the fixed retractor is positioned at 180°, the system may be configured for attachment of the radially adjustable retractor at 0°.

In any embodiment, the system is configured for attachment of a radially adjustable retractors to the supporting ring at positions flanking a point of the ring that is diametrically opposed to the fixed retractor. Thus, when the fixed retractor is positioned at 180°, the system may be configured for attachment of radially adjustable retractors at 10 o'clock (or anywhere between 270° and 330°) and 60° or anywhere between 30° and 90°).

In any embodiment, the system is configured for attachment of a radially adjustable retractor to the supporting ring at a central position on the ring diametrically opposed to the fixed retractor and attachment of a radially adjustable retractors to the supporting ring at positions flanking the central position.

It will be appreciated that when the first formations on the supporting ring are integrally formed with the ring, the position of the formations will determine the circumferential position of the retractors on the ring. Thus, in one embodiment, the ring has a central first formation positioned on the ring diametrically opposed to the fixed retractor and optionally flanking first formations disposed on the ring on each side of the central first formation. In another embodiment, the ring has flanking first formations disposed on the ring on each side of a point on the ring diametrically opposed to the fixed retractor.

In any embodiment, the or each radially adjustable saddle-shaped retractor comprises an upwardly depending lip configured to deflect panniculus of an obese woman away from the surgical site during use. The lip is disposed on a proximal end of the retractor.

In any embodiment, at least two of the radially adjustable saddle-shaped retractors comprise an upwardly depending lip configured to deflect panniculus of an obese woman away from the surgical site during use.

In any embodiment, the upwardly depending lip extends to height of at least 2, 3, 4, 5, or 6 inches, for example 2-10, 2-8, 2-6, 2-4, 3-8, 3-6 or 3-4 inches above the patients abdomen when the retractor has engaged the incision. The length of the lip may be varied according to the patient. Thus, for obese patients with larger panniculus, a larger (or more rigid) deflecting lip may be employed.

In any embodiment, the lip is rigid.

In any embodiment, the lip is semi-rigid to allow a degree of deflection of the lip during use while keeping the panniculus away from the operational field.

In any embodiment, a side profile of the deflecting lip is s-shaped.

In any embodiment, the panniculus deflecting element is adjustably attached to the retractor and configured for positional adjustment relating to the retractor. For example, the lip may be hingedly attached to the retractor. The lip may be adjustable from a first configuration (e.g. generally parallel to a plane of the supporting ring) to a deployed panniculus deflecting configuration.

In any embodiment, the panniculus deflecting element is detachably attached to the retractor. This allow use of a modular system where the lip can be chosen according to the panniculus of the woman and attached to the retractors. Thus, the invention also relates to a system of the invention comprising a plurality of panniculus lips of differing shape and/or dimension configured for detachable attachment to a retractor.

In any embodiment, the panniculus deflecting element is shape adjustable. The element may include a spring to allow the element spring from one configuration (e.g. downwardly depending) to a second configuration (upwardly depending). The element may comprise a thin malleable metallic core, integrated into the element itself, which would allow a degree of user shaping. Other methods of incorporating shape-adjustability will be apparent to a person skilled in the art.

In any embodiment, the retractor comprises an upper panel, a lower panel, and a rear panel and is configured to cup a section of tissue.

In any embodiment, the retractor has a generally U-shaped profile.

In any embodiment, the panniculus deflecting lip is disposed on (or attachable to) a proximal end of the upper wall of the retractor.

In any embodiment, the rear wall has a convex curvature to conform to the curvature of an opened (caesarean) incision.

In any embodiment, the lower wall has a curved profile to match the curvature of an underside of the abdominal wall of a pregnant woman.

In any embodiment, the upper panel of the adjustable saddle-shaped retractors is splayed outwardly away from the incision.

In any embodiment, the upper panel of the retract has a generally trapezoid shape.

In any embodiment, when the retractor has a panniculus deflecting lip, the transition between the upper wall and the lip is a smooth curve.

In any embodiment, when the system comprises at least two retractors, the upper walls of the retractors are dimensioned to dovetail when placed side-by-side on the ring in a retracted position.

In any embodiment, the retractors are rigid.

In any embodiment, the retractors are semi-rigid.

In any embodiment, the retractors are sufficiently resiliently deformable so as to allow a user cup and clasp tissue with the retractor.

In any embodiment, the system is configured to allow circumferential adjustment of at least one of the retractors on the ring.

In one embodiment, the system comprises a coupling element configured for attachment to the ring at a plurality of different circumferential positions on the ring. The coupling element may include a part for coupling to the ring and a second part for coupling to the retractor.

In any embodiment, the coupling element is integrally formed with the retractor.

In any embodiment, the coupling element is configured for snap-fit coupling to the supporting ring.

In any embodiment, the retractor comprises a plurality of integral coupling element that are radially spaced apart to allow radial adjustment of the retractor on the ring.

In any embodiment, the supporting ring and saddle-shaped retractors are formed from polymer. In another embodiment, the ring and/or retractors are made from metal or composite materials.

In any embodiment, the supporting ring and retractors are single-use disposable parts. In another embodiment, the ring and/or retractors are re-usable.

In any embodiment, the first formation on the supporting ring is a projecting lug.

In any embodiment, the corresponding second formation on the retractor is a lug receiving slot.

In any embodiment, the retractor is radially adjustable and comprises a plurality of radially spaced apart second formations (e.g. radially spaced apart lug-receiving slots).

In any embodiment, the or each lug-receiving slot is a re-entrant slot. This means that the slot is dimensioned to receive the lug and then clamp the lug upon movement of the lug relative to the slot (generally transverse movement of the retractor relative to the lug).

In any embodiment, the or each lug-receiving slot comprises a radially inward slot portion dimensioned to receive the lug and a radially outward slot portion configured for snap-fit engagement with the lug.

In any embodiment, the lug comprises a stem part dimensioned for snap-fit engagement with the radially outward slot part and a head part that is oversized in relation to the radially outward slot part but dimensioned to fit comfortably through the radially inward slot part. The stem may have a circular or oval profile and may be conical or inwardly or outwardly tapering.

In any embodiment, the radially inward slot part is oversized relative to the head part of the lug allowing the lug to be easily received in the slot part.

In any embodiment, the radially inward slot part is dimensioned to receive the head part of the lug when the head part is misaligned with the radially inward slot by up to 10° in the yaw direction.

In any embodiment, the lug is generally T-shaped and comprises an elongated head part.

In any embodiment, the elongated head part is aligned with a circumference of the supporting ring.

In any embodiment, the plurality of radially spaced apart first formations are disposed in a proximal section of the upper wall of the retractor.

In any embodiment, one of the formations on the supporting ring is disposed on the supporting ring diametrically opposed to the non-adjustable saddle-shaped retractor.

In any embodiment, the supporting ring comprises two formations disposed on a side of the supporting ring opposite the fixed saddle-shaped retractor.

In any embodiment, the first formation on the supporting ring is a recess, for example a channel, and the corresponding second formation on the retractor is a recess or channel-engaging projection.

In any embodiment, the channel is at least partly recessed in the supporting ring.

In any embodiment, the channel is a radial channel and the channel engaging projection is a radially extending rail element disposed on an underside of the upper wall of the retractor and configured to engage (and typically interlock) with the channel typically allowing sliding radial movement of the rail in the channel.

In any embodiment, the rail is integrally formed with the retractor.

In any embodiment, the radial channel on the supporting ring has a longitudinal axis that extends radially inwardly and downwardly towards a plane of the supporting ring.

In any embodiment, the channel has an elliptical profile. Other profiles include circular or oval shaped.

In any embodiment, the rail element and radial channel are dimensioned for a tight but sliding fit such that pitching movement of the retractor relative to the supporting ring effects frictional locking of the rail element to the channel.

In any embodiment, the or each first formation on the supporting ring is integrally formed with the supporting ring.

In any embodiment, the or each formation on the supporting ring is detachably mountable to the supporting ring.

In any embodiment, the detachably mountable first formation comprises a body with a lower part having a channel configured for snap-fit engagement with the supporting ring and an upper part comprising a formation configured for engagement with a corresponding second formation on the retractor.

In any embodiment, the formation on the upper part of the body comprises a rail-engaging channel or a projection.

In any embodiment, the formation on the upper part of the body comprises a rail-engaging channel with an aperture configured to allow contact between the rail and the supporting ring.

In any embodiment, the body is configured to allow an upper part of the supporting ring project into the rail engaging channel. Contact between the rail and supporting ring can act as a frictional locking means to lock the retractor in position on the supporting ring.

In any embodiment, an underside of the rail element has a plurality of radially spaced apart teeth.

In any embodiment, a top surface of the supporting ring has an elongated circumferential grove configured to receive any one of the plurality of radially spaced apart teeth through the aperture when the body is engaged with the supporting ring and the rails of the retractor.

In any embodiment, the teeth and groove are configured for locking engagement when the retractor is in a first pitch orientation and disengagement when the retractor is in a second pitch orientation.

In any embodiment, the first pitch orientation is an inwardly pitched orientation.

In any embodiment, the teeth have a saw-tooth profile (flat or curved saw-tooth profile).

In any embodiment, each tooth extends laterally at least partly across the rail.

In any embodiment, the channel in the lower part of the body has an elliptical profile configured to allow a limited amount of rotation of the body on the supporting ring while preventing full rotation. Limited rotation may be for example 5 to 40°, 5 to 30° or 5 to 20° in a clockwise and/or anti-clockwise direction.

In any embodiment, the supporting ring is planar.

In any embodiment, the supporting ring is non-planar.

In any embodiment, the supporting ring curves upwardly away from the handle.

In any embodiment, the supporting ring has a first upwardly curved inflection and a second downwardly curved inflection.

In any embodiment, the system comprises a panniculus deflection element configured for retrofitting to the supporting ring.

In any embodiment, the panniculus deflecting element comprises an elongated curved panel and a connection means for connecting the panel to the supporting ring in a panniculus deflection orientation.

In any embodiment, the curvature of the panel follows the curvature of the supporting ring.

In any embodiment, the connection means comprises a plurality of radial arms configured for snap-fit engagement with the supporting ring.

In any embodiment, the elongated curved panel has a width that is at least 50%, 60%, 70%, 80% or 90% of the widest dimension of the supporting ring. When the ring is circular, the widest dimension will be the diameter of the ring.

In any embodiment, the retractor comprises a functional material.

In any embodiment, the retractor comprises an anti-microbial material.

In any embodiment, the retractor is formed from a transparent material.

In any embodiment, an external surface of the paddle, especially the inflection curve joining the real wall with the upper and/or lower walls, has a smooth surface.

In any embodiment, an external surface of the paddle, especially the inflection curves joining the real wall with the upper and lower walls, comprises a hydrophilic surface. A hydrophilic coating is a very thin and transparent coating, which is typically used on catheters. A typical arrangement would be to 'dip' the article into a container which holds the liquid hydrophilic coating. When the article is removed from the container, it is 'wet' with the hydrophilic coating and typically requires 'curing' to bind the coating to the surface of the article. This curing can be either heat, in an oven, or UV curing in a specialised UV chamber. The finished coating is dry to touch, but when it gets wet, it absorbs water in the region of 300 to 400% its own weight, which makes the surface feel very slippery, like a bar of soap.

In any embodiment, an internal surface of the paddle, especially the rear wall and inflection curves joining the real wall with the upper and lower walls, comprises a roughened surface which optionally comprises indentations or projections on the surface.

In any embodiment, the lower wall is inclined slightly upwardly towards the upper wall, for example by up to 10°, for example 2-10°, 2-7°, or about 5°.

In any embodiment, the rear wall is dimensioned according to the thickness of the abdominal wall of the woman. The rear wall typically has a height of 2-10 cm, and 5-10 cm or 5-7 cm for an obese woman and 2-3 cm for a non-obese woman.

In any embodiment, the transition from the upper wall to the rear wall and/or the transition from the rear wall to the lower wall is curved.

In any embodiment, the transition from the upper wall to the rear wall curves upwardly and around to the rear wall to provide a skin stress-relieving pocket.

In any embodiment, the edges of the rear wall and/or lower wall have a smooth atraumatic profile.

In any embodiment, the edges of the rear wall and/or lower wall comprises a soft and flexible beading, coating or edging which is optionally formed from a soft elastomer or silicone material.

In any embodiment, the soft flexible beading/coating or edging is adhered to the edge of the retractor by an over-moulding process. Other methods include adhesive bonding or other joining processes, such as laser welding or ultrasonic joining.

In any embodiment, the supporting ring is configured to emit light. Thus, it may incorporate lights and a battery, or it may incorporate chemicals that upon actuation react to emit light, for example luminescent light.

The invention also relates to a surgical access system according to the invention for use in a method of performing surgery on a subject, in which the system is used to retract tissue and hold the retracted tissue in a retracted position. The subject may be a man or a woman. The surgery may be abdominal surgery. The abdominal surgery may be a Caesarean section procedure on a pregnant woman. The pregnant woman may be obese, in which the method may include a step of deflecting the panniculus of the pregnant obese woman away from the surgical site with the panniculus deflecting lip.

In another aspect, the invention provides a method of facilitating access to a neonate through a caesarean incision in the woman's abdomen by opening the incision, comprising the steps of:
  providing a supporting ring dimensioned to allow delivery of a neonate through the ring and comprising a non-adjustable pelvic-region retractor and handle fixed to the supporting ring;
  articulating the supporting ring to insert the non-adjustable pelvic-region retractor into the incision to cover and hold back the woman's bladder with the supporting ring disposed over the woman's abdomen;

inserting a first adjustable saddle-shaped retractor into the incision to cup a first section of abdominal tissue on an abdominal side of the incision;

attaching the first adjustable saddle-shaped retractor to the supporting ring while it is cupping the first section of abdominal tissue at a first position spaced apart from the non-adjustable pelvic-region retractor to anchor the supporting ring to the woman and partially open the incision.

inserting a second adjustable saddle-shaped retractor into the incision to cup a second section of abdominal tissue; and attaching the second adjustable saddle-shaped retractor to the supporting ring while it is cupping the second section of tissue at a second position on the supporting ring spaced apart from the non-adjustable pelvic-region retractor to further open the incision.

In any embodiment, the first adjustable saddle-shaped retractor is attached to the supporting ring at a position on the ring diametrically opposite the non-adjustable pelvic-region retractor.

In any embodiment, the method includes the steps of:

inserting a third adjustable saddle-shaped retractor into the incision to cup a third section of abdominal tissue; and attaching the third adjustable saddle-shaped retractor to the supporting ring while it is cupping the third section of tissue at a third position spaced apart from the non-adjustable pelvic-region retractor to further open the incision, wherein the first adjustable saddle-shaped retractor is attached to the supporting ring at a position on the ring diametrically opposite the non-adjustable pelvic-region retractor, and the second and third adjustable saddle-shaped retractors are attached to the supporting ring at positions flanking and adjacent to the first adjustable saddle-shaped retractor.

In any embodiment, coupling elements are employed to attach the first saddle-shaped retractor to the supporting ring in a tissue-retracting position, wherein the coupling elements are configured to allow the retractor pitch and/or yaw relative to the supporting ring when the retractor is fitted to the ring in a tissue retracting position, wherein the method comprises the pitch and/or yaw of the first saddle shaped retractor being adjusted during the delivery of the neonate.

In any embodiment, at least one of adjustable saddle-shaped retractor comprises an upwardly depending lip configured to deflect panniculus of an obese woman away from the surgical site during use, the method comprising a step of the panniculus deflecting lip deflecting the panniculus of the woman away from the surgical site while the adjustable saddle-shaped retractors hold the incision in an open configuration.

In any embodiment, self-locking coupling elements are employed to attach the adjustable saddle-shaped retractor to the supporting ring in a tissue-retracting position, in which the self-locking coupling elements are actuable to lock the retractor to the supporting ring in response to radially inward forces exerted on the retractor by the abdominal tissue when the retractor is in a tissue retracting position, in which the method comprises manually attaching the adjustable saddle-shaped retractor to the supporting ring in a tissue retraction position by the self-locking coupling elements and releasing the retractors wherein the retractor is pulled radially inwardly to actuate the self-locking coupling elements.

In any embodiment, self-locking coupling elements comprise a projection on the supporting ring and a projection-receiving re-entrant slot on the retractor, in which the re-entrant slot is configured to receive the projection and lock the projection to the slot upon radial inward movement of the slot relative to the projection, wherein the method comprises the steps of engaging the re-entrant slot and projection, and releasing the retractor wherein the retractor is pulled radially inwardly to lock the projection to the re-entrant slot.

In any embodiment, coupling elements are employed to attach the saddle-shaped retractor to the supporting ring in a tissue-retracting position, in which the coupling elements comprise a radially extending rail disposed on the retractor and a channel on the supporting ring configured to receive the rail in a sliding engagement, wherein the method comprises cupping a section of tissue with the retractor, engaging the rail of the retractor with the channel of the supporting ring, retracting the retractor by sliding the rail radially outwardly in the channel, and locking the rail to the channel in the radially outward position.

In any embodiment, the rail and channel are configured for friction interlocking when the retractor is disposed relative to the ring at a first pitch and unlocking when the retractor is disposed relative to the ring at a second pitch, wherein the method comprises orienting the retractor relative to the supporting ring at the second pitch, retracting the retractor while it is held at the second pitch, and then adjusting the pitch of the retractor relative the supporting ring to the first pitch to lock the retractor to the ring, and releasing the retractor.

In any embodiment, coupling elements are employed to attach the saddle-shaped retractor to the supporting ring in a tissue-retracting position, in which the coupling elements comprise a formation on the retractor configured to snap-fit directly to an external aspect of the ring, wherein the method comprises a step of retracting the retractor until the formation is facing an external aspect of the ring and moving the formation partially radially inward to engage the external aspect of the ring.

In any embodiment, coupling elements are employed to attach the saddle-shaped retractor to the supporting ring in a tissue-retracting position, in which the coupling elements comprise a first formation on the supporting ring and a second corresponding formation on the adjustable saddle-shaped retractor configured for engagement with the first formation, wherein the method comprises attaching the saddle-shaped retractor to the supporting ring by engaging the first formation with the corresponding second formation.

In any embodiment, the adjustable saddle-shaped retractor comprises a plurality of second corresponding formations radially spaced apart on the retractor, wherein the method comprises:

inserting the adjustable saddle-shaped retractor into the incision to cup a first section of abdominal tissue on an abdominal side of the incision;

attaching the adjustable saddle-shaped retractor to the supporting ring by engaging the first formation with one of the second corresponding formation;

holding the retractor attached to the ring for a period of time;

detaching the retractor from the ring; and attaching the retractor to the supporting ring in a second retraction position by engaging the first formation with another of the second corresponding formations to further retract the first section of tissue.

In any embodiment, the method includes a step of adjusting the radial position of the adjustable saddle-shaped retractor to a less retracted position after the neonate has been delivered.

In another aspect, the invention provides a method of facilitating access to a surgical site through an incision in a patient's body by opening the incision, comprising the steps of:
inserting a first adjustable saddle-shaped retractor into the incision to cup a first section of tissue;
attaching the first adjustable saddle-shaped retractor to a supporting ring while it is cupping the first section of tissue;
inserting a second adjustable saddle-shaped retractor into the incision to cup a second section of tissue; and
attaching the second tissue retracting paddle to the supporting ring while it is cupping the second section of tissue to hold open the incision.

In any embodiment, the incision is a caesarean incision and the tissue comprises abdominal tissue, and in which the supporting ring is dimensioned to allow delivery of a neonate through the ring.

In any embodiment, the method may employ a system of the invention.

In any embodiment, the supporting ring comprises a saddle-shaped retractor fixed to (e.g. integrally formed with) the ring, in which the method comprises an initial step of inserting the fixed saddle-shaped retractor into the incision to cup a section of abdominal tissue. In one embodiment, the fixed retractor is a pelvic-region retractor and the method comprises inserting the retractor into the incision to cup or abut a section of abdominal tissue above the subject's bladder and cover and hold back the bladder.

In any embodiment, the method comprises a further step of adjusting the radial position of the first or second tissue retracting retractor with respect to the supporting ring optionally while it is attached to the supporting ring.

In any embodiment, the retractor comprises a plurality of radially spaced apart formations in which each formation is configured to attach to the supporting ring. The formation may be configured to attach directly to the ring, to a connector which is detachably connected to the ring, or to a corresponding formation integrally formed on the ring (e.g. a projection such as a lug).

In any embodiment, the method comprises the steps of:
cupping a first section of tissue with the retractor;
attaching the retractor to the supporting ring in a first retraction position using a first of the radially spaced apart formations to partially retract the first section of tissue;
holding the retractor attached to the ring in the first retraction position;
detaching the retractor from the ring;
attaching the retractor to the supporting ring in a second retraction position using a second of the radially spaced apart formations to further retract the first section of tissue;
holding the retractor attached to the ring in the second retraction position; and
optionally, repeating the detaching, attaching and holding step to further retract the section of tissue.

In any embodiment, the formations on the retractor comprise formations configured to snap-fit to the ring or an intermediate connector.

In any embodiment, the formation on the retractor is a slot and the supporting ring comprises a lug, and the method comprises bringing the slot and lug into engagement.

In any embodiment, the slot is a re-entrant slot configured to receive the lug and lock the lug to the slot upon radial inward movement of the slot relative to the lug, wherein the method comprises the steps of engaging the re-entrant slot and lug, and allowing the retractor be pulled radially inwardly by forces exerted by the opened incision to lock the slot to the lug.

In any embodiment, the formation on the retractor is an integrally formed radially extending rail and the ring comprises a channel configured to receive the rail in a sliding engagement, wherein the method comprises cupping a section of tissue with the retractor, engaging the rail of the retractor with the channel of the supporting ring, and retracting the retractor by sliding the rail radially outwardly in the channel, and locking the rail to the channel in the radially outward position.

In any embodiment, the rail and channel are configured for friction interlocking when the retractor is disposed relative to the ring at a first pitch and unlocking when the retractor is disposed relative to the ring at a second pitch, wherein the method comprises orienting the retractor relative to the supporting ring at the second pitch, retracting the retractor while it is held at the second pitch, and then adjusting the pitch of the retractor relative the supporting ring to the first pitch to lock the retractor to the ring, and releasing the retractor.

In any embodiment, the formation on the retractor is configured to snap-fit directly to an external aspect of the ring, wherein the method comprises a step of retracting the retractor until the formation is facing an external aspect of the ring and moving the formation partially radially inward to engage the external aspect of the ring.

In any embodiment, the method comprises a further step of adjusting the circumferential position of the first or second tissue retracting paddle with respect to the supporting ring while it is attached to the supporting ring.

In any embodiment, the method comprises additional steps of inserting a third adjustable saddle-shaped retractor into the incision and cupping a third section of abdominal tissue with the retractor, and attaching the third retractor to the supporting ring to further open the incision.

In any embodiment, the method comprises a step of adjusting a height of at least one of the adjustable saddle shaped retractors prior to or after it has cupped a section of tissue.

In another aspect, the invention provides a method of facilitating access to a woman's womb through a caesarean incision in the woman's abdomen by opening the incision, comprising the steps of:
providing a supporting ring dimensioned to allow delivery of a neonate through the ring and comprising a saddle-shaped pelvic-region retractor and handle fixed to the supporting ring;
inserting the fixed saddle-shaped pelvic-region retractor into the incision to cup a first section of abdominal tissue over the woman's bladder;
inserting a first adjustable saddle-shaped retractor into the incision to cup a second section of abdominal tissue;
attaching the first adjustable saddle-shaped retractor to the supporting ring at a position spaced apart from the fixed saddle-shaped pelvic-region retractor to open the incision;
inserting a second adjustable saddle-shaped retractor into the incision to cup a third section of abdominal tissue with the retractor; and
attaching the second adjustable tissue retracting paddle to the supporting ring to further open the incision.

In any embodiment, the method comprises additional steps of inserting a third adjustable saddle-shaped retractor into the incision and cupping a fourth section of abdominal tissue with the retractor and attaching the third adjustable saddle-shaped retractor to the supporting ring to further open the incision.

In any embodiment, the method comprises a further step of adjusting the radial position of at least one of the adjustable saddle-shaped retractors with respect to the supporting ring while it is attached to the supporting ring.

In any embodiment, the supporting ring comprises a coupling element that is configured to allow radial adjustment of the adjustable retractor on the supporting ring from a first retraction position to a second retraction position.

In any embodiment, the adjustable retractor comprises a radial slot, and the coupling element comprises a lug configured for sliding engagement in the slot and a brake that is actuatable to lock the adjustable tissue retracting paddle to the coupling element. In one embodiment, the brake is self-locking.

In any embodiment, the method comprises a further step of adjusting the circumferential position of at least one of the adjustable saddle-shaped retractors on the supporting ring, typically while it is attached to the supporting ring.

In any embodiment, the coupling element is configured for movement along the supporting ring from a first circumferential position to a second circumferential position, wherein the method comprises a step of circumferential adjustment of the retractor on the supporting ring.

In any embodiment, the coupling element comprises a carriage that is moveable along the ring and comprises brake means for fixing the carriage in a position along the ring.

In any embodiment, the method comprises a step of adjusting the height of the adjustable saddle-shaped retractor prior to or after it cups the tissue.

In any embodiment, an upper wall of at least one of the adjustable saddle-shaped retractors comprises an upwardly depending panniculus deflecting lip, wherein the upwardly depending lip deflects the woman's panniculus away from the incision when it is attached to the supporting ring.

Other aspects and preferred embodiments of the invention are defined and described in the other claims set out below.

BRIEF DESCRIPTION OF THE FIGURES

FIGS. 11 and 12 are perspective and top view from above of a section of the supporting ring showing the three first formations (central and flanking T-shaped lugs) integrally formed with the ring at 0°, 48° and 312° (in which the fixed retractor is positioned on the ring at 180°). FIG. 12 illustrates how the T-bar head of the lug is aligned with the ring.

FIG. 13 is a perspective view from below of the supporting ring and a radially adjustable retractor positioned adjacent the ring with the second slot aligned with the central T-shaped lug and the retractor straddling the supporting ring with the rear wall of the retractor projecting downwardly into the supporting ring.

FIG. 14 is a perspective view from above of the supporting ring showing a rear side of the fixed retractor and the handle.

FIGS. 15, 16 and 17 illustrate the configuration of the re-entrant slot on the retractor and how it engages with the T-shaped lug. FIG. 15 shows a radially adjustable retractor engaging with the supporting ring with the T-shaped lug of the supporting ring received in the radially inward part of the slot. FIG. 17 is a plan view from above of the t-shape head of the lug received in the oversized part of the slot. FIG. 16 shows the retractor after being moved radially inwards relative to the supporting ring and the stem of the lug friction locking to the smaller radially outward slot part.

FIG. 20 is a plan view from above of two radially adjustable retractors attached to a supporting ring, illustrating how the coupling elements allow yaw movement of the retractors when they are locked to the ring. It will be appreciated that the forces acting on the retractors when they are in a tissue retracting position is a radially inwards force, which serves to lock the lug in the radially outward part of the re-entrant slot while allowing side to side yaw movement of the retractors relative to the supporting ring.

FIGS. 22 and 23 are perspective views of radially and circumferentially adjustable retractors having a series of radially spaced apart second formations integrally formed on an underside of the upper panel of the retractor that are configured for snap-fit engagement with the supporting ring. A proximal end of the upper panel includes an upwardly depending panniculus deflecting lip that has a height approximately the same as the height of the rear panel of the retractor.

FIG. 27 is a plan view from above of the retractors of FIGS. 24 and 25 showing how the coupling elements on the underside of the retractor allow both circumferential and radial adjustment of the retractors on the ring.

FIGS. 30 and 31 illustrate another embodiment of the system of the invention with a supporting ring with a fixed saddle shaped retractor, three radially adjustable retractors (one diametrically opposed to the fixed retractor), and two radially and circumferentially adjustable retractors flanking the fixed retractor.

FIG. 37 is an illustration of the use of one embodiment of the surgical access system of the invention in a caesarean section procedure, in which:

FIG. 38 shows a radially adjustable retractor according to an alternative embodiment of the invention.

FIG. 39 is a perspective view from below of the retractor of FIG. 38 attached to a supporting ring that includes first formations (recessed radial channels) configured for receipt of a corresponding second formation (rail element) on an underside of the upper panel of the retractor.

FIG. 40 is a perspective view from above of the system of FIG. 39.

FIGS. 46 and 47 are perspective views of alternative first formations (detachable connectors) configured to couple the retractor of FIG. 38 to a supporting ring. The connectors have a body with a ring-receiving channel in a lower part of the body and a rail-engaging channel formed in an upper part of the body that is generally orthogonal to the ring-receiving channel so that an axis of the rail-engaging channel projects radially inwardly. The ring-receiving channel is dimensioned to snap fit to the supporting ring. The rail engaging channel is dimensioned to engage with the rail of the retractor in a sliding relationship.

FIGS. 48 and 49 are perspective views of alternative first formations (detachable connectors) configured to couple the retractor of FIG. 38 to a supporting ring. The connectors are similar to the connectors of FIGS. 46 and 47 except that the rail engaging slot is recessed into the body and communicates with the ring-engaging slot that in use allows a top part of the connecting ring protrude into the rail-engaging slot. This allows the rail and supporting ring contact each other to function as a friction locking mechanism to lock the rail to the supporting ring.

FIG. 50 is a side elevation perspective view of a supporting ring having a detachable connector of FIGS. 46 and 47 snap-fitted to the ring and a radially adjustable retractor of FIG. 38 approaching the detachable connector. This shows how the use of this connector allow both radial and circumferential adjustment of the position of the retractor on the connecting ring.

In FIGS. 54 and 55 the connector is pitched outwardly and inwardly causing frictional locking between the ring and the channel at defined friction points.

FIGS. 61 to 63 are views of the system to FIG. 59 showing how the teeth on the rail of the retractor engage and lock with a groove formed on a top of the supporting ring when the connector is attached to the rail and the supporting ring.

In FIG. 64 the connector is rotated (i.e. pitched inwardly) relative to the ring and the teeth do not engage. In FIG. 65, the connector is not rotated (no pitch) and a tooth on the rail engages the groove on the supporting ring, resulting in the rail, connector and supporting ring being locked in position. The lock may be released by adjusting the pitch of the retractor relative to the ring.

FIG. 68 is a view of a system of the invention incorporating a detachable connector of FIGS. 66 and 67 and showing how the detachable connector is circumferentially adjustable around the ring and how the connector allows radial adjustment of the retractor relative to the ring.

FIG. 69 is a perspective view of a radially adjustable retractor attached to a supporting ring with the detachable connecter of FIGS. 66 and 67, where the retractor is attached to the T-shaped lug of the connector via its radially innermost slot and therefore at maximum retraction.

FIGS. 78 and 79 are elevational views of a system according to an alternative embodiment of the invention that incorporates a detachable elongated panniculus deflecting lip configured for attachment to the ring outside and curved around a section of the ring opposite to the fixed retractor.

FIGS. 80 and 81 are perspective views of a radially adjustable retractor without panniculus deflecting lip and for use with a system comprising a detachable panniculus deflecting lip.

FIG. 82 is a perspective view of the system of FIG. 79 with the radially adjustable paddle of FIG. 80 attached to the ring by an integrally formed T-shaped lug.

FIGS. 85 and 86 are perspective views of a radially adjustable retractor with a smooth hydrophilic surface configured to absorb water making the surface slippery to aid passage of a neonate during delivery.

FIG. 89 is a side elevational view of a retractor showing how the lower panel tapers upwardly away from the incision which assists the retractor grip or clasp abdominal tissue during use.

FIG. 90 shows how the height of the rear panel of the retractor can be varied to take account of patients having abdominal tissue of different thickness.

FIG. 98 is a side elevational view of the retractor of FIG. 96.

FIG. 99 is a side elevational view of a retractor without the soft elastomeric or silicone edging.

FIGS. 104 and 105 are perspective views of the retractor of FIG. 103 with the panniculus deflecting lip being formed into two different shapes.

FIGS. 106 and 107 are perspective views of the retractor of FIG. 103 prior to attachment to a supporting ring.

FIG. 110 is a perspective view of a system of the invention with a number of paddles each having an adjustable panniculus deflecting lip which is deployed upwardly in three of the retractors and folded down out of the way in two of the retractors.

FIG. 111 illustrates the use of a system of the invention to hold back an obese woman's panniculus during a Caesarean section procedure.

DETAILED DESCRIPTION OF THE INVENTION

Figure 1A:
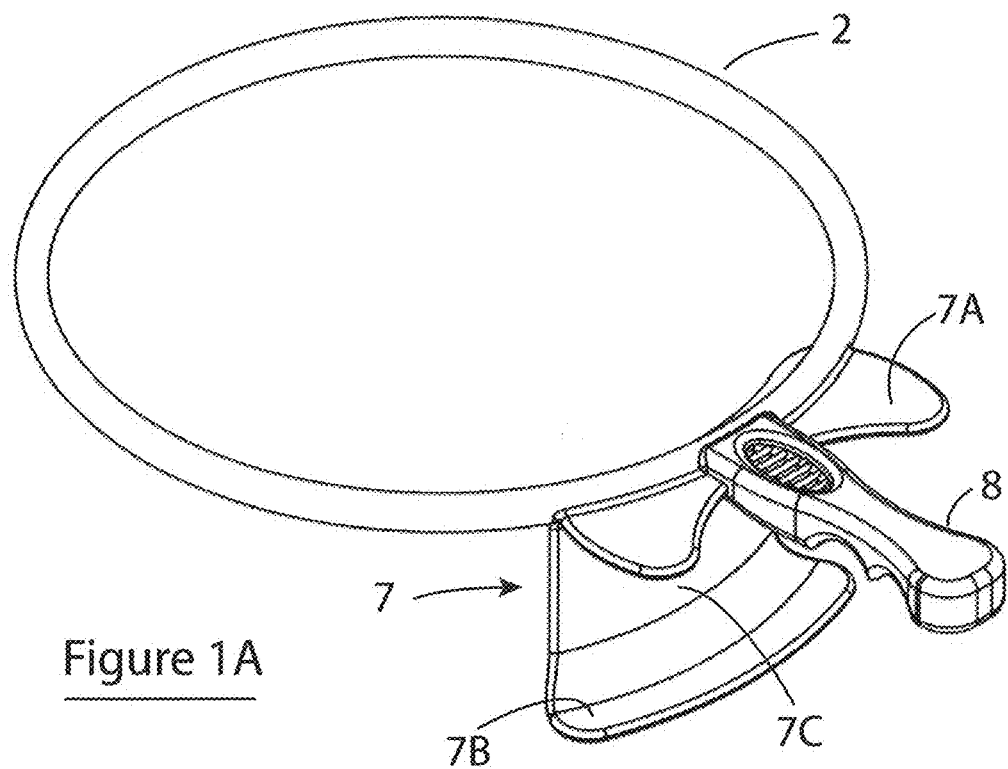
FIGS. 1A and 1B are perspective views of a supporting ring forming part of a surgical access system according to one embodiment of the invention and having a fixed saddle-shaped retractor.

All publications, patents, patent applications and other references mentioned herein are hereby incorporated by reference in their entireties for all purposes as if each individual publication, patent or patent application were specifically and individually indicated to be incorporated by reference and the content thereof recited in full.

Definitions and General Preferences

Where used herein and unless specifically indicated otherwise, the following terms are intended to have the following meanings in addition to any broader (or narrower) meanings the terms might enjoy in the art:

Unless otherwise required by context, the use herein of the singular is to be read to include the plural and vice versa. The term "a" or "an" used in relation to an entity is to be read to refer to one or more of that entity. As such, the terms "a" (or "an"), "one or more," and "at least one" are used interchangeably herein.

As used herein, the term "comprise," or variations thereof such as "comprises" or "comprising," are to be read to indicate the inclusion of any recited integer (e.g. a feature, element, characteristic, property, method/process step or limitation) or group of integers (e.g. features, element, characteristics, properties, method/process steps or limitations) but not the exclusion of any other integer or group of integers. Thus, as used herein the term "comprising" is inclusive or open-ended and does not exclude additional, unrecited integers or method/process steps.

As used herein, the term "disease" is used to define any abnormal condition that impairs physiological function and is associated with specific symptoms. The term is used broadly to encompass any disorder, illness, abnormality, pathology, sickness, condition or syndrome in which physiological function is impaired irrespective of the nature of the aetiology (or indeed whether the aetiological basis for the disease is established). It therefore encompasses conditions arising from infection, trauma, injury, surgery, radiological ablation, age, poisoning or nutritional deficiencies.

As used herein, the term "treatment" or "treating" refers to an intervention (e.g. the administration of an agent to a subject) which cures, ameliorates or lessens the symptoms of a disease or removes (or lessens the impact of) its cause(s) (for example, the reduction in accumulation of pathological levels of lysosomal enzymes). In this case, the term is used synonymously with the term "therapy".

Additionally, the terms "treatment" or "treating" refers to an intervention (e.g. the administration of an agent to a subject) which prevents or delays the onset or progression of a disease or reduces (or eradicates) its incidence within a treated population. In this case, the term treatment is used synonymously with the term "prophylaxis".

As used herein, an effective amount or a therapeutically effective amount of an agent defines an amount that can be administered to a subject without excessive toxicity, irritation, allergic response, or other problem or complication, commensurate with a reasonable benefit/risk ratio, but one that is sufficient to provide the desired effect, e.g. the treatment or prophylaxis manifested by a permanent or temporary improvement in the subject's condition. The amount will vary from subject to subject, depending on the age and general condition of the individual, mode of administration and other factors. Thus, while it is not possible to specify an exact effective amount, those skilled in the art will be able to determine an appropriate "effective" amount in any individual case using routine experimentation and background general knowledge. A therapeutic result in this context includes eradication or lessening of symptoms, reduced pain or discomfort, prolonged survival, improved mobility and other markers of clinical improvement. A therapeutic result need not be a complete cure. Improvement may be observed in biological/molecular markers, clinical or observational improvements. In a preferred embodiment, the methods of the invention are applicable to humans, large racing animals (horses, camels, dogs), and domestic companion animals (cats and dogs).

In the context of treatment and effective amounts as defined above, the term subject (which is to be read to include "individual", "animal", "patient" or "mammal" where context permits) defines any subject, particularly a mammalian subject, for whom treatment is indicated. Mammalian subjects include, but are not limited to, humans, domestic animals, farm animals, zoo animals, sport animals, pet animals such as dogs, cats, guinea pigs, rabbits, rats, mice, horses, camels, bison, cattle, cows; primates such as apes, monkeys, orangutans, and chimpanzees; canids such as dogs and wolves; felids such as cats, lions, and tigers; equids such as horses, donkeys, and zebras; food animals such as cows, pigs, and sheep; ungulates such as deer and giraffes; and rodents such as mice, rats, hamsters and guinea pigs. In preferred embodiments, the subject is a human. As used herein, the term "equine" refers to mammals of the family Equidae, which includes horses, donkeys, asses, kiang and zebra. The system and method of the invention is primarily for use in human surgery but can be easily adapted for use with large mammals, such as equine, bovine, supine, ovine and porcine mammals.

"Supporting ring" refers to a supporting structure in the form of a ring, generally a closed ring, upon which tissue retractors can be attached and retained in a tissue-retracting position. The ring is generally circular, but may also be oval-shaped, elliptical or relux triangle shaped. It is generally dimensioned to be approximately the same size or slightly larger than the desired size of the opened incision. When the system is for use in a caesarean section procedure, the ring is dimensioned to allow delivery of a new-born baby through the ring and is generally circular or oval shaped. The ring may be curved (with a single inflection or multiple inflection points). The ring may also have a round cross-section or an elliptical cross-section. The latter has been found to be useful in the context of engaging and locking a connecting element to the ring, as the connecting element may be provided with a channel configured for snap-fit engagement with the ring where the channel has a profile providing limited clearance between the channel and the ring so as to allow limited (but not full) rotational movement of the coupling element on the ring, for example rotation of up to about +/−20° or 30°. Limited rotational movement allows the retractor to pitch inwardly and/or outwardly.

"Saddle-shaped retractor" or "retractor for cupping tissue" refers to a tissue retracting paddle that is shaped to cup a section of an incision in a patient's body in a manner similar to a human hand, and generally has an upper panel, lower panel and rear panel typically with a U-shaped profile. The distance between the upper and lower panels is referred to as the "height", and the length of the rear panel in contact with the incision is referred to herein as the "width". The rear panel may have a convex profile, to match the curvature of an opened incision. The retractor may be configured for height adjustment. In one embodiment, a proximal part of an upper panel of the retractor comprises an upwardly depending lip configured to deflect a patient's panniculus away from the incision when the retractor is attached to the supporting ring, especially deflect panniculus of an obese patient. This is especially suitable for use with abdominal incisions, and in particular caesarean sections in obese women (for example having a BMI greater than 30 or 35). The panniculus deflecting lip may have a height that is 0.5 to 1.5 times the height of the rear panel. The panniculus deflecting lip may have a s-shaped profile with a free end curving radially outwardly. The retractor may incorporate a degree of resilient deformability to allow a user clasp tissue when held in the hand. The upper panel of the retractor is generally splayed outwardly in a radial outward direction (this means that it is wider at a proximal end than at a distal end). The transition from the upper panel to the panniculus deflecting lip is generally curved. The transition from the upper panel to the rear panel is generally curved. The transition from the rear panel to the lower panel is generally curved. The upper panel is generally longer than the lower panel in a radial direction. The panels generally have smooth atraumatic edges and corners. An external surface of the rear and/or lower panels may comprise a hydrophilic material to make them slippery. An internal surface of the rear or lower panels may comprise a roughened surface to aid gripping tissue, which may be provided by surface treatment or integrally formed projections or indentations. As described elsewhere, the rear wall is ideally curved to follow the curvature of the opened incision. The lower wall is also ideally curved to follow the curvature presented by an internal surface of abdominal tissue.

Figure 19:
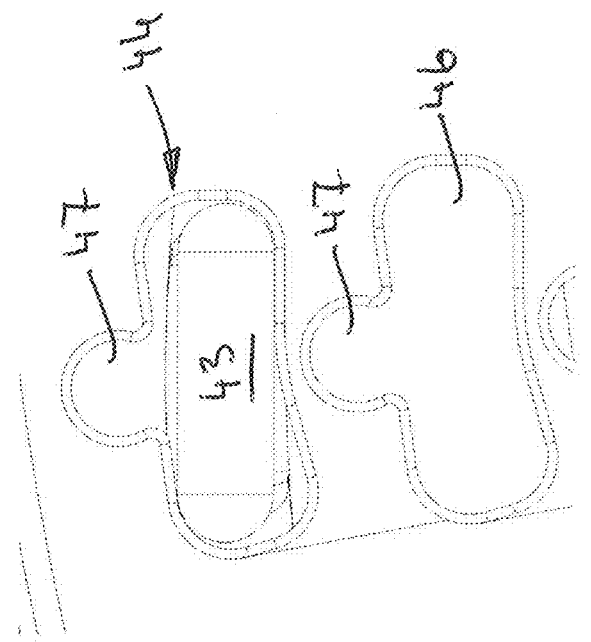
FIGS. 18 and 19 are plan view from above showing the lug engaging with the re-entrant slot, showing how the radially outward part of the slot is oversized to accommodate and tolerate a ±8° of user misalignment, with respect to the T-shaped head of the lug which facilitates the alignment of the lug and the slot in the pressurised environment of a surgical procedure.
Figure 18:
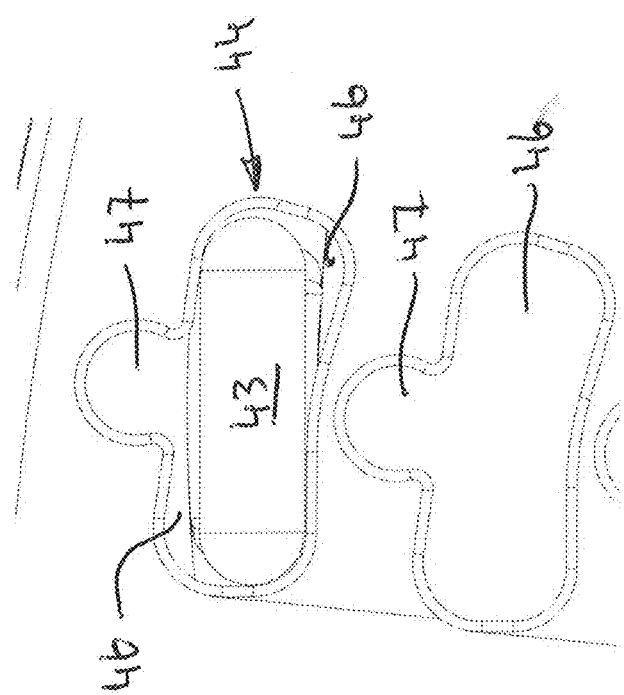
Figure 26:
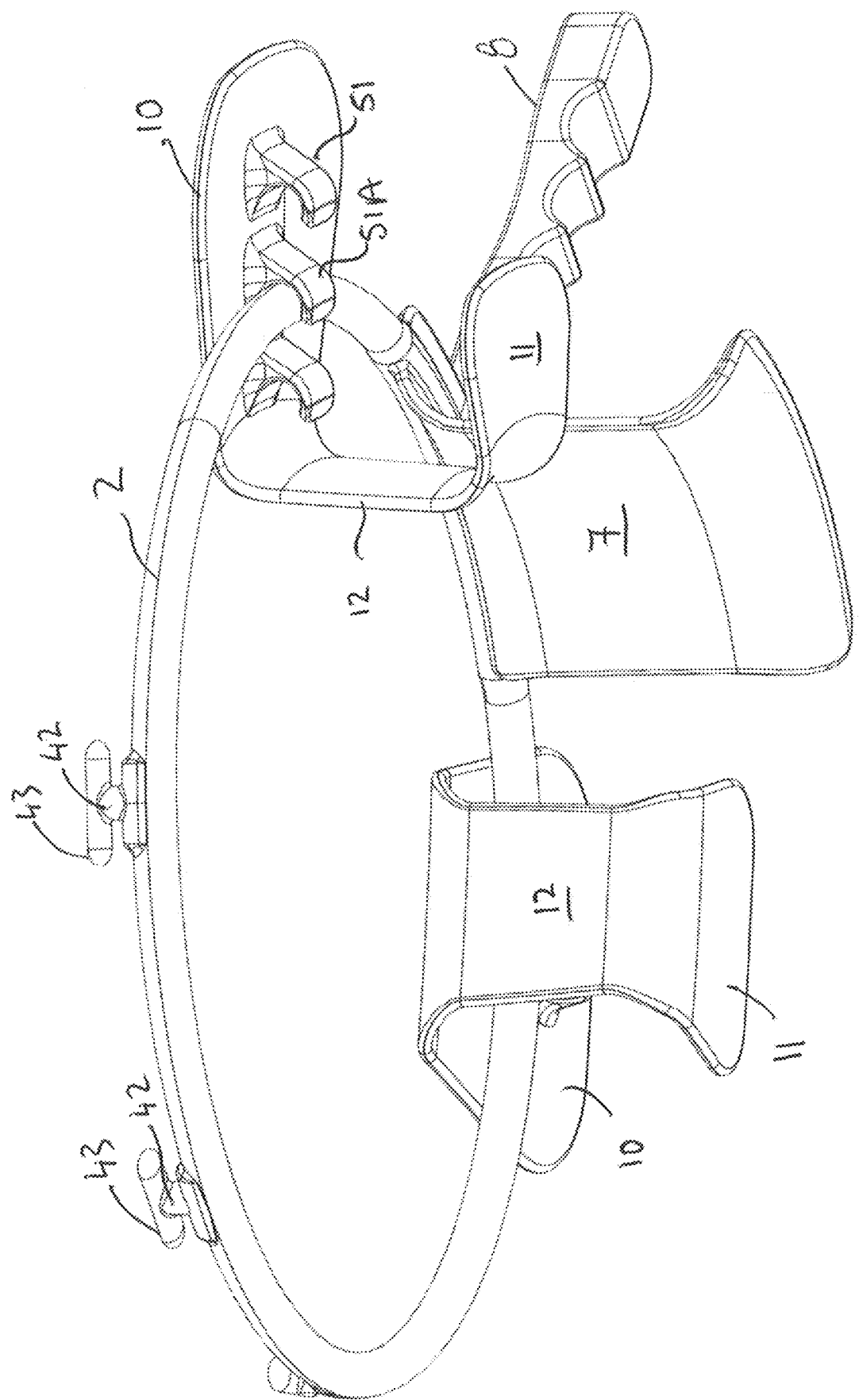
FIG. 26 is a perspective view from below of the retractors of FIGS. 24 and 25 attached to a supporting ring on each side of the fixed retractor.
Figure 41:
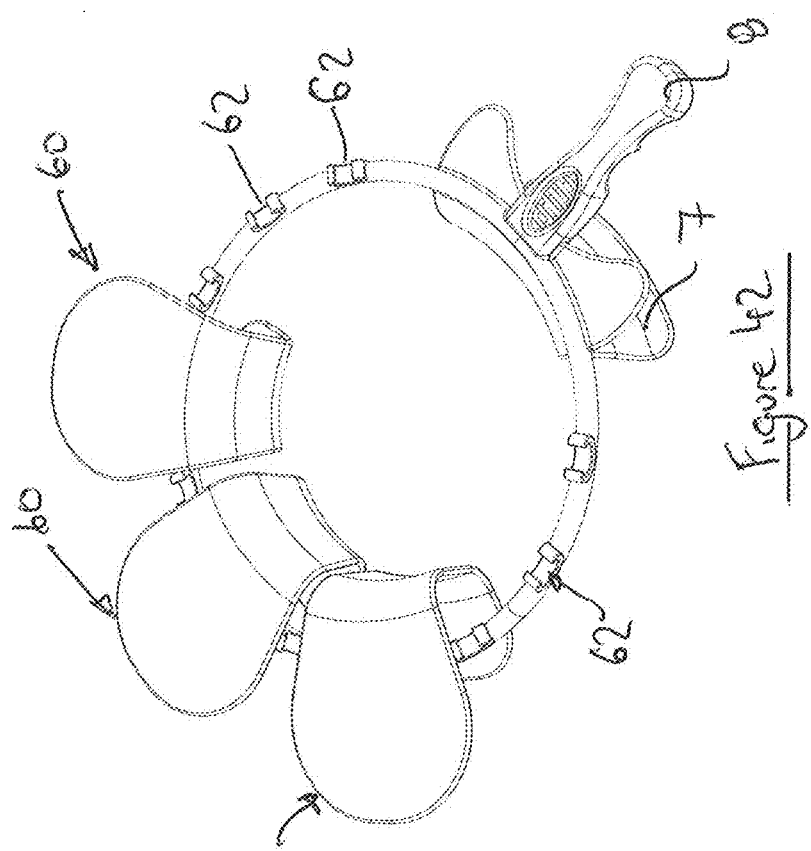
FIGS. 41 and 42 are perspective view from below (FIG. 41) and above (FIG. 42) of the system of FIG. 39 and including two additional radially adjustable retractors of FIG. 38 attached to the supporting ring at positions flanking the first retractor.
Figure 65:
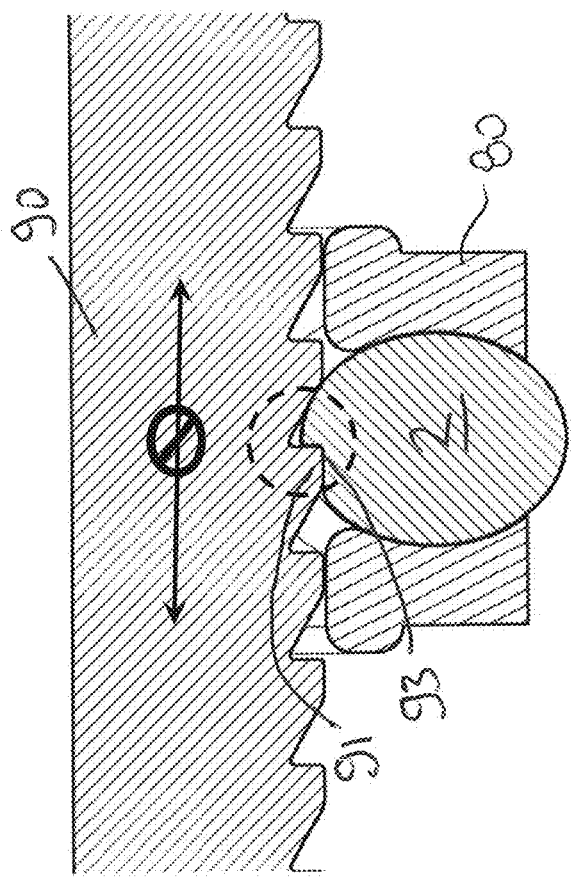
FIGS. 64 and 65 are sectional views showing the connector coupled to the supporting ring and the rail.
Figure 64:
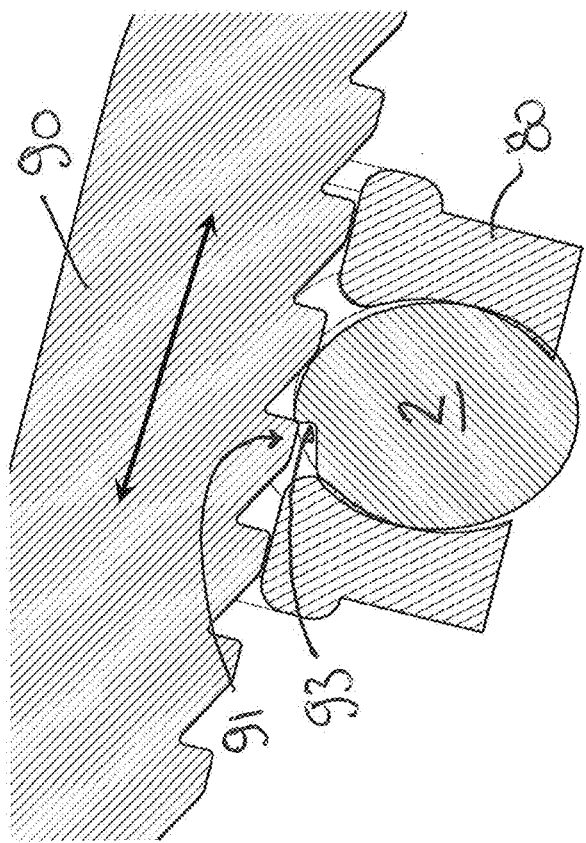

"Retro-fitting" as applied to the retractor means that the retractor is separate from the supporting ring and designed to be easily attached to the supporting ring during a surgical procedure while in a tissue-retracting position, typically by means of a coupling (connecting) element. Various coupling elements for attaching a retractor to the supporting ring are described herein, including the use of coupling elements having a lug configured to slidably engage in a slot in the retractor. In one embodiment, the coupling element comprises an element configured to snap-fit to the supporting ring. Embodiments described herein include carriage-like coupling elements (e.g. detachable connectors) configured for snap-fit coupling with the supporting ring at numerous positions along the ring. In one embodiment, the carriage is configured to allow circumferential movement of the carriage on the ring, while preventing or inhibiting rotational movement of the carriage on the ring. In other embodiment, the retractor includes in integral coupling element configured for direct engagement with the supporting ring, for example a groove dimensioned and position to snap-fit to the supporting ring. A plurality of integral coupling elements may be provided on the retractor to allow attachment to the supporting ring at different radial positions with respect to the supporting ring. The integral coupling elements are generally radially spaced-apart on an underside of the upper panel of the retractor. The coupling element often comprises a channel element configured to snap-fit to the ring. The channel element may be configured to face at least partly radially inwardly so that it interfaces with a radially outward aspect of the ring. This means that during use when the retractor is cupping an incision and retracted, the forces acting on the retractor will pull it radially inwardly, which when the channel element is facing at least partially radially inwardly, will result in the channel being secured to the ring. FIG. 26 illustrates this and shows a channel element 51A on the retractor that is facing radially inwardly. The connecting elements may also be a projection (e.g. a lug) on the ring, generally disposed on a top aspect of the ring), and a projection-receiving slot on the retractor. Generally a plurality of radially spaced-apart slots are provided on an underside of the upper panel of the retractor. The slot may be a re-entrant slot. The re-entrant slot may be configured to freely receive the projection in a first radial position of the slot relative to the projection and then lock the slot to the projection in a second radial position of the slot relative to the projection. Generally the second position of the slot is radially inwards of the first position. Such a re-entrant slot allows the retractor to cup a section of the incision and be manually retracted so that the slot is in the first position relative to the projection, placing the slow over the projection, and then allowing the retractor to be pulled radially inwardly under forces exerted by the opened incision where the slot will lock to the projection. FIGS. 18 and 19 illustrate such as re-entrant slot on the retractor. The projection may also be configured to prevent up and down movement (away from and towards the patient) of the retractor when in a locked position. For example the projection may have a head and a stem where the head is bigger than the stem, and the slot may have a radially inward slot part that is dimensioned to receive the head part and a radially outward slot part that is too small to receive the head part. An example of a projection for use with a re-entrant slot is shown in FIG. 7B, and an example of a re-entrant slow is shown in FIGS. 18 and 19. The coupling (connecting) element may also be a connector that is detachably mountable to the supporting ring and include a formation configured for attaching to a corresponding formation on a retractor. The formation on the detachable connector may be a projection as described previously. The formation on the detachable connector may also be channel configured to receive channel-engaging formation on the retractor. The channel-engaging formation on the retractor may be a rail element configured to engage and be retained within the channel typically in a sliding relationship. The rail element may extend radially along the retractor (generally extend radially along at least a part of the underside of the upper panel of the retractor). The rail element and channel may have complimentary profiles configured for interlocking engagement with the channel. The channel may be partially or fully recessed in the supporting ring. The channel generally extends radially across the supporting ring. This embodiment is shown in FIG. 41. The rail may have a series of radially spaced apart teeth. The supporting ring may have a circumferential groove. The connector may be configured for engagement with the rail and supporting ring allowing one of the teeth on the rail engage with the groove on the supporting ring to lock the retractor to the ring to prevent rotation of the connector on the ring. The connector may be configured to unlock the locking mechanism when the retractor is pitched inwardly or outwardly and lock the locking has zero or low pitch. This is illustrated in FIGS. 64 and 65.

The coupling element of the invention may be self-locking. "Self-locking" as applied to the coupling element means that the coupling element locks the retractor on the ring once it has been attached and released by the user. An example is the use of a lug and slot arrangement described below, where once the slot on the retractor has engaged the lug, the forces exerted on the retractor by the opened incision cause the lug and slot to lock in position and remain in position until the position of the retractor is adjusted by the user. Other methods of self-locking coupling elements could include ratchet and pinion type mechanisms, or snap-fit coupling elements configured for friction fitting the retractor and supporting ring in relative position.

"Outwardly facing direction" as applied to the disposition of the retractor and the supporting ring means that the retractor, when attached to the supporting ring, faces outwardly to cup and hold a section of the incision in an open configuration.

"Fixed saddle-shaped retractor" means a retractor that forms part of the supporting ring and is not configured for retrofitting to, or detachment from, the supporting ring during surgery. When the system is for caesarean section surgery, the fixed retractor is typically a retractor of the type designed to hold back the bladder during a caesarean section (also known as a Doyen retractor).

"Radial adjustment" as applied to the retractor or coupling element should be understood to mean movement of the retractor to open or close the incision, i.e. from a position within the ring towards a periphery of the ring, or vice versa. The movement does not have to be exactly radial. The provision of a coupling element that allows easy radial adjustment of the position of the retractor with respect to the supporting ring, provides the flexibility to allow the incision to be further opened (or closed) after the retractor has been attached to the ring.

"Circumferential adjustment" as applied to the coupling element means that the coupling element is configured to allow movement of the retractor between at least two circumferential positions along the supporting ring. In one embodiment the coupling elements comprises a carriage configured for sliding movement along the supporting ring and may include brake means for fixing the position of the coupling element with respect to the supporting ring or be self-locking when position and released by a user.

"Obese" in the context of the patient means a BMI of greater than 25, 30 or typically greater than 35. This, in one aspect, the invention relates to a system and method for use with obese patients, and especially obese pregnant women.

Exemplification

The invention will now be described with reference to specific Examples. These are merely exemplary and for illustrative purposes only: they are not intended to be limiting in any way to the scope of the monopoly claimed or to the invention described. These examples constitute the best mode currently contemplated for practicing the invention.

Referring to the drawings, and initially to FIGS. 1 to 4, there is illustrated a surgical access system of the invention, indicated generally by the reference numeral 1 and comprising a supporting ring 2, an adjustable saddle-shaped retractor 3, and a coupling element 20 for retro-fitting the adjustable retractor 3 to the supporting ring 2 in a desired position.

Figure 1B:
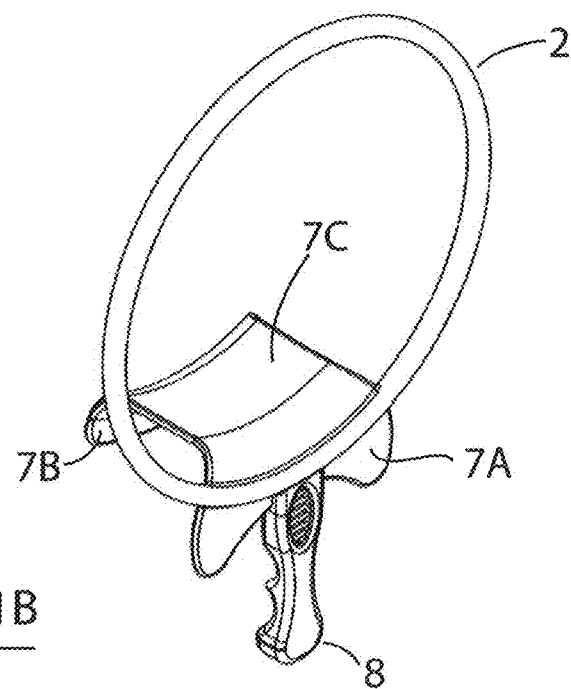

In more detail, and referring to FIG. 1, the supporting ring 2 is circular and has a circumference sufficiently large to allow delivery of a new-born baby through the ring. Thus, this ring is slightly larger than a new-born infants head. The ring 2 includes a saddle-shaped retractor 7 fixed to the ring in an outwardly facing position, and an outwardly-projecting handle 8 disposed above the fixed retractor 7. The retractor 7 is generally U-shaped, and has an upper wall 7A, lower wall 7B, and rear wall 7C having a convex curvature that matches, and is aligned with, the curvature of the supporting ring 2. All of the corners 8 on the retractor are curved and do not include any sharp corners or edges.

Figure 2A:
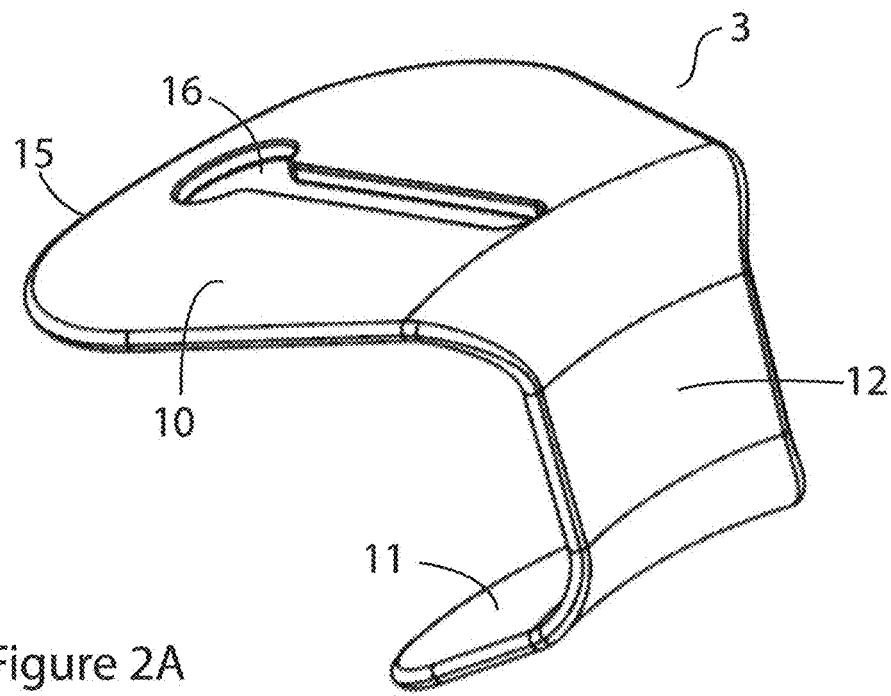
FIGS. 2A and 2B are perspective views of a first embodiment of an adjustable saddle-shaped retractor forming part of a surgical access system according to the invention.
Figure 2B:
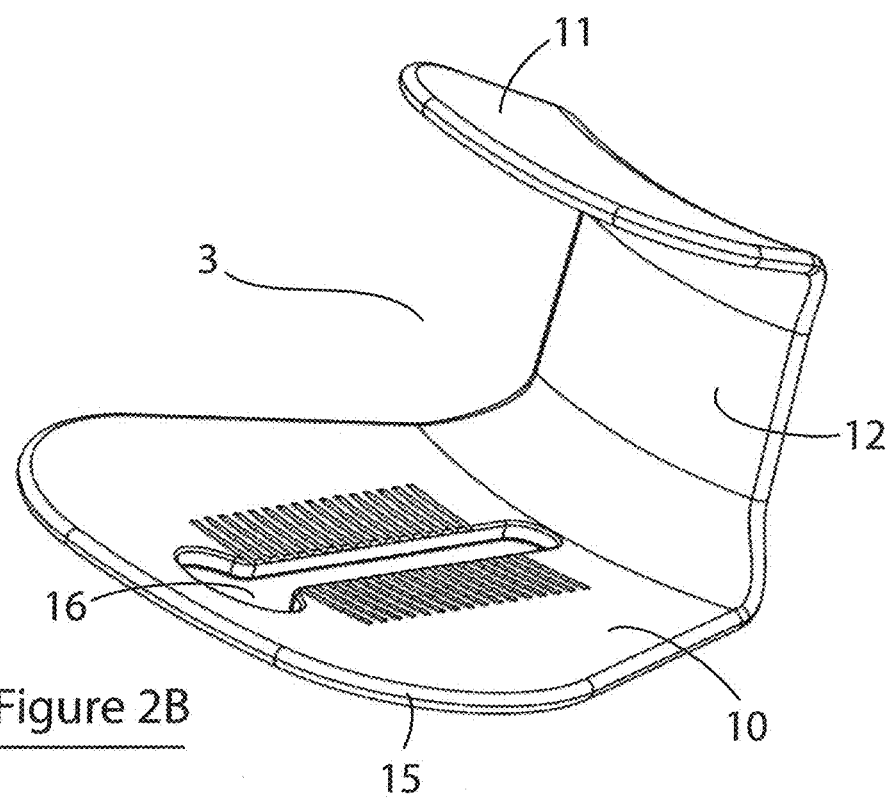

Referring to FIG. 2, the adjustable saddle-shaped retractor 3 is shown in more detail, and includes an upper wall 10, lower wall 11, and rear wall 12 provided in a U-shape with the upper and lower walls being slightly splayed outwardly. The rear wall 12 has a convex curvature. The upper wall 10 is longer than the lower wall 11 and has a trapezoid shape that widens from the rear wall 12 to a free end 15 and includes an elongated re-entrant slot 16.

Figure 3A:
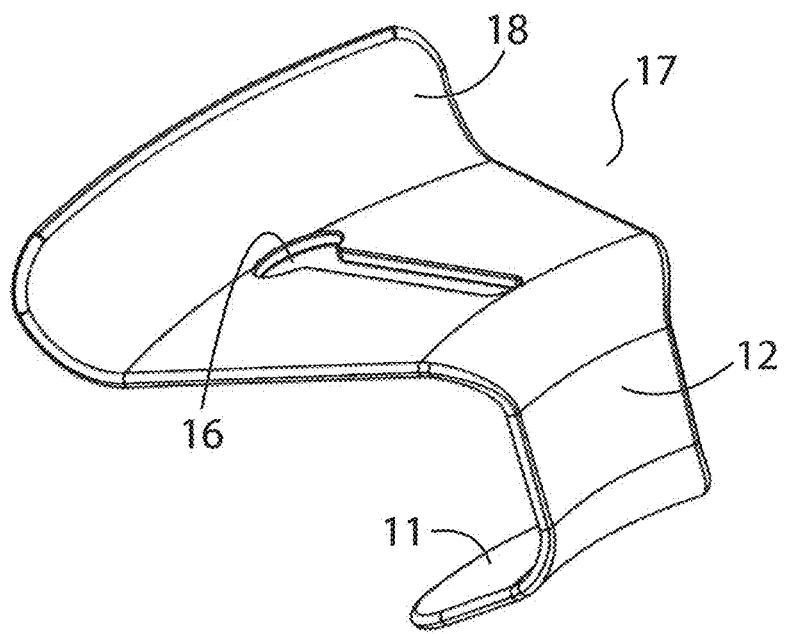
FIGS. 3A and 3B are perspective views of a second embodiment of an adjustable saddle-shaped retractor forming part of a surgical access system according to the invention and having a panniculus-deflecting lip.
Figure 3B:
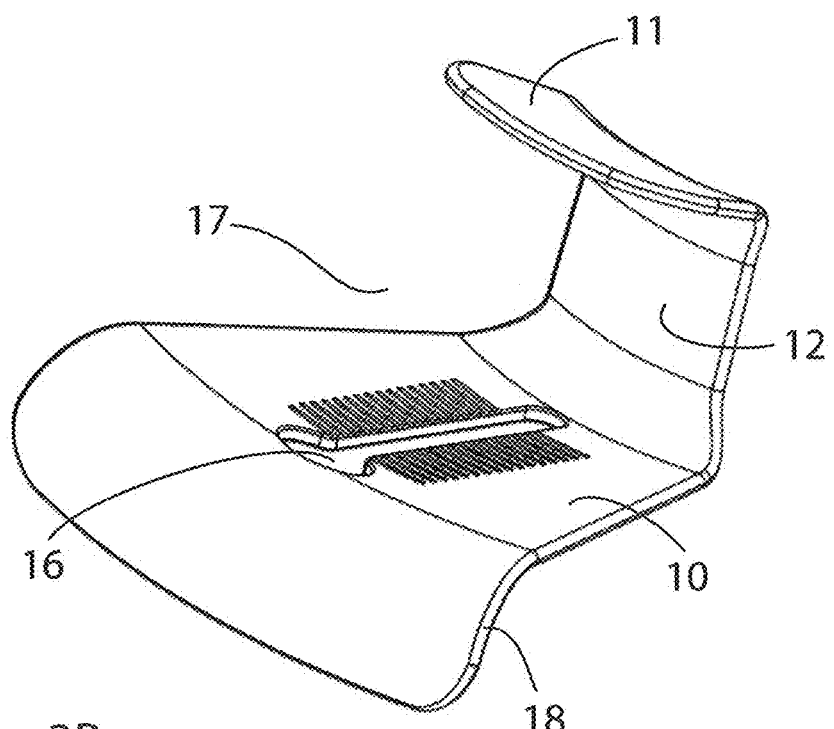

Referring to FIG. 3, a modified adjustable saddle-shaped retractor 17 is illustrated in which parts identified with reference to the previous embodiment is assigned the same reference numerals. In this embodiment, the upper wall 10 is longer and has an upwardly depending lip 18 which functions in use to deflect abdominal tissue away from the opened incision.

Figure 4:
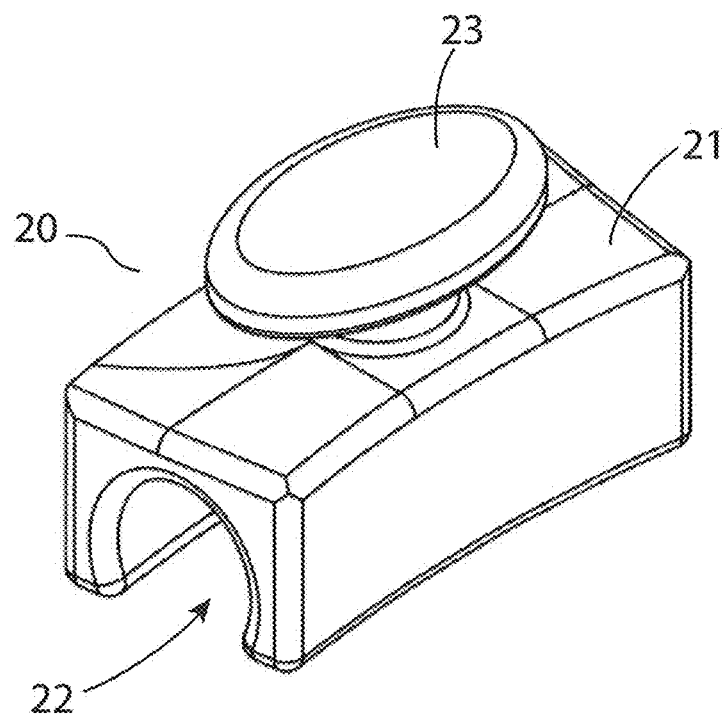
FIG. 4 is a perspective view of a coupling element forming part of a surgical system according to the invention.

Referring to FIG. 4, a coupling element 20 for retro-fitting a retractor 3, 17 to the supporting ring 2 is illustrated, and comprises a carriage 21 with a groove 22 having an elliptical profile on a lower surface thereof dimensioned to engage the supporting ring 2 in a tight but sliding arrangement. The use of a groove having an elliptical profile helps prevent rotation of the carriage on the supporting ring. A slot-engaging lug 23 is provided on a top surface and is dimensioned to engage to engage the re-entrant slot 16 of the upper wall 10 of the retractor 3, 17.

Figure 5:
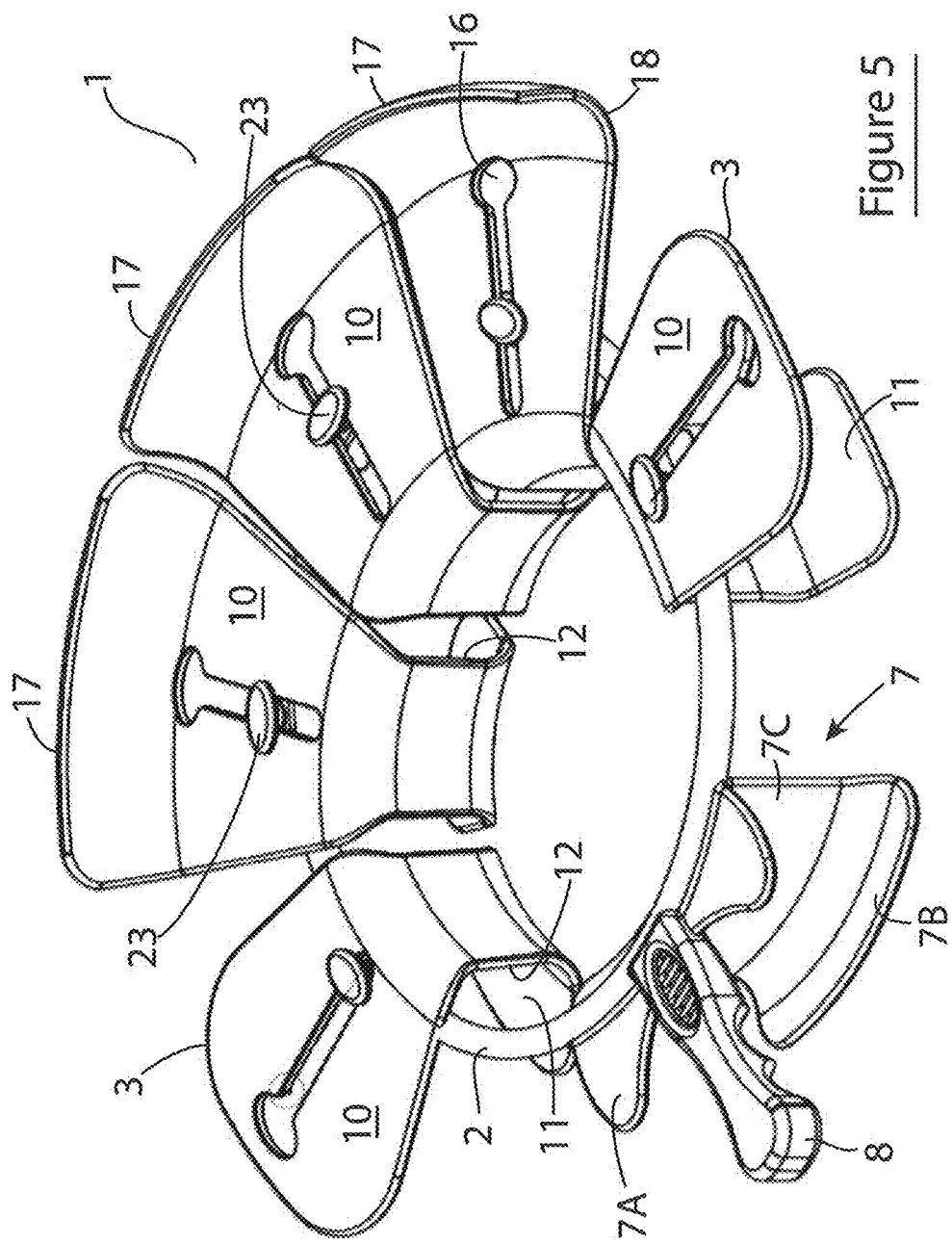
FIG. 5 is a perspective view of a surgical system according to one embodiment of the invention with the retractors attached to the supporting ring in a partly retracted configuration.
Figure 6:
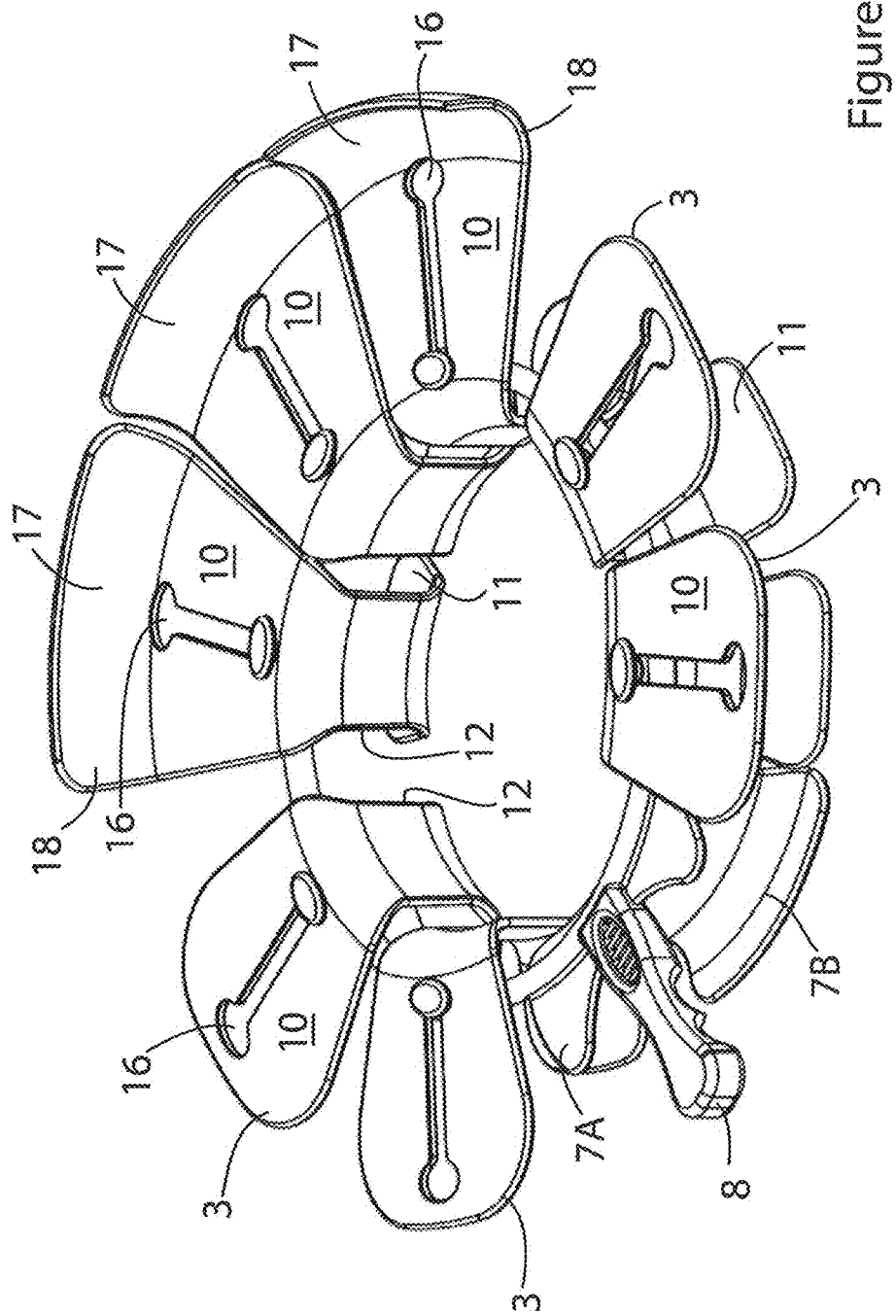
FIG. 6 is a perspective view of the surgical system of FIG. 5 with the retractors shown in a fully retracted configuration suitable for providing access to the uterus and womb during a caesarean section procedure.

Referring to FIG. 5, a surgical system of the invention 1 is illustrated with the retractors 3, 17 attached to the supporting ring 2 in an outwardly facing, and partly retracted, configuration. The modified retractors 17 with the panniculus-deflecting lip 18 are attached to the ring 2 opposite the fixed retractor 7, and the other two retractors 3 are attached to the ring on each side of the fixed retractor. FIG. 6 illustrates the same surgical system with two additional retractors 3, and after the retractors 3, 17 have been adjusted radially outwardly to a full retraction position illustrated. It can be seen from FIG. 6 how the upper walls of the retractors are dimensioned to dovetail when placed side-by-side on the ring in a fully retracted position.

Figure 7A:
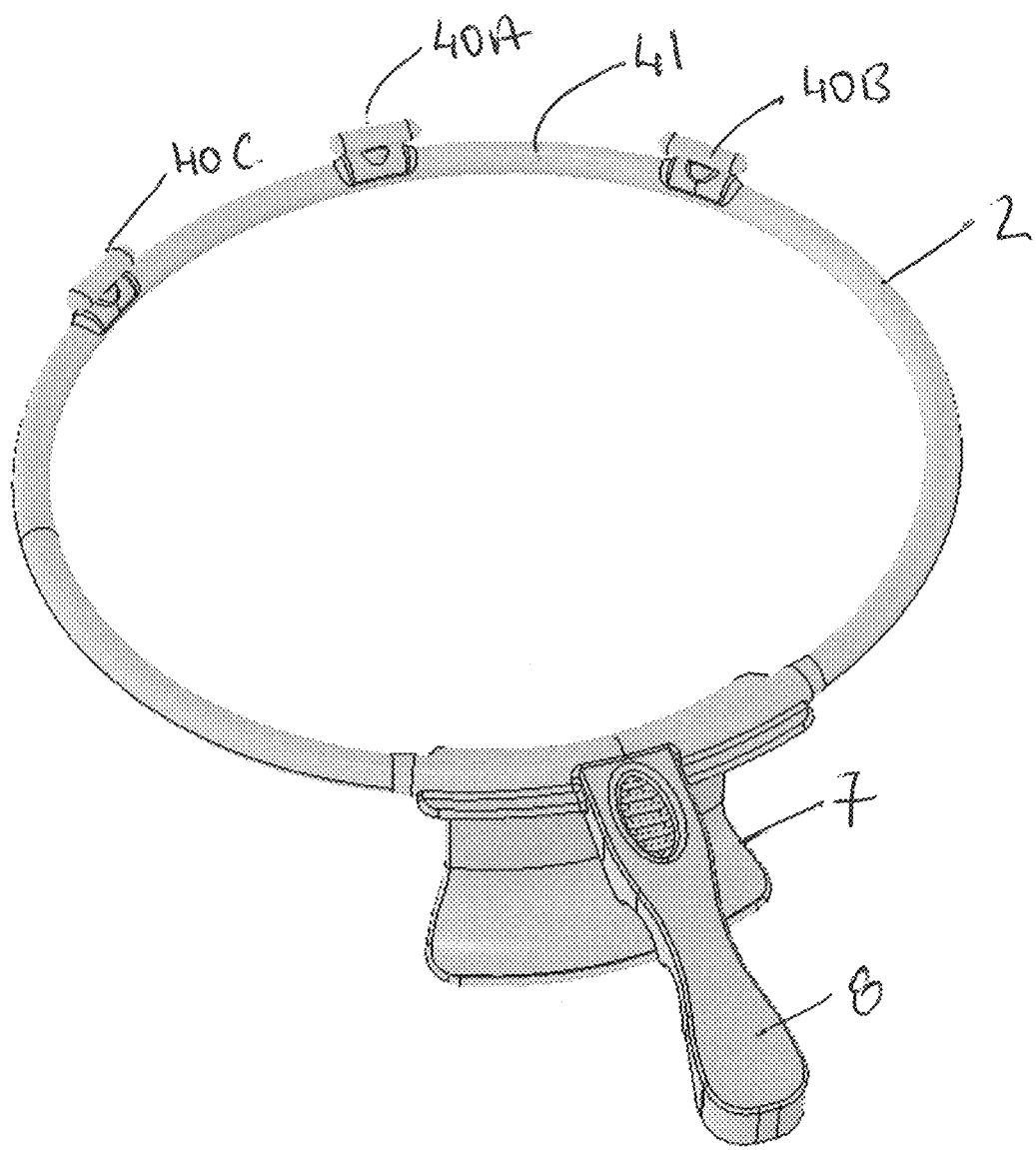
FIGS. 7A and 7B are perspective views from above of a supporting ring forming part of a surgical access system according to one embodiment of the invention and having a fixed saddle-shaped retractor and first formations (T-shaped projecting lugs) integrally formed with the projecting ring including a central lug disposed diametrically opposite the fixed retractor and flanking lugs on each side of the fixed retractor.
Figure 7B:
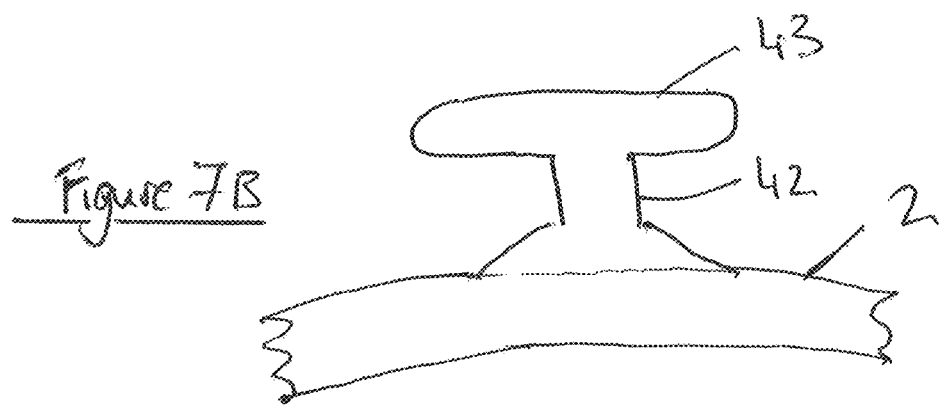

Referring to FIG. 7A a supporting ring 2 forming part of a surgical access system according to one embodiment of the invention is illustrated in which parts described with reference to the previous embodiments are assigned the name reference numerals. In his embodiment, the coupling elements include three T-shaped lugs 40 integrally formed on a top surface 41 of the ring including a central lug 40A disposed diametrically opposite the fixed retractor 7 and flanking lugs 40B, 40C on each side of the central lug 40A. Referring to FIG. 7B, each lug 40 has a cylindrical stem part 42 projecting upwardly from the top surface of the ring 2 and a T-shaped head 43 that is aligned with ring.

Figure 8:
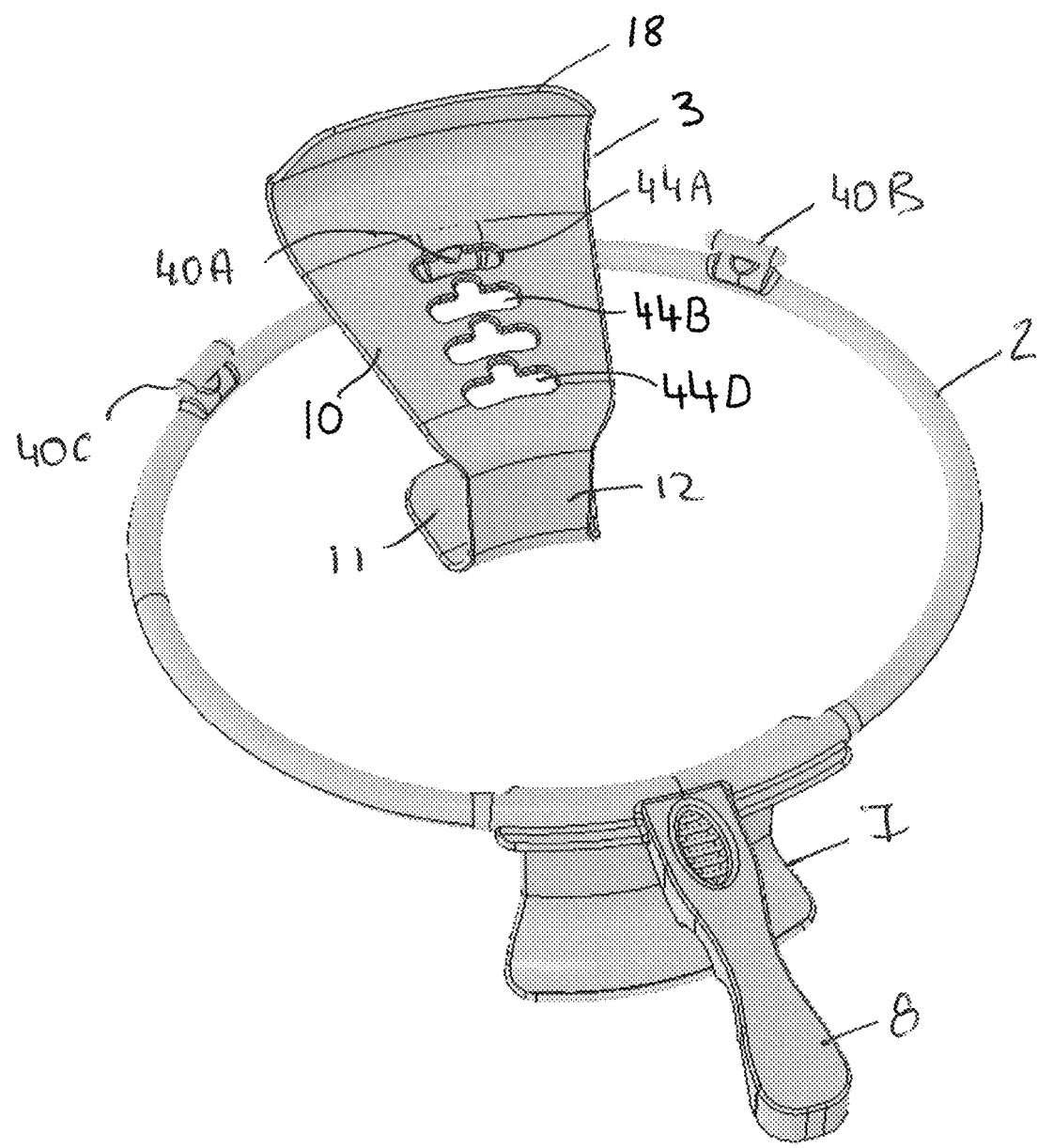
FIG. 8 is a is a perspective view of the supporting ring of FIG. 7 showing a radially adjustable saddle-shaped retractor having a series of radially spaced apart corresponding second formations (slots) with the retractor attached to the ring by engagement between the central T-shaped lug of the ring and the radially outward slot of the retractor.

FIG. 8 shows the supporting ring 2 with a radially adjustable saddle-shaped retractor 3 attached to the ring. The retractor 3 includes a plurality of slots 44 radially spaced apart along the upper panel 10 of the retractor and configured to engage with a T-shaped lug 40. Each slot 44 is a re-entrant slot, the details of which will be described in more detail below. In the image shown, the T-shaped lug is engaged with the first (radially outermost) slot 44A.

Figure 9:
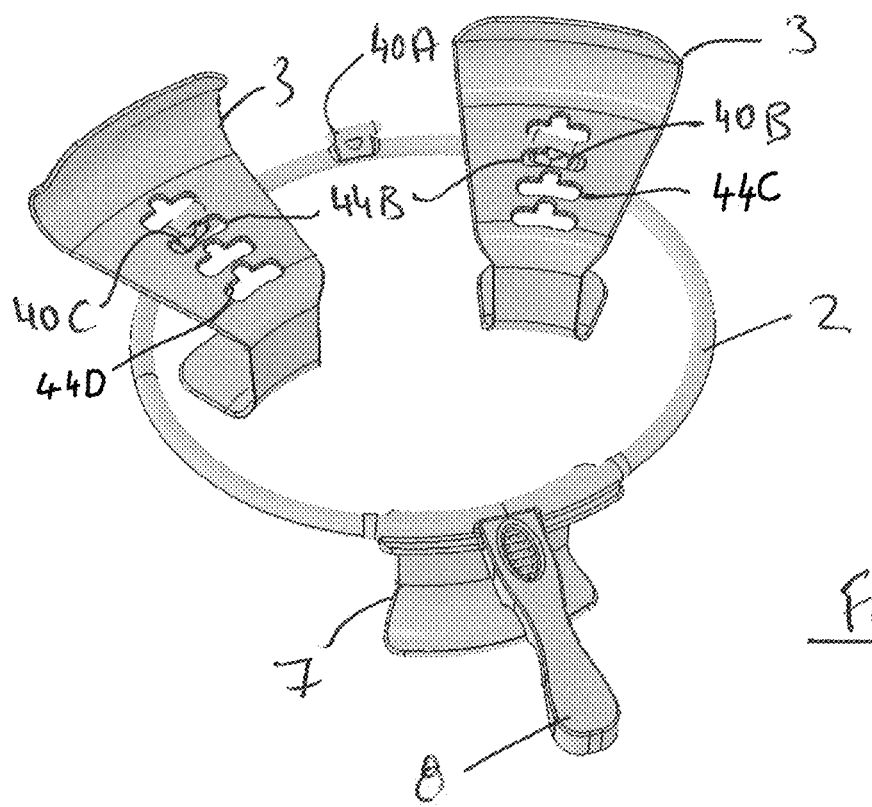
FIG. 9 is a is a perspective view of the supporting ring of FIG. 7 showing two radially adjustable saddle-shaped retractors each having a series of radially spaced apart corresponding second formations (slots) with the retractors attached to the ring by engagement between the flanking T-shaped lugs of the ring and second slots of the retractor. In this position, the retractors are retracted further that the retractor shown in FIG. 8.

FIG. 9 shows the supporting ring 2 of FIG. 7 with two radially adjustable saddle-shaped retractors 3 attached, each retractor attached to the ring by engagement between the flanking T-shaped lugs 40B, 40C of the ring and second slots 44 of the retractor. In this position, the retractors are retracted further that the retractor shown in FIG. 8.

Figure 10A:
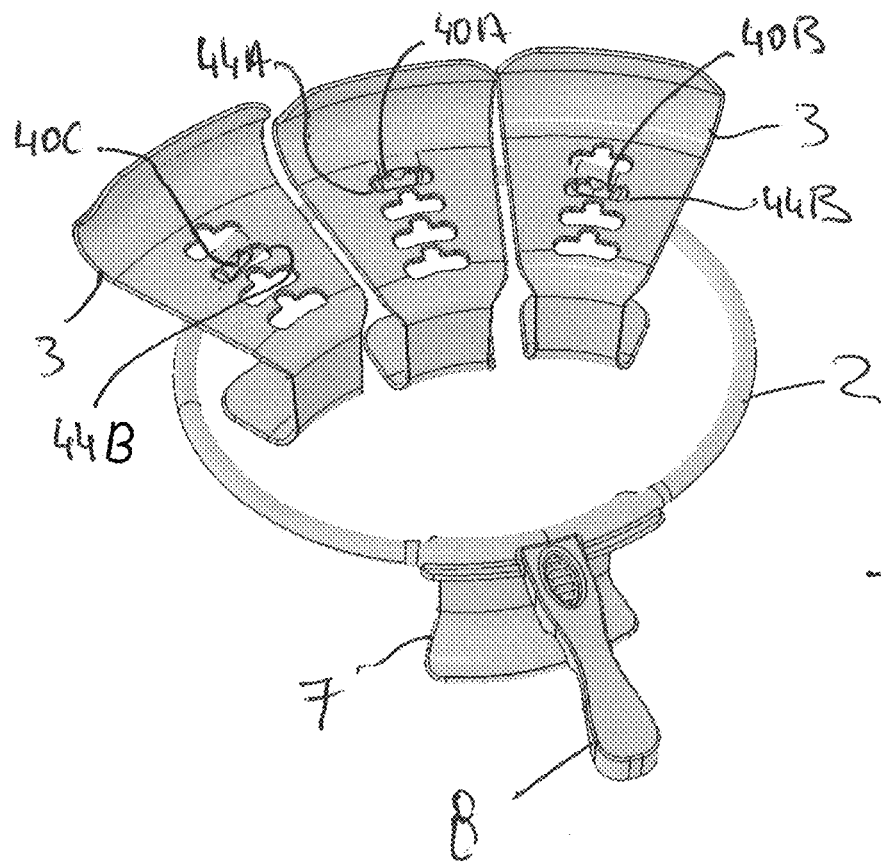
FIG. 10A is a is a perspective view of the supporting ring of FIG. 7 showing three radially adjustable saddle-shaped retractors each having a series of radially spaced apart corresponding second formations (slots) with the retractors attached to the ring by engagement between the central and flanking T-shaped lugs of the ring, in which the central retractor is attached to the central lug by means of its radially outermost slot and the flanking retractors are attached to the flanking lugs by means of their second slots.

FIG. 10A shows the supporting ring of FIG. 7 with three radially adjustable saddle-shaped retractors 3 attached to the ring by engagement between the central and flanking T-shaped lugs of the ring, in which the central retractor is attached to the central lug 40A by means of its radially outermost slot 44A and the flanking retractors are attached to the flanking lugs 40B, 40C by means of their second slots 44B.

Figure 10B:
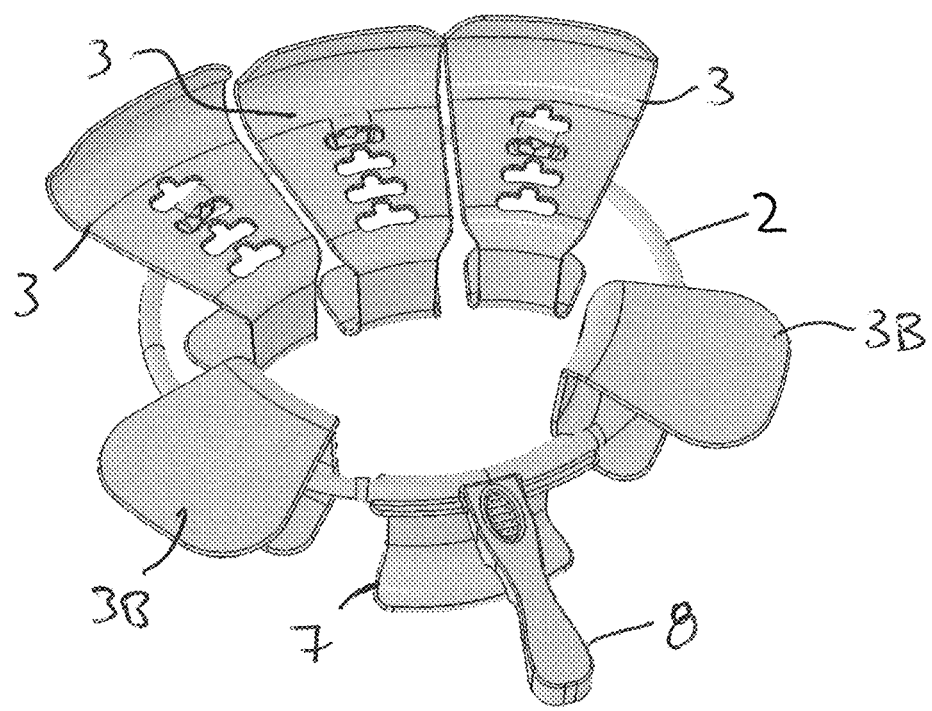
FIG. 10B is a view of the system of FIG. 9 showing two additional saddle-shaped retractors attached to the ring flanking the fixed retractor.

FIG. 10B is a view of the system of FIG. 9 showing two additional saddle-shaped retractors 3B attached to the ring flanking the fixed retractor.

FIGS. 11 and 12 show a section of the supporting ring 2 showing the central and flanking T-shaped lugs 40A to 40C integrally formed with the ring at 0°, 48° and 312° (in which the fixed retractor is positioned on the ring at 180°). FIG. 12 illustrates how the T-bar head 43 of the lug 40 is aligned with the ring 2.

FIG. 13 shows a radially adjustable paddle 3 straddling the supporting ring 3 with the second slot 44B positioned above the central T-shaped lug 40A. The T-shaped lug is also shown is more detail with the upstanding stem 42 and T-bar head 43 at the top. A panniculus deflecting lip 18 is also shown extending upwardly in a curved slightly S-shape from a distal end of the upper panel 10 of the retractor 3.

FIG. 14 shows the supporting ring 2 showing a rear side of the fixed retractor 7 and the handle 8. The fixed retractor is integrally formed with the ring 2 and is positioned diametrically opposite the central lug 40A.

FIGS. 15, 16 and 17 illustrate the configuration of the re-entrant slot 44 on the retractor and how it engages with the T-shaped lug 40. As illustrated in these figures, the re-entrant slots 44 have a radially inward slot part 46 that is oversized with respect to the T-shaped head 43 and a radially outward slot part 47 that is smaller than the T-shaped head but dimensioned to friction fit with the stem 42 of the lug.

FIG. 15 shows a radially adjustable retractor 3 engaging with the supporting ring 2 with the T-shaped head 43 projecting through the radially inward slot part 46. FIG. 16 shows the retractor moved radially inwardly which forces the stem 42 of the lug into a friction fit engagement with the radially outward part 47 of the slot 44.

FIGS. 18 and 19 show the lug 40 engaging with the re-entrant slot 44, showing how the radially inward part 46 of the slot is oversized to accommodate and tolerate a ±8° of user misalignment, with respect to the T-shaped head 43 of the lug which facilitates the alignment of the lug and the slot in the pressurised environment of a surgical procedure.

FIG. 20 shows two radially adjustable retractors 3 attached to a supporting ring 2, illustrating how the coupling elements allow yaw movement of the retractors 3 relative to the ring when they are locked to the ring (yaw arrows). It will be appreciated that the forces acting on the retractors when they are in a tissue retracting position is a radially inwards force (arrow A), which serves to lock the lug in the radially outward part of the re-entrant slot while allow side to side yaw movement of the retractors relative to the supporting ring.

Figure 21A:
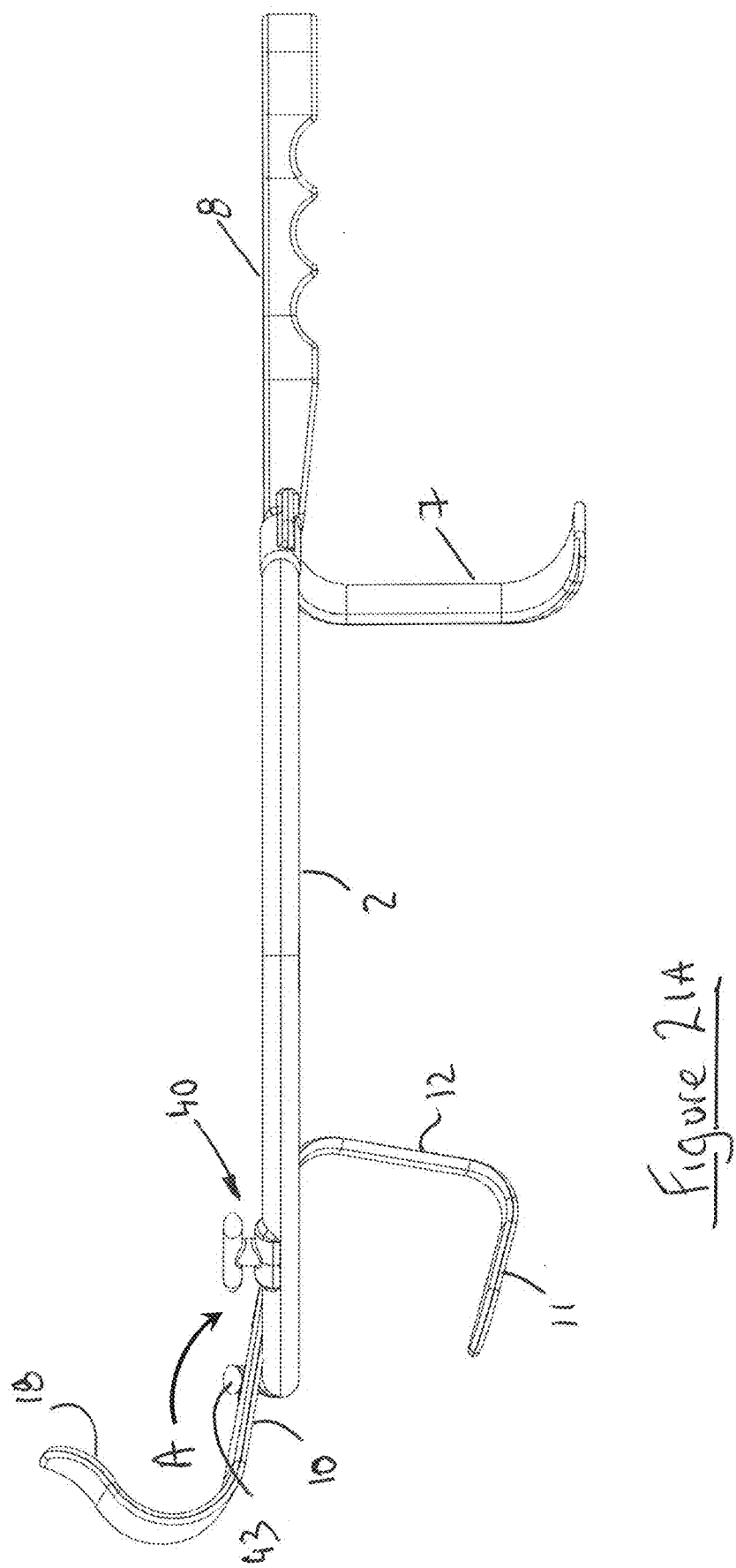
FIGS. 21A and 21B are side elevational views of a radially adjustable retractor attached to a ring showing how the coupling means allows inward (FIG. 21A) and outward (FIG. 21B) pitched movement of the retractor relative to the supporting ring.
Figure 21B:
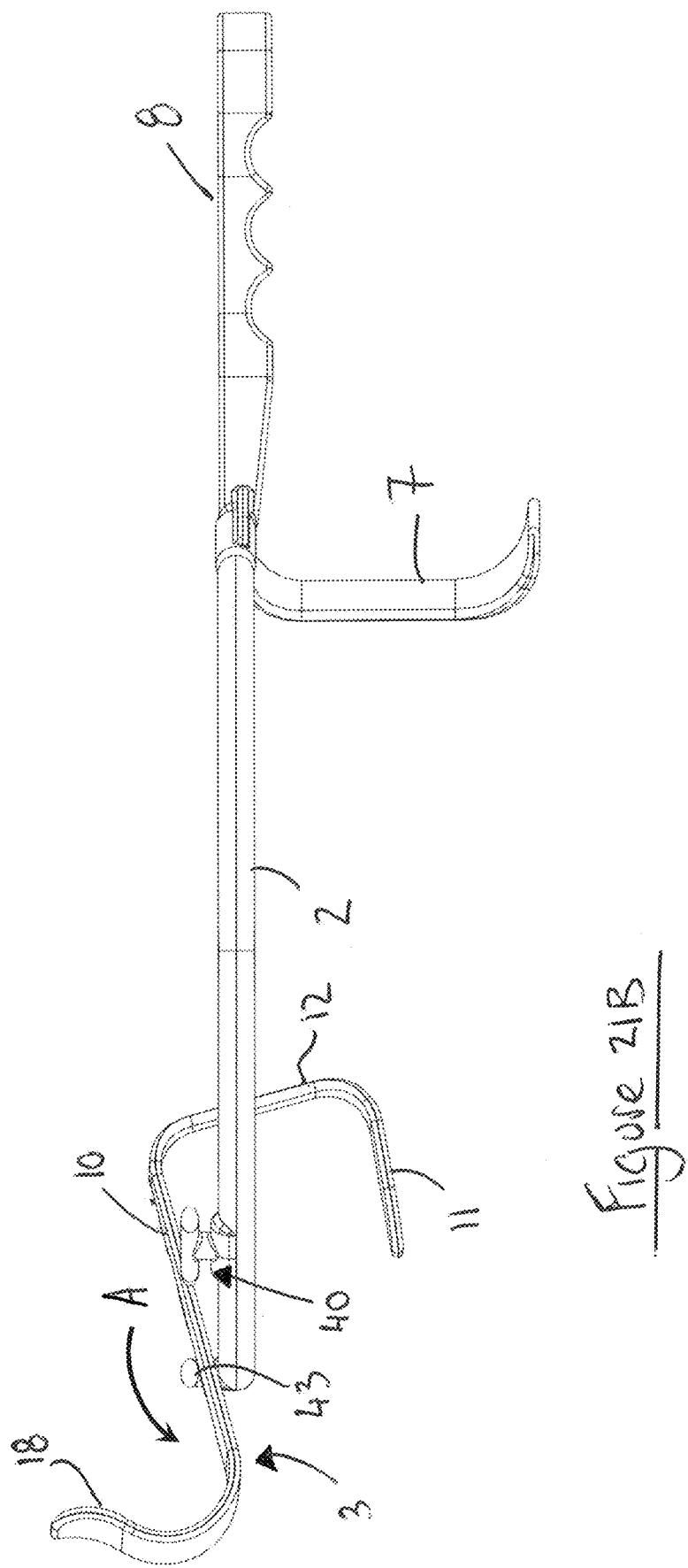

FIGS. 21A and 21B show the radially adjustable retractor 3 attached to a ring 2 showing how the coupling means allows inward (FIG. 21A) and radially outward (FIG. 21B) pitched movement (arrow A) of the retractor relative to the supporting ring. The degree of pitch can be controlled by the height of the stem 42.

Figure 25:
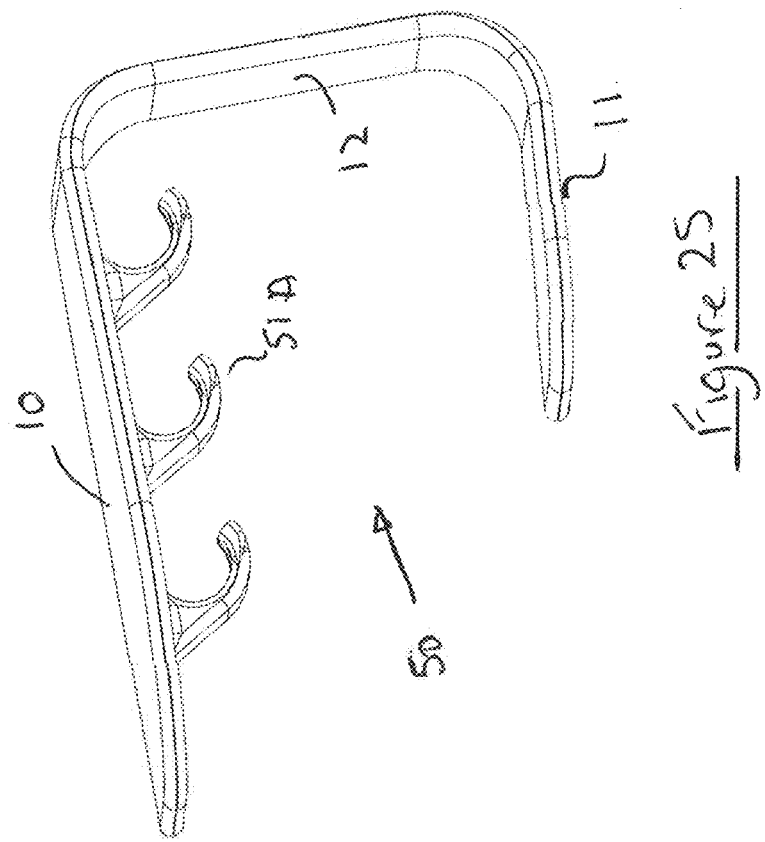
FIGS. 24 and 25 are perspective views of the radially and circumferentially adjustable retractors of FIGS. 22 and 23 but without the panniculus deflecting lip.
Figure 24:
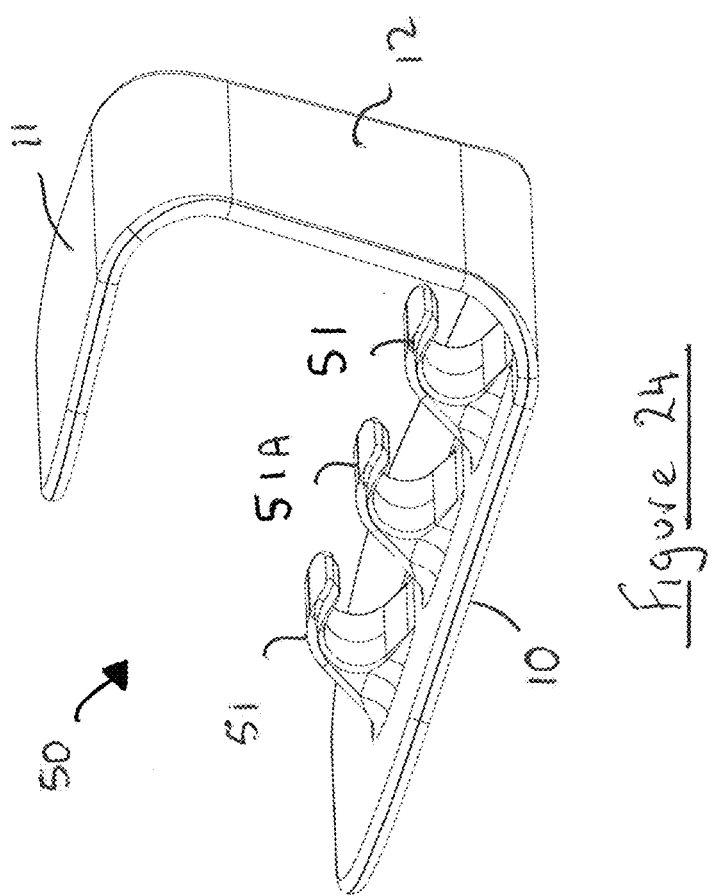

FIGS. 22 and 23 illustrate another embodiment of a radially adjustable retractor in which parts identified with reference to the previous embodiments are assigned the same reference numerals. In this embodiment the retractor, indicated generally by the reference numeral 50, has a series of three radially spaced apart hooks 51 integrally formed on an underside of the upper wall 10 and configured for snap-fit attachment directly to the supporting ring. A proximal end of the upper panel 10 includes an upwardly depending panniculus deflecting s-shaped lip 18 that has a height approximately the same as the height of the rear panel of the retractor. FIGS. 24 and 25 show a similar embodiment of the retractor of FIGS. 22 and 23 but without the panniculus deflecting lip. FIG. 26 illustrates two of the retractors 50 attached to a supporting ring 2 on each side of the fixed retractor 7 by means of the middle hook 51A. FIG. 27 is a plan view from above of the retractors of FIGS. 24 and 25 showing how the hooks on the underside of the retractor allow both circumferential and radial adjustment of the retractors 50 on the ring 2.

Figure 29:
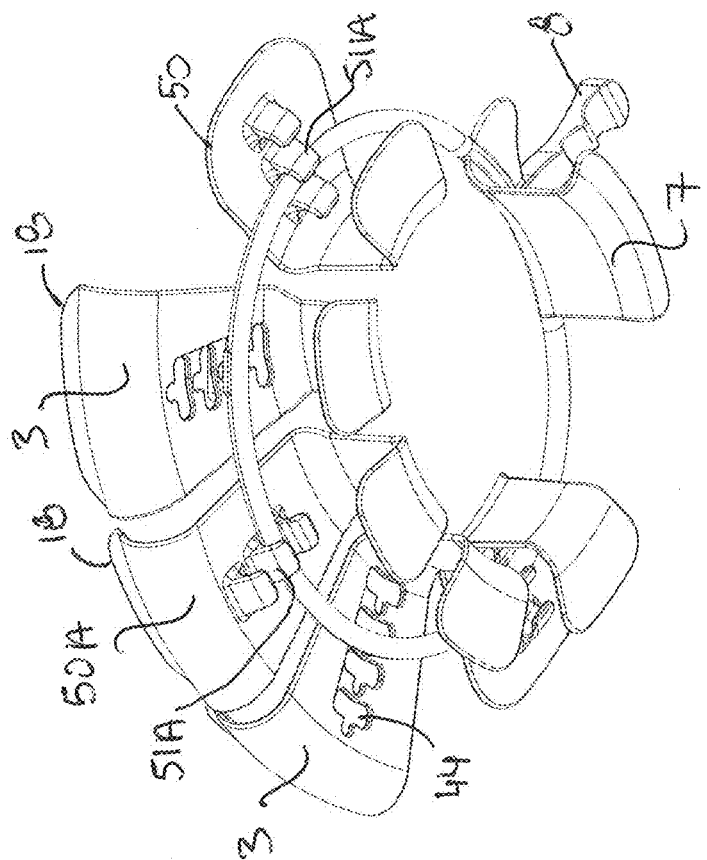
FIGS. 28 and 29 illustrate one embodiment of the system of the invention with a supporting ring with a fixed saddle shaped retractor, three circumferentially and radially adjustable retractors (one diametrically opposed to the fixed retractor), and two radially adjustable retractors flanking the central retractor.
Figure 28:
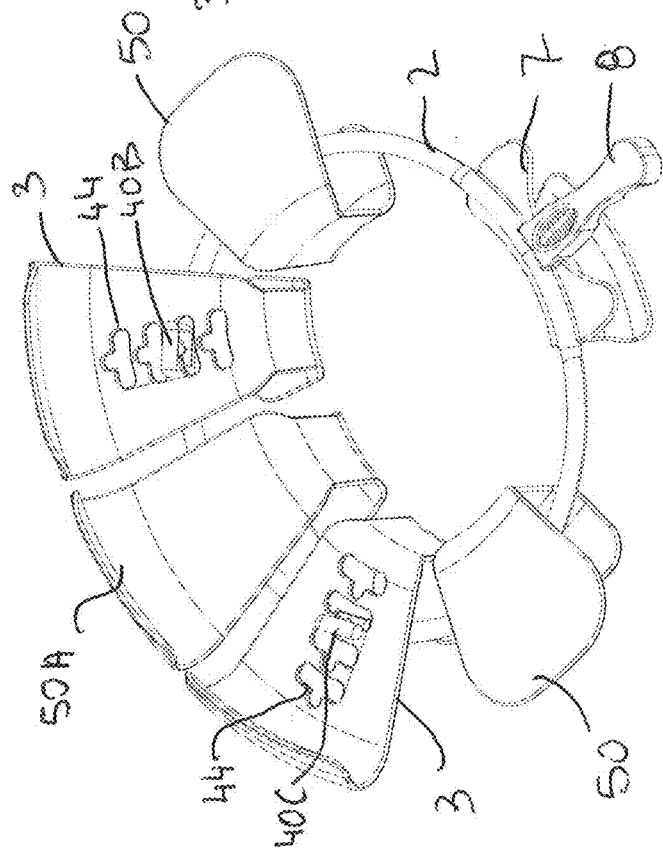

FIGS. 28 and 29 illustrate a system of the invention with a supporting ring 2 and integrally formed fixed saddle shaped retractor 7, three circumferentially and radially adjustable retractors 50 (one retractor 50A diametrically opposed to the fixed retractor) that are attached to the ring 2 by snap-fit engagement between the hooks 51A and the ring, and two radially adjustable retractors 3 having slots 44 flanking the central retractor and coupled to the ring by engagement between lugs 40B and 40C and corresponding slots 44 on the retractors 3.

FIGS. 30 and 31 illustrate another embodiment of the system of the invention that is identical to the system illustrated in FIGS. 28 and 29 with the exception that the retractor mounted to the ring diametrically opposite to the fixed retractor 7 is a radially adjustable retractor that attached to the ring by engagement between the mounting lug 40A and slot 44 on the retractor (as described previously).

Figure 32:
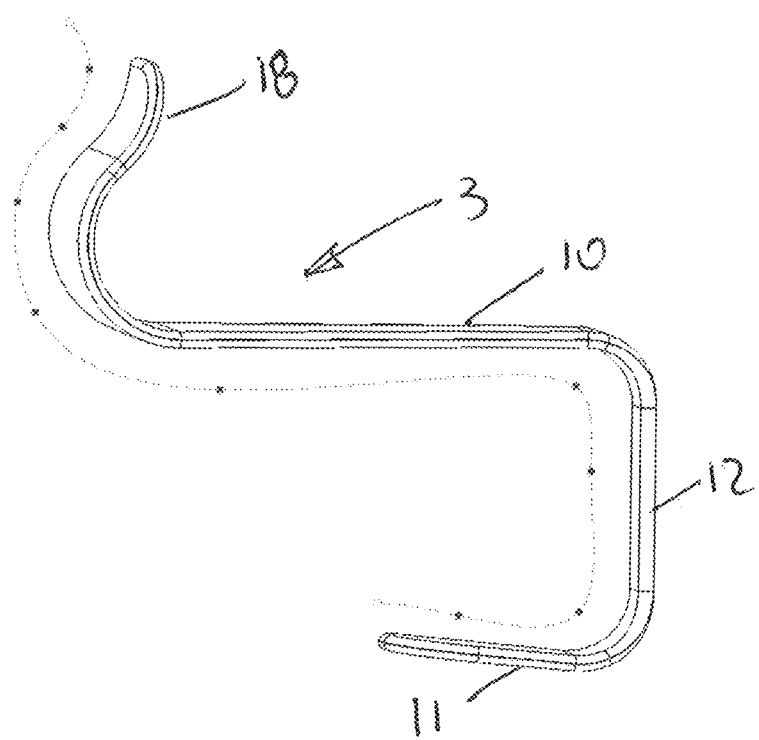
FIG. 32 is a side elevations profile view of a retractor showing the curved inflection between the upper panel and the lip, and between the rear panel and the upper panel and lower panel. This view also illustrates the S-shape of the panniculus deflecting lip, and also illustrates how the lower panel projects slightly upwardly towards the upper panel (by about 5°).

FIG. 32 is a side elevations profile view of a retractor showing the curved inflection between the upper panel 10 and the lip 18, between the rear panel 12 and the upper panel 10, and between the rear panel 12 and lower panel 11. This view also illustrates the S-shape of the panniculus deflecting lip 18, and also illustrates how the lower panel 11 projects slightly upwardly towards the upper panel 10 (by about 5°). The shape of the retractor in profile is indicted by the dotted line.

Figure 33:
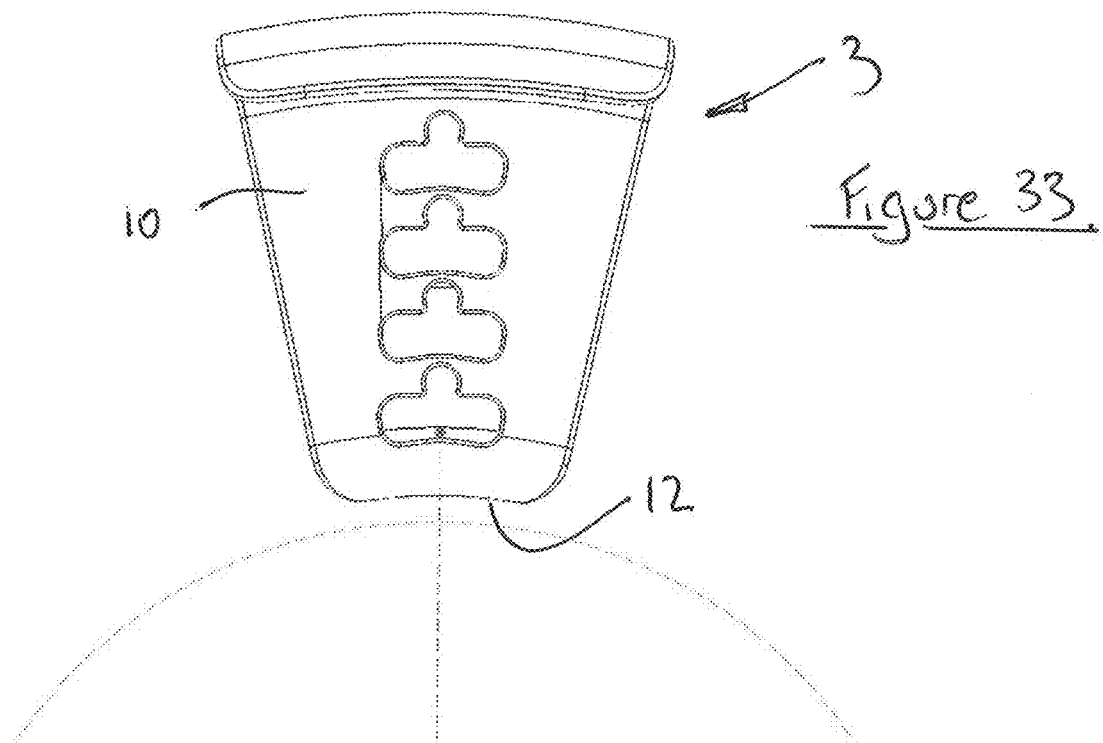
FIGS. 33 and 34 are plan views from above of a radially adjustable retractor showing the convex curvature of the rear wall allowing it to follow the curved shape of an opened abdominal incision.
Figure 34:
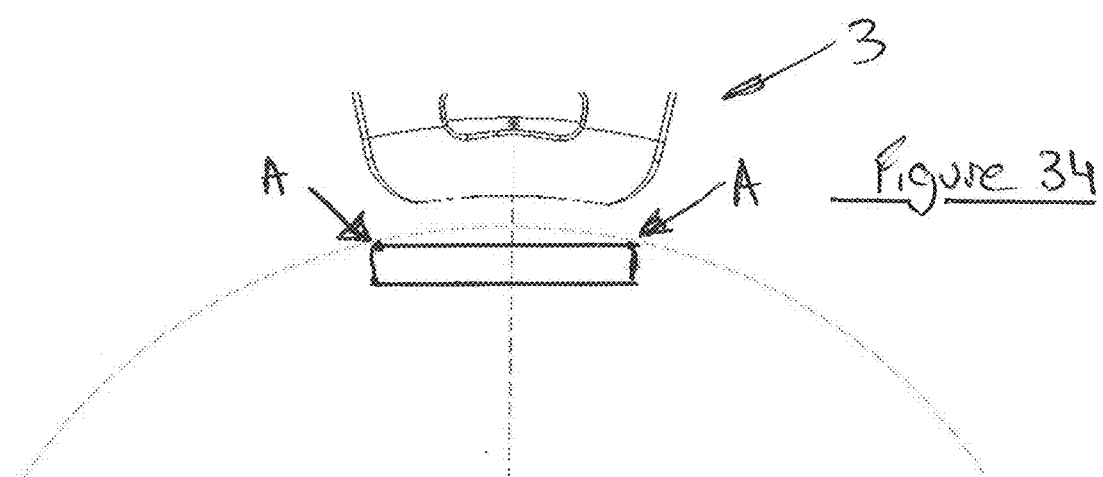

FIGS. 33 and 34 are plan views from above of a radially adjustable retractor 3 showing the convex curvature of the rear wall 12 allowing it to follow the curved shape of an opened abdominal incision. The dotted line denotes curvature relative to the rear panel of the retractor which provides curvature that follows the curvature of an abdominal incision opening, thereby minimising the stress concentration points at the edges. If the real wall 12 was not curved as illustrated by the rectangular depiction in FIG. 34, stress concentration points would occur at positions indicated by the arrows A.

Figure 35:
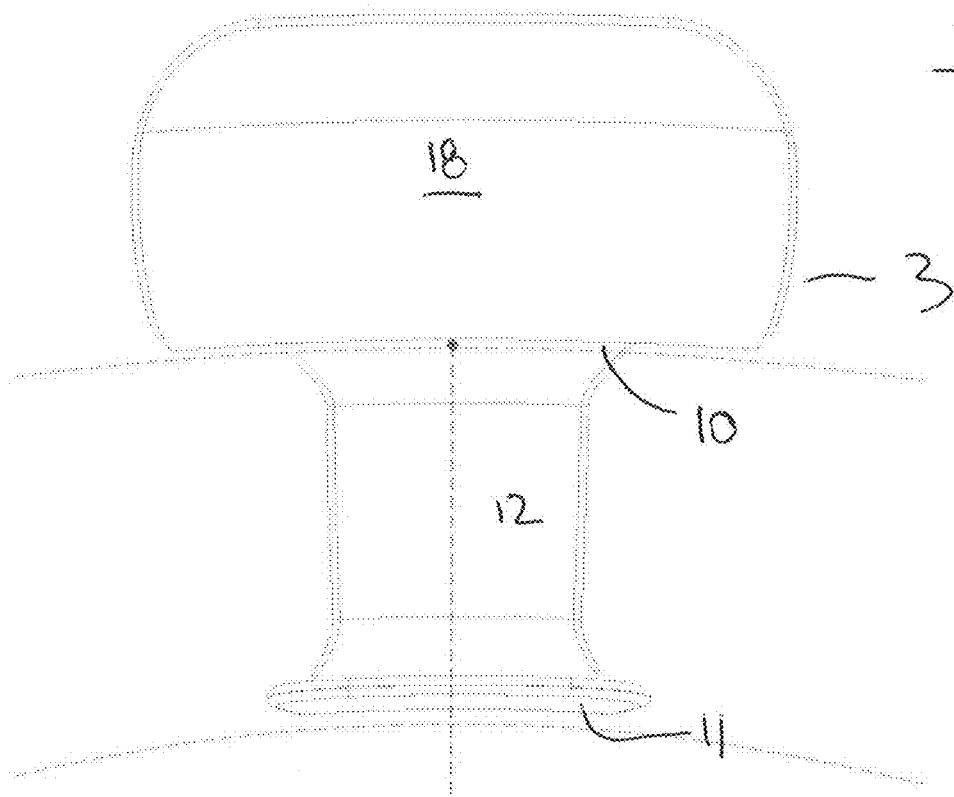
FIGS. 35 and 36 are side elevational views looking radially inwardly from a proximal end of a radially adjustable retractor and showing the curvature of the upper wall and lower wall allow them to conform to the curvature of abdominal tissue in a pregnant woman.
Figure 36:
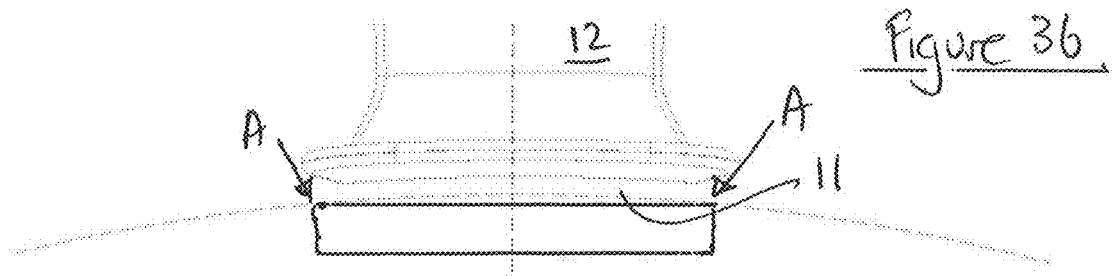

FIGS. 35 and 36 are side elevational views looking radially inwardly from a proximal end of a radially adjustable retractor 3 and showing the curvature of the upper wall 10 and lower wall 11 allowing them to conform to the curvature of abdominal tissue in a pregnant woman. Dotted line denotes curvature relative to the upper panel 10. Curvature to follow the natural 'dome' shape of the pregnant maternal abdomen, thereby minimising the stress concentration points at the edges of the paddles. If the upper wall 10 was not curved as illustrated by the rectangular depiction in FIG. 36, stress concentration points would occur at positions indicated by the arrows A.

Referring to FIG. 37, the use of the surgical access system of the invention in a caesarean section procedure is described, in which parts identified with respect to the previous embodiments are assigned the same reference numerals. It will be appreciated that the following represents one method of the using the system of the invention in surgical access, and that in use some of the steps may be performed in a different order. Also, in the following description, neither the incision, not the manual adjustment of the retractors prior to attachment to the supporting ring is illustrated, although it is described.

Figure 37A:
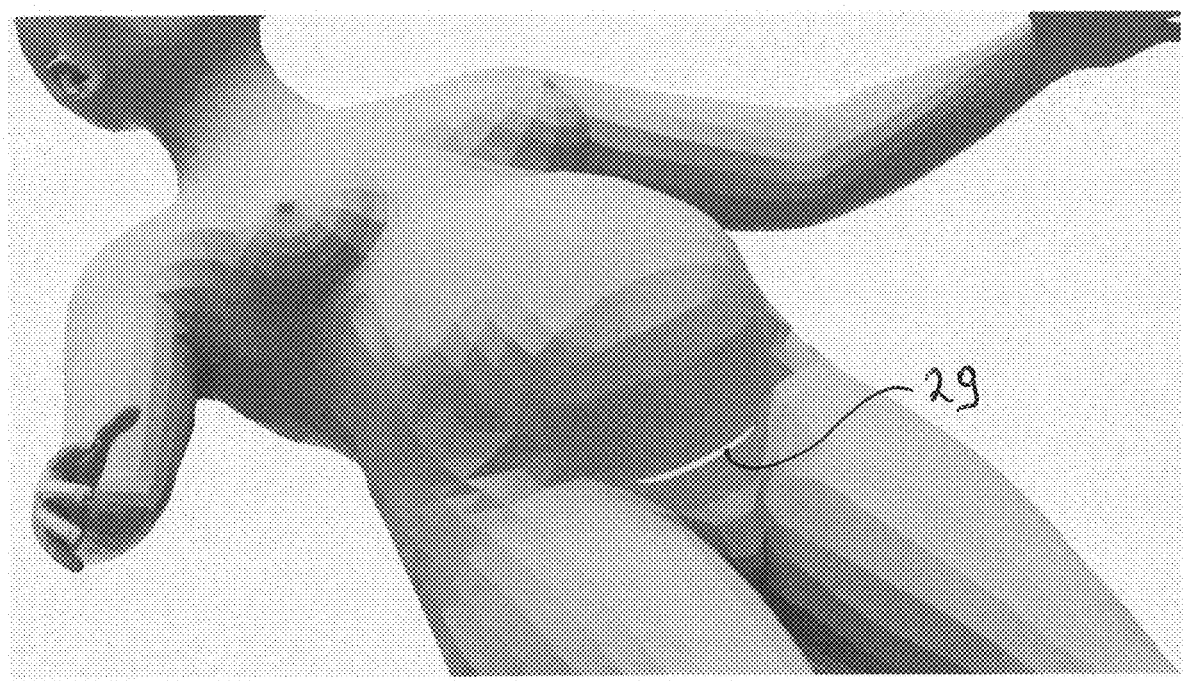
FIG. 37A is an illustration of a pregnant woman with a caesarean incision located approximately 3 centimetres above the patient's symphysis pubis.

FIG. 37A is an illustration of a pregnant woman with a caesarean incision 29 located approximately 3 centimetres above the patient's symphysis pubis.

Figure 37B:
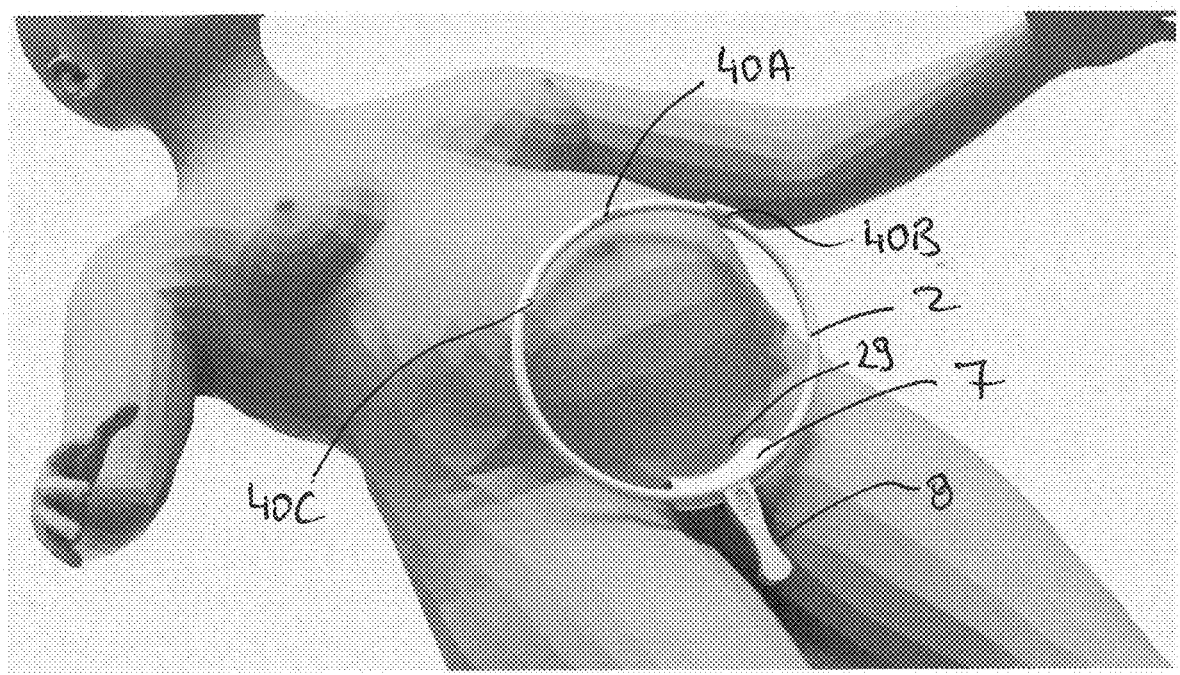
FIG. 37B shows a supporting ring placed on the woman's abdomen with the fixed saddle-shaped retraction paddle inserted into the caesarean incision covering the holding back the woman's bladder.

FIG. 37B shows a supporting ring 2 placed on the woman's abdomen with the fixed saddle-shaped retractor 7 inserted into the caesarean incision covering and holding back the woman's bladder.

Figure 37C:
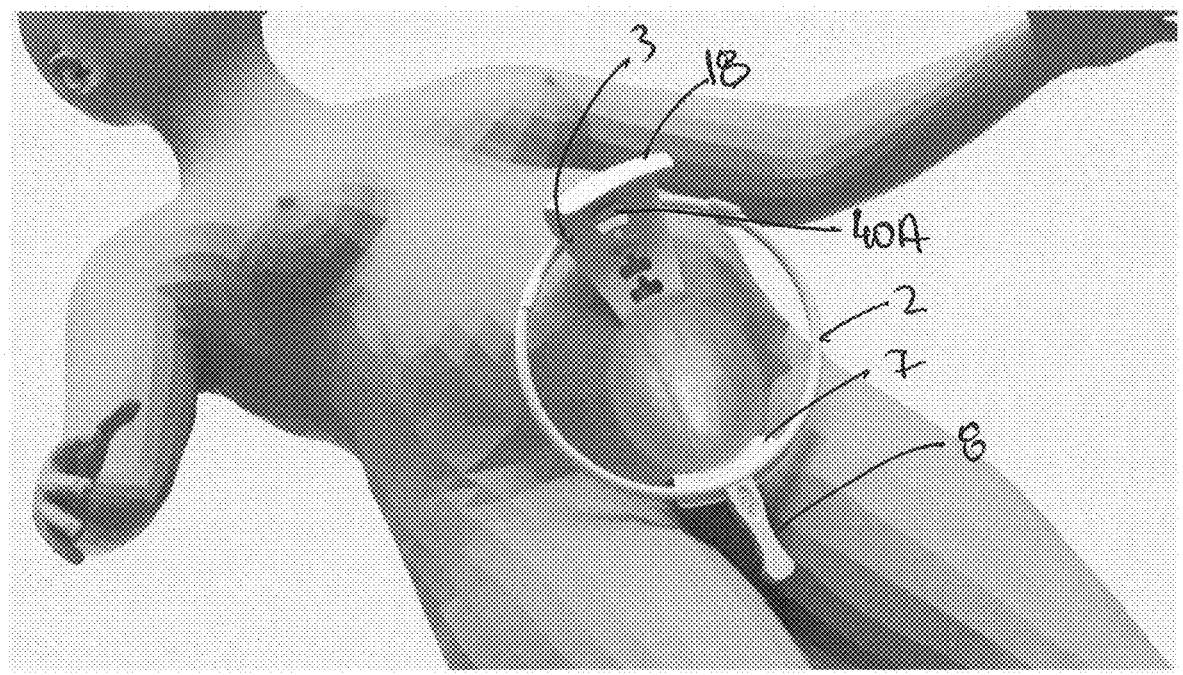
FIG. 37C shows a radially adjustable retractor (having a panniculus deflecting lip) cupping a section of tissue on the abdominal side of the incision and retracted and attached to the supporting ring via a lug on the supporting ring diametrically opposed to the fixed retractor. One the retractor is fixed to the supporting ring in a tissue retraction position, the supporting ring is then anchored to the woman and does not need to supported by a surgeon or their assistant.

FIG. 37C shows a radially adjustable retractor 3 (having a panniculus deflecting lip 18) cupping a section of tissue on the abdominal side of the incision and retracted and attached to the supporting ring 2 via a lug 40A on the supporting ring diametrically opposed to the fixed retractor 7. Once the retractor is fixed to the supporting ring 2 in a tissue retraction position, the supporting ring is then anchored to the woman and does not need to be supported by a surgeon or assistant.

Figure 37D:
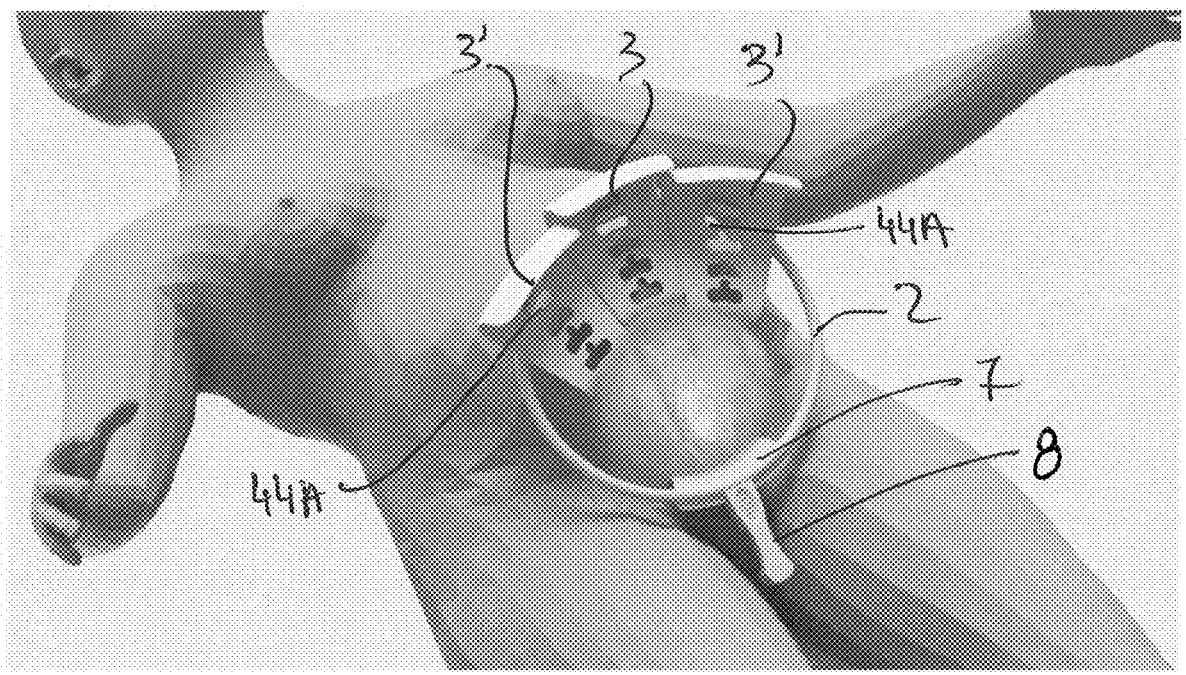
FIG. 37D shows two more radially adjustable retractors, each cupping a section of abdominal tissue and retracted to open the incision and attached to the supporting ring in positions flanking and dovetailing with the first radially adjustable retractor. At this stage, the three radially adjustable retractors are attached to the ring by the radially outermost slots and therefore the least retracted position.

FIG. 37D shows two more radially adjustable retractors 3', each cupping a section of abdominal tissue and retracted to open the incision and attached to the supporting ring 2 in positions flanking and dovetailing with the first radially adjustable retractor 3. At this stage, the three radially adjustable retractors are attached to the ring by the radially outermost slots 44A and therefore the least retracted position.

Figure 37E:
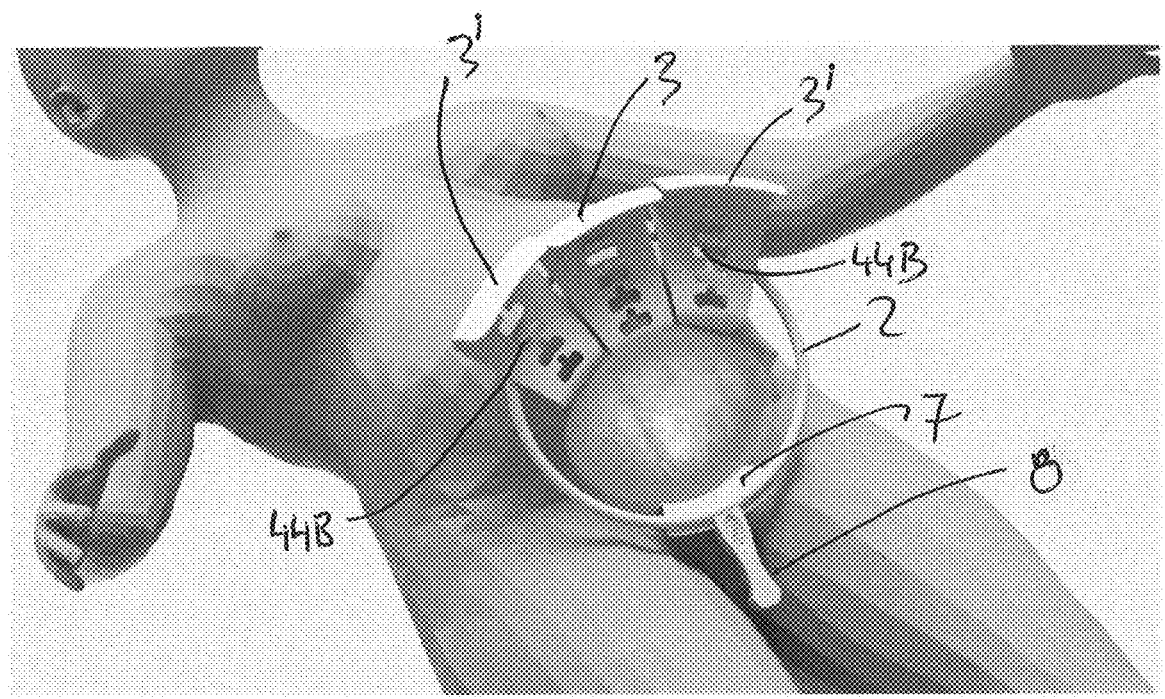
FIG. 37E shows two flanking radially adjustable retractor radially re-positioned after being detached and re-attached via a second slot (e.g. retracted further).

FIG. 37E shows two flanking radially adjustable retractors 3' radially re-positioned after being detached and re-attached via a second slot 44B on the retractor 3 (e.g. retracted further).

Figure 37F:
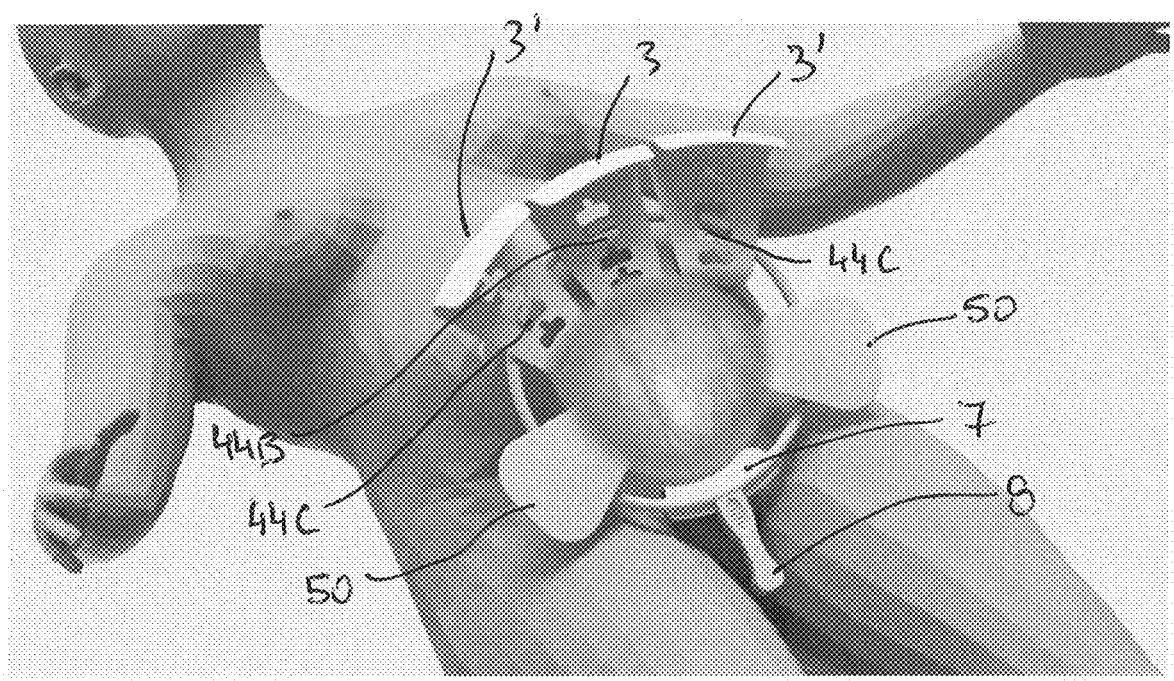
FIG. 37F shows all three radially adjustable retractors radially re-positioned after being detached and re-attached to the ring (the central retractor is not attached via its second slot and the flanking retractors are attached via their third slots. In addition, two radially and circumferentially adjustable retractors are shown retracting the sides of the incision and attached to the ring at positions flanking the fixed retractor. In this configuration, the caesarean incision is fully opened, and the Caesarean procedure can proceed.

FIG. 37F shows all three radially adjustable retractors radially re-positioned after being detached and re-attached to the ring (the central retractor 3 is now attached via its second slot 44B and the flanking retractors 3' are attached via their third slots 44C. In addition, two radially and circumferentially adjustable retractors 50 are shown retracting the sides of the incision and attached to the ring 2 at positions flanking the fixed retractor. In this configuration, the caesarean incision is fully opened, and the Caesarean procedure can proceed.

Figure 42:
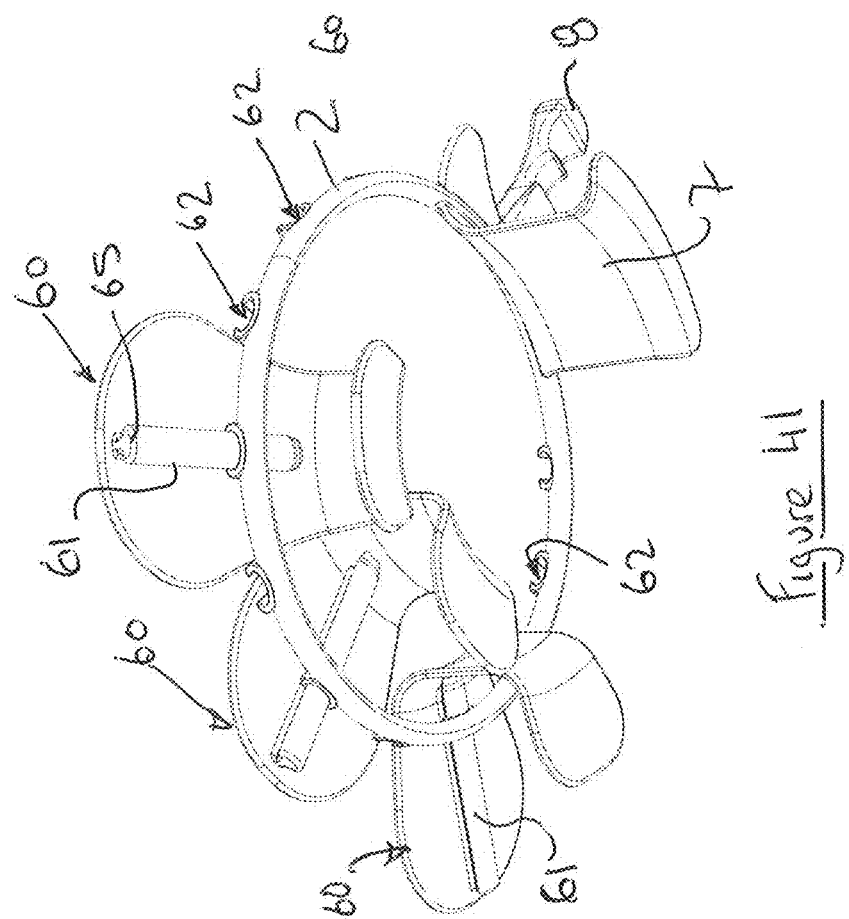

FIG. 38 shows a radially adjustable retractor according to an alternative embodiment of the invention and indicated generally by the reference numeral 60. In this embodiment, the retractor 60 has a radially extending rail 61 integrally formed with an underside of the upper panel 10 and having an inverted T-shaped profile configured to engage and slide in a corresponding formation on the ring. FIGS. 39 and 40 show the retractor 60 attached to a supporting ring 2 having a series of partially recessed channels 62 circumferentially spaced apart on a top surface of the ring 2. The channels 62 are dimensioned to receive the rails 61 of the retractor in a sliding and retaining relationship providing radial adjustment of the retractor 60 with respect to the ring 2. The channels have a profile that partially embraces the head 65 of the rail retaining the rail in the channel. FIGS. 41 and 42 show a system of the invention having a three radially adjustable retractors 60 attached to the supporting ring 2.

Figure 43:
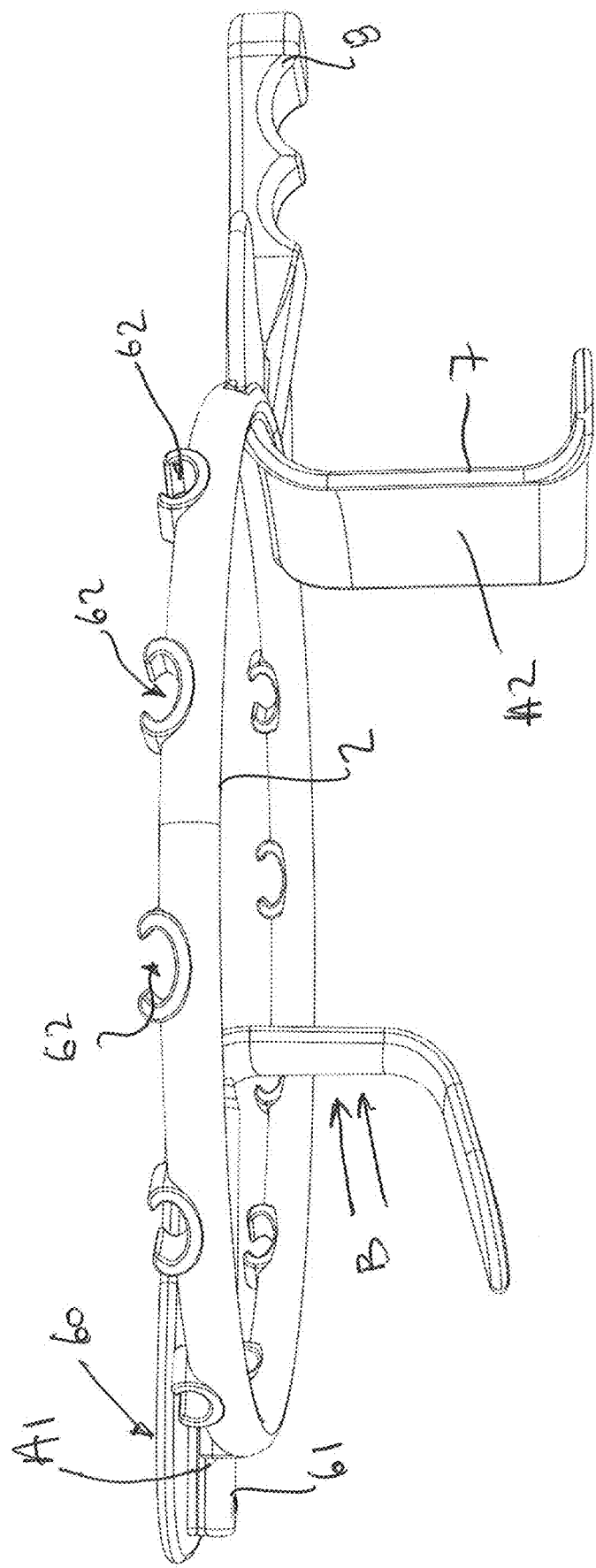
FIG. 43 is a side elevational, partially perspective, view of the system of FIG. 39.

FIG. 43 is a side elevational, partially perspective, view of the system of FIG. 39 showing the anchor points A1 and A2. Where the retractor interfaces with the ring, the sliding channel 62 becomes a locking mechanism once the user's hand has been removed. This occurs due to the offset planes, from where the abdominal forces B are acting on the paddle, relative to the point at which the paddle interfaces with the ring (anchor point A1). This results in a torsional or bending force being applied to the retractor. The resultant retractor moment applies a friction lock property, which secures the retractor in position. This locking mechanism is released when the user places their hand on the retractor and moves the retractor in the opposite direction to the applied moment, releasing the friction lock and thereby allowing the user to reposition the retractor.

Figure 45:
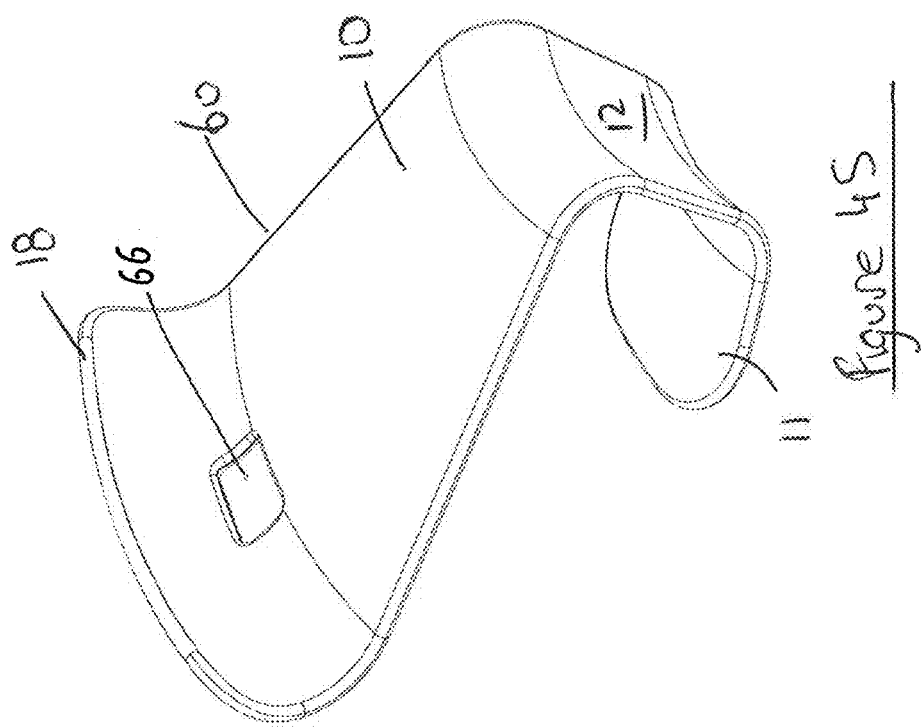
FIGS. 44 and 45 are perspective views of the retractor of FIG. 38 and including a viewing window at a proximal end of the upper wall adjacent the panniculus deflecting lip.
Figure 44:
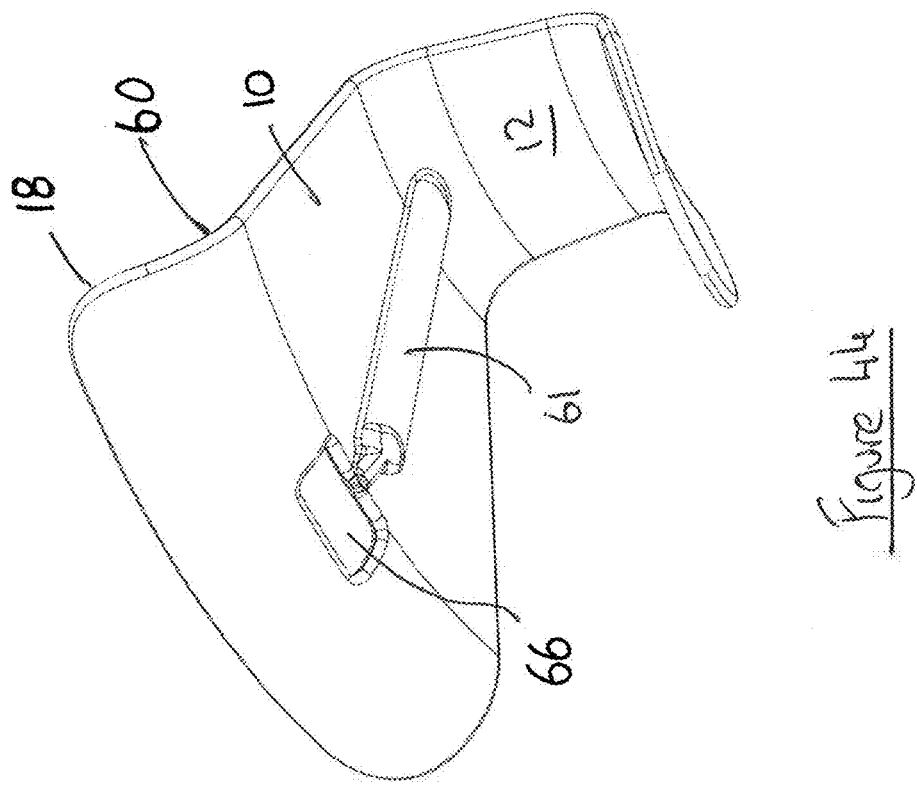
Figure 5P:
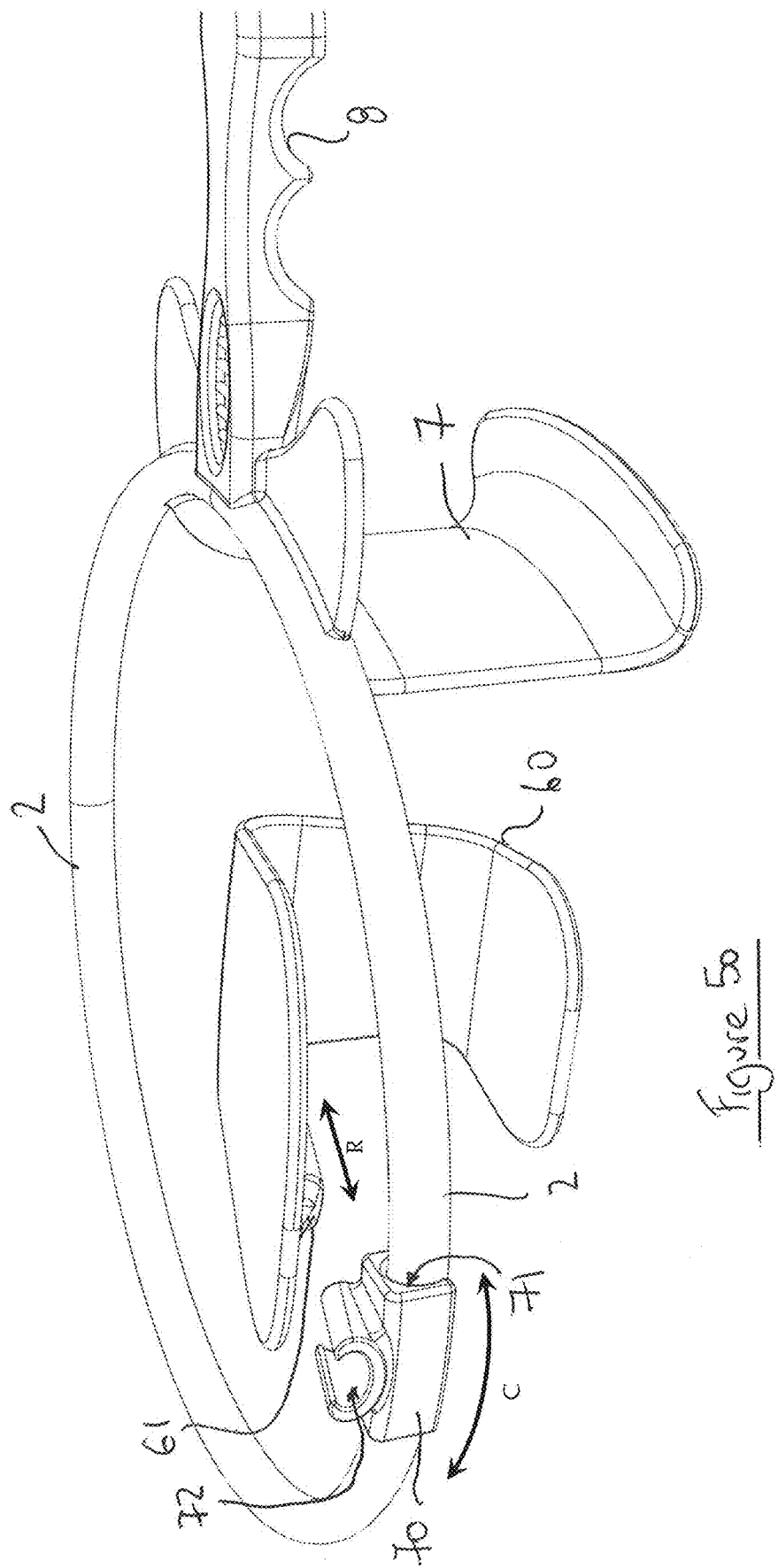

FIGS. 44 and 45 are perspective views of the retractor 60 of FIG. 38 and including a viewing window 66 at a proximal end of the upper wall adjacent the panniculus deflecting lip.

FIGS. 46 and 47 are perspective views of alternative first formations (detachable connector 70) configured to couple the retractor 60 to a supporting ring. The connector 70 comprises a body with a ring-receiving channel 71 in a lower part of the body and a rail-engaging channel 72 formed in an upper part of the body that is generally orthogonal to the ring-receiving channel so that an axis of the rail-engaging channel 72 projects radially inwardly with respect to the ring when it is attached to the ring. The ring-receiving channel 71 has an elliptical profile dimensioned to snap fit to the supporting ring. The rail engaging channel is dimensioned to receive the rail in a retaining and sliding relationship. In use the connector 70 can be attached at any point around the circumference of the ring. The connector allows radial adjustment of the retractor on the ring by sliding the retractor relative to the connector, where release of the retractor results in the locking of the rail of the retractor to the connector and the locking of the connector to the supporting ring.

FIG. 50 is a side elevational perspective view of a supporting ring 2 having a detachable connector 70 snap-fitted to the ring and a radially adjustable retractor 60 with rail 61 approaching the detachable connector. This arrows R and C how the use of this connector allows both radial (R) and circumferential (C) adjustment of the position of the retractor on the connecting ring.

Figure 52:
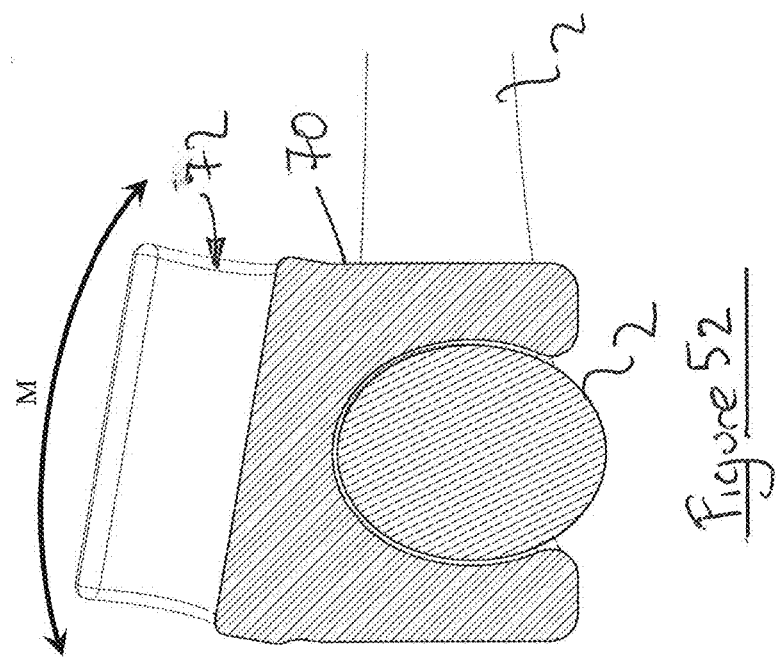
FIG. 52 is a sectional view of the supporting ring and connector taken along the section lines A-A of FIG. 51.
Figure 51:
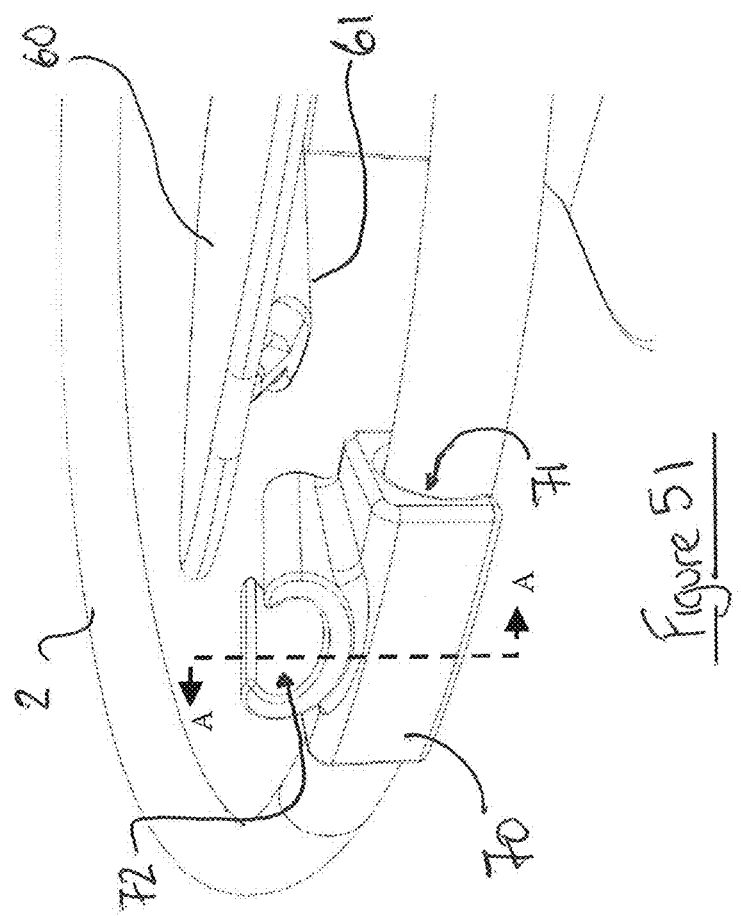
FIG. 51 is a detailed view of the system of FIG. 50 with section lines A-A.

FIG. 51 is a detailed view of the connector 70 attached to a supporting ring 2 with section lines A-A and FIG. 52 is a sectional view of the supporting ring and connector taken along the section lines A-A of FIG. 51 showing the small clearance between the elliptical ring 2 and the elliptical ring-engaging channel 71. The retractor moment, due to the forces acting upon it from use in the patient, will cause the clearance between the ring 2 and the ring-engaging channel 71 to be reduced to the point where the parts are exerting frictional contact and thereby creating a circumferential positioning locking mechanism. The elliptical shape facilitates this, whilst also providing an anti-rotation function, thereby limiting the degree of actual momentary rotation, denoted by 'M'.

Figure 55:
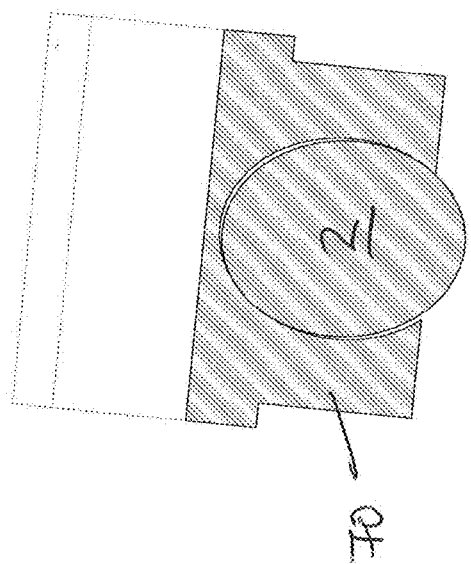
FIGS. 53 to 55 are sectional views similar to FIG. 52 showing how the elliptical shape of the ring-engaging channel allows limited pitch movement of the connector on the ring.
Figure 54:
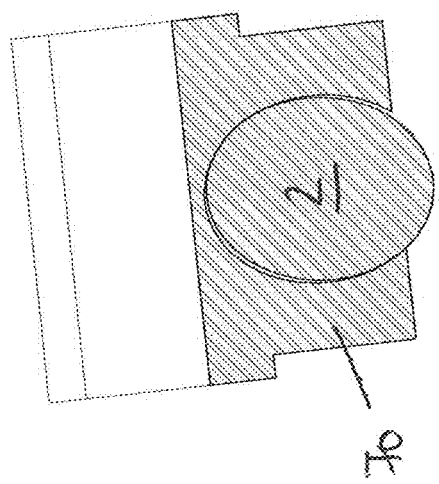
Figure 53:
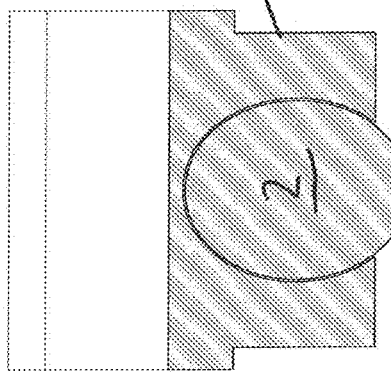

FIGS. 53 to 55 are sectional views similar to FIG. 52 showing how the elliptical shape of the ring-engaging channel allows limited pitch movement of the connector on the ring. In FIGS. 54 and 55 the connector is pitched outwardly and inwardly causing frictional locking between the ring and the channel at defined friction points. These illustrations demonstrate how the elliptical shape allows a degree of 'pitch' motion, whilst also preventing full rotation. This pitch motion results in frictional contact points, which thus prevent the circumferential movement of the coupling.

Figure 56:
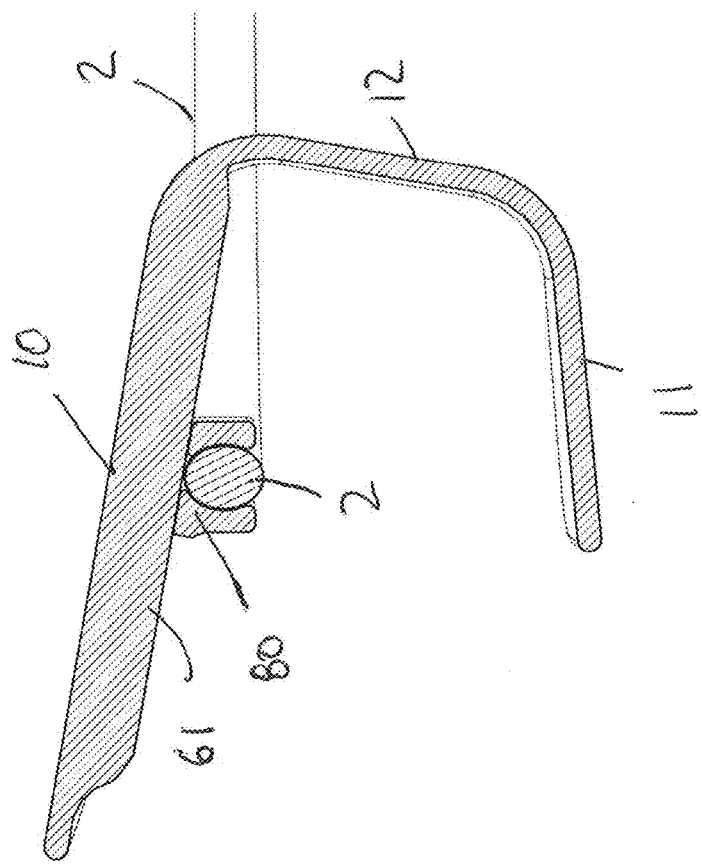
FIG. 56 is a sectional side elevational view of the radially adjustable retractor connected to the ring via the detachable connector of FIGS. 48 and 49 and showing the ring contacting the rail when the connector is pitched inwardly.

FIGS. 48 and 49 show a detachable and circumferentially adjustable connector similar to that of FIGS. 46 and 47, indicated generally by the reference numeral 80, in which parts described with reference to the previous embodiment are assigned the same reference numerals. In this embodiment, the ring-engaging channel 71 is recessed into the body and has an aperture 81 between the channel 72 and channel 71 so that when the channel 71 is engaged with the ring 2 a top of the ring is disposed in the rail-engaging channel and contacts the rail. This illustrated in FIG. 56 which shows a sectional view of the ring 2, connector 80, and rail 61, and showing the ring contacting the rail when the connector is pitched inwardly.

Figure 58:
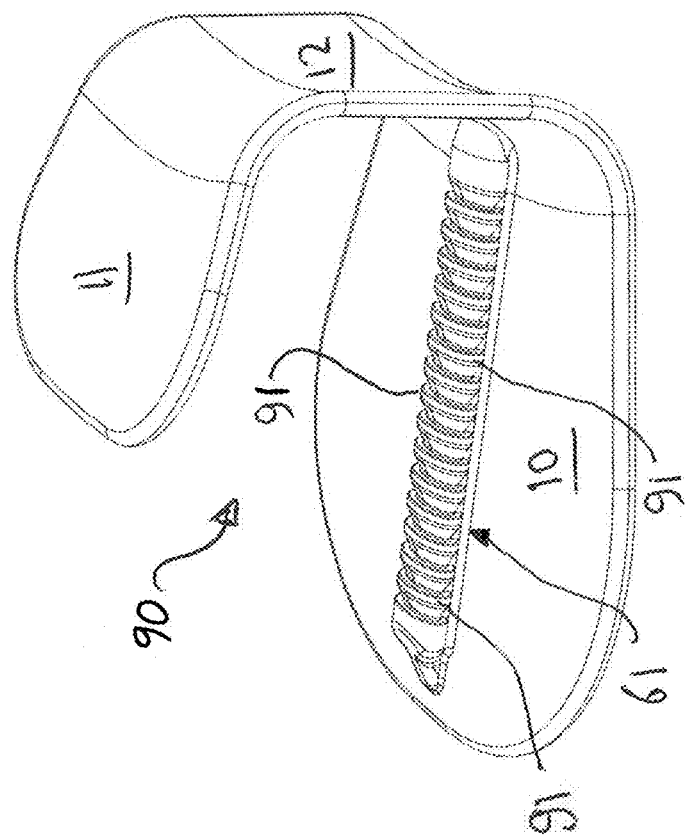
FIGS. 57 and 58 are perspective views of a radially adjustable retractor according to an alternative embodiment of the invention, in which the rail on the underside of the upper panel of the retractor has a series of teeth extending radially along the rail. Each tooth extends laterally across the top of the rail and in FIG. 57 the teeth have a straight saw-tooth profile and in FIG. 58 the teeth have a curved saw-tooth profile.
Figure 57:
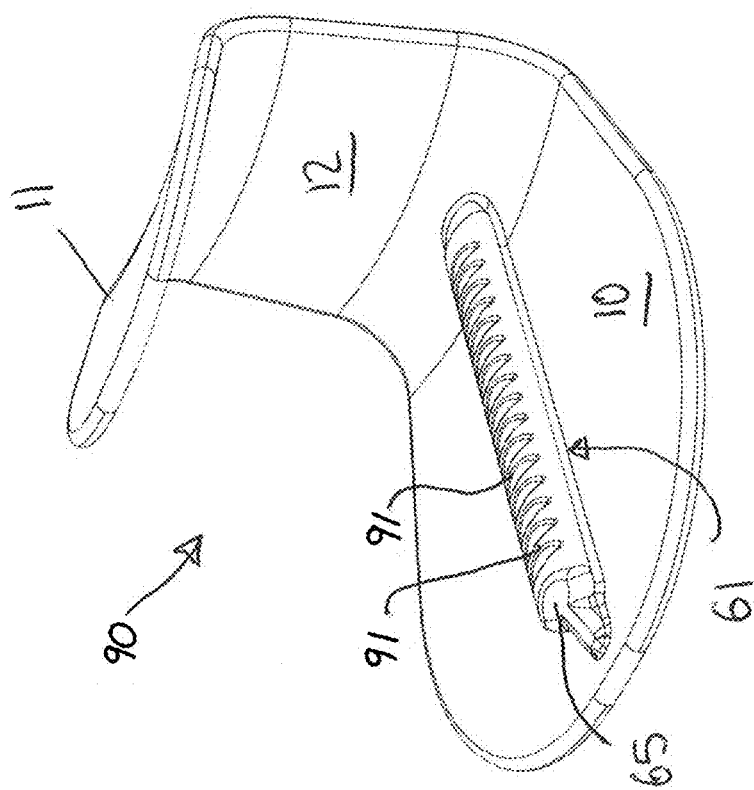

FIGS. 57 and 58 are perspective views of a radially adjustable retractor according to an alternative embodiment of the invention, indicated generally by the reference numeral 90, in which parts identified with reference to the previous embodiments are assigned the same reference numerals. In the embodiment, the head 65 of rail 61 on the underside of the upper panel 10 of the retractor has a series of teeth 91 disposed radially along the rail. Each tooth 91 extends laterally across the top of the rail. In FIG. 57 the teeth 91 have a straight saw-tooth profile and in FIG. 58 the teeth 91 have a curved saw-tooth profile.

Figure 60:
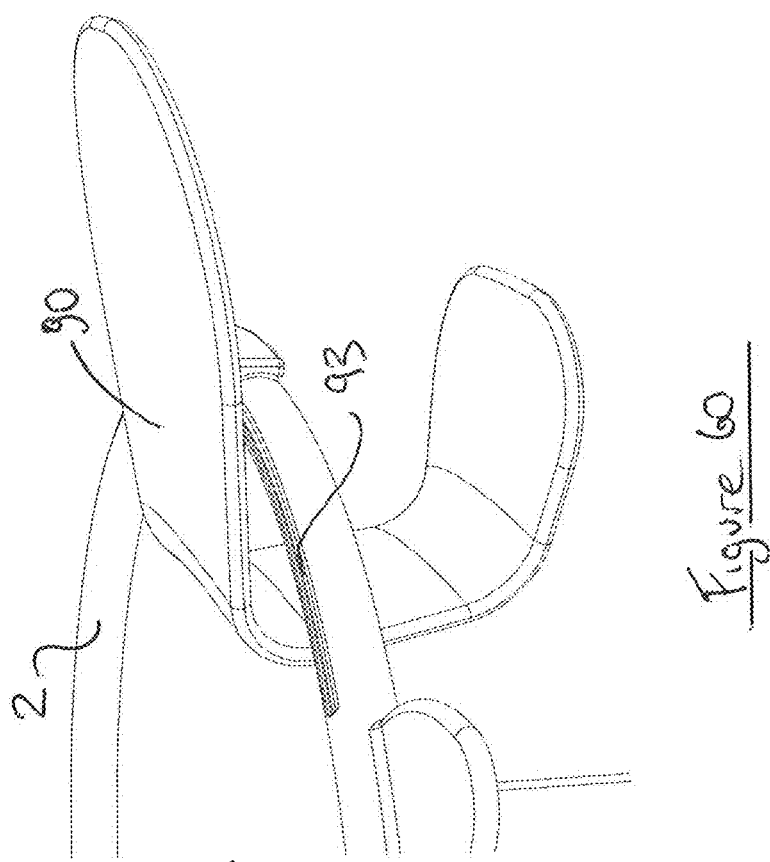
FIG. 60 is a perspective view from above of part of the system of FIG. 59.
Figure 59:
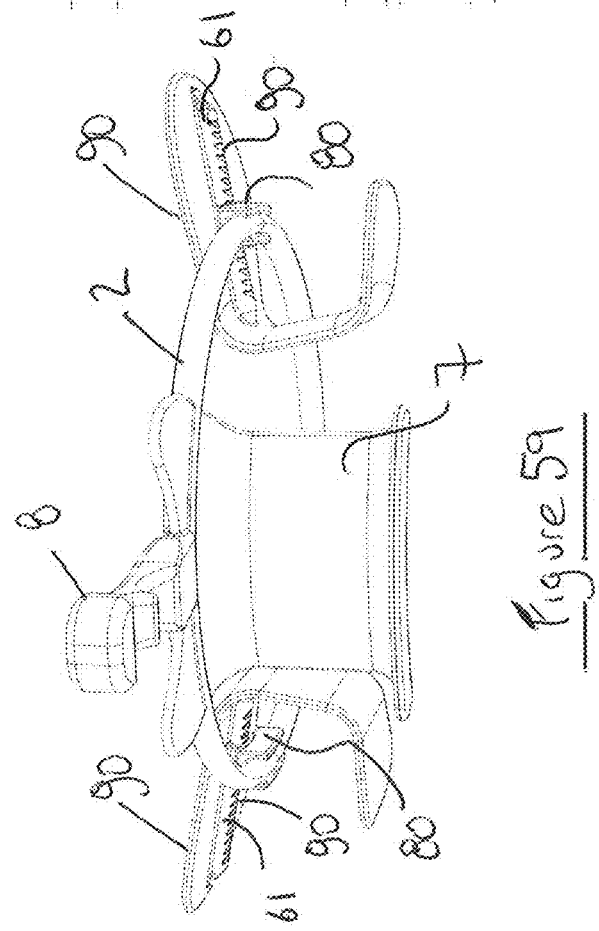
FIG. 59 is a perspective view from below of a system of the invention showing two radially adjustable retractors with integrated rail connected to the supporting ring via detachable connectors.

FIG. 59 is a perspective view from below of a system of the invention showing two radially adjustable retractors 90 with integrated rail 61 and teeth 91 connected to the supporting ring 2 via detachable connector 80. FIG. 60 is a perspective view from above of part of the system of FIG. 59 and showing a connecting ring 2 with a groove 93. FIGS. 61 to 63 are views of the system to FIG. 59 showing how a tooth 91 on the rail 61 of the retractor 90 engages and locks with the groove 93 formed on a top of the supporting ring 2 when the connector 80 is attached to the rail 61 and the supporting ring 2. This is best illustrated in FIGS. 64 and 65 which are sectional views showing the connector coupled to the supporting ring and the rail. In FIG. 64 the connector 80 and rail are rotated (i.e. pitched inwardly) relative to the ring 2 with the result that the teeth 91 are spaced apart from and do not engage with the groove 93 in the ring 2. This is an unlocked configuration allowing the rail and retractor to be slidably moved along the channel 71 to radially adjust the position of the retractor relative to the ring. In FIG. 65, the connector is not rotated (little or no pitch, which occurs when the retractor is released by the user) and a tooth 91 on the rail engages the groove 93 on the supporting ring, resulting in the rail, connector and supporting ring being locked in position. The lock may be released by adjusting the pitch of the retractor relative to the ring.

Figure 67:
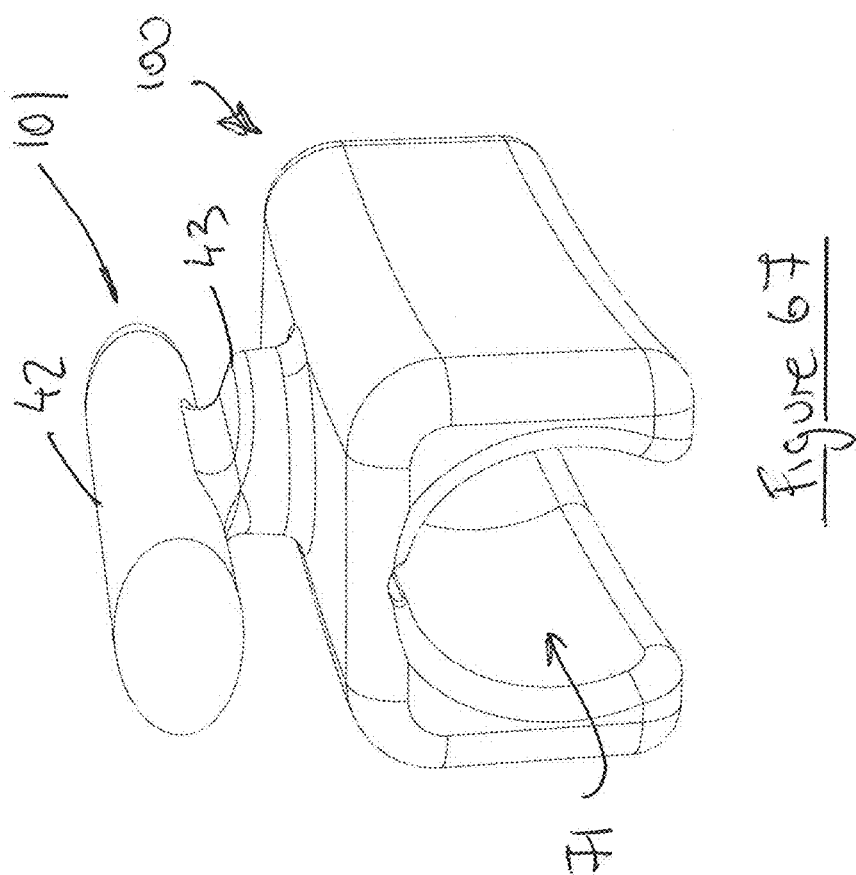
FIGS. 66 and 67 are perspective view of another detachable connector of the invention configured to snap-fit with the supporting ring and having a projecting T-shaped lug configured to engage a re-entrant slot on a retractor.
Figure 66:
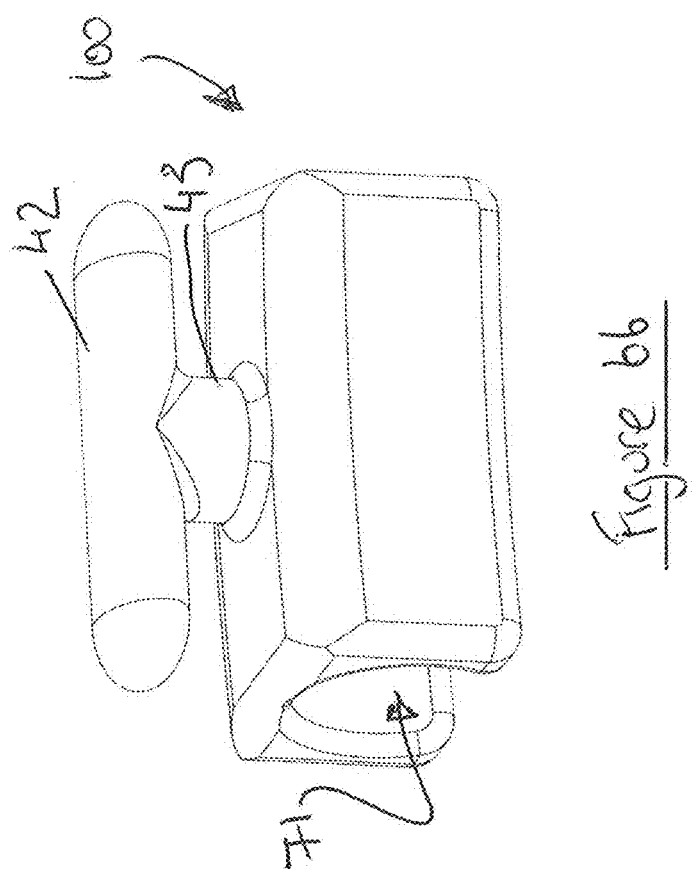

FIGS. 66 and 67 are perspective views of another detachable connector of the invention, indicated generally by the reference numeral 100, in which parts identified with reference to the previous embodiments are assigned the same reference numerals. In the embodiment, the detachable connector 100 is configured to snap-fit with the supporting ring 2 as described previously and couples to the retractor by means of a projecting T-shaped lug 101 configured to engage a re-entrant slot 44 on a retractor. The T-shaped lug and slots are substantially the same as those described previously and operate in the same way.

FIG. 68 shows a system of the invention incorporating a detachable connector 100 and showing how the detachable connector is circumferentially adjustable around the ring (arrow C) and how the connector allows radial adjustment of the retractor 3 relative to the ring 2 (arrow R).

FIG. 69 shows a radially adjustable retractor 3 attached to a supporting ring 2 with the detachable connecter 100, where the retractor is attached to the T-shaped lug 40 of the connector via its radially innermost slot 44D (full retraction).

Figure 71:
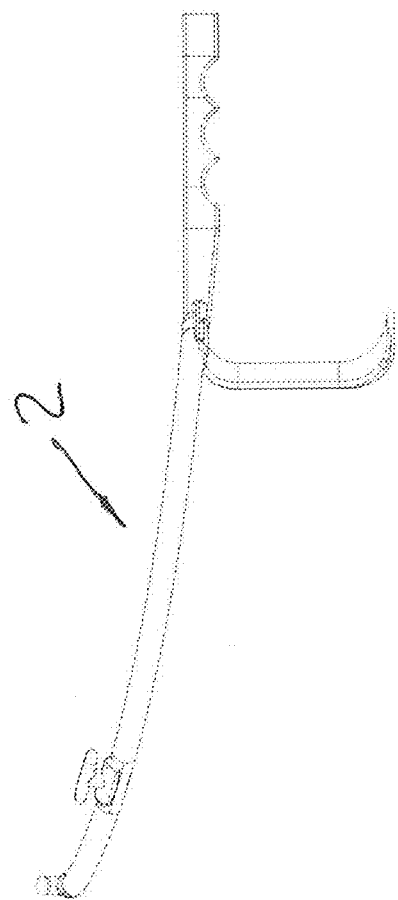
FIGS. 70 and 71 are side perspective and elevational view of a supporting ring according to an alternative embodiment of the invention, in which the supporting ring has a curved profile.
Figure 70:
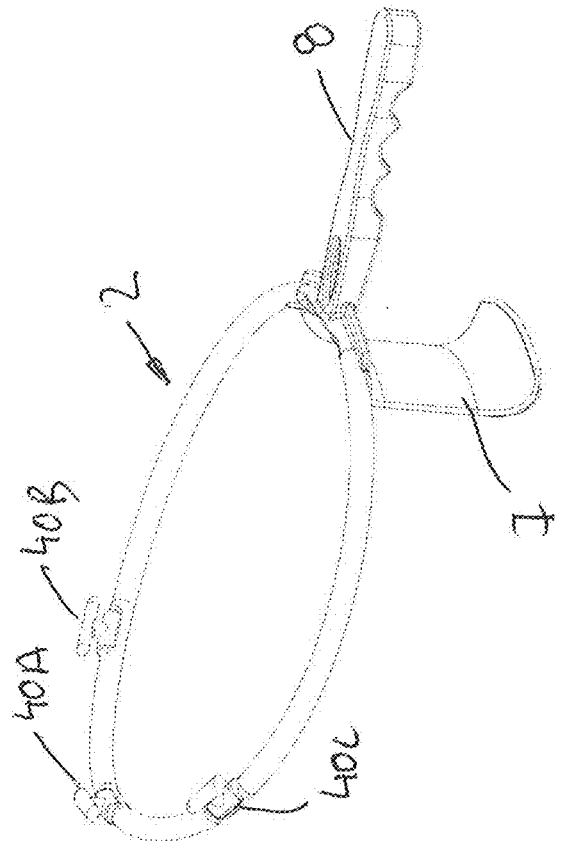

FIGS. 70 and 71 are side perspective and elevational view of a supporting ring 2 according to an alternative embodiment of the invention, in which the supporting ring has a curved profile.

Figure 73:
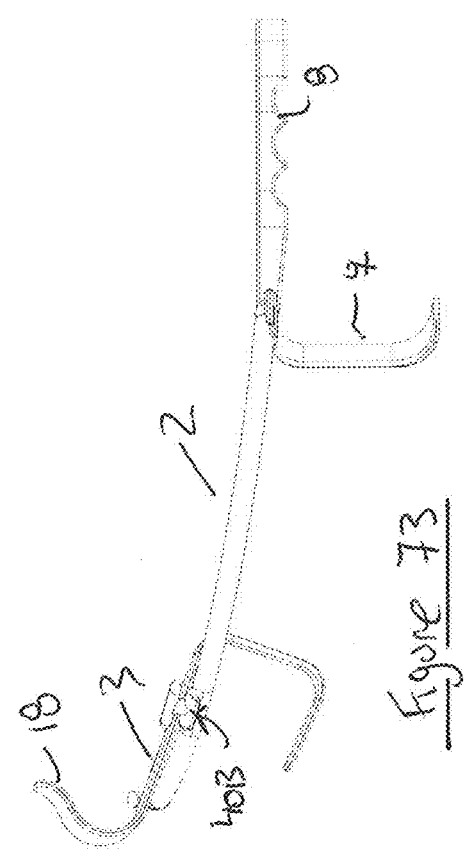
FIGS. 72 to 75 are side elevational views of supporting rings of the invention.
Figure 75:
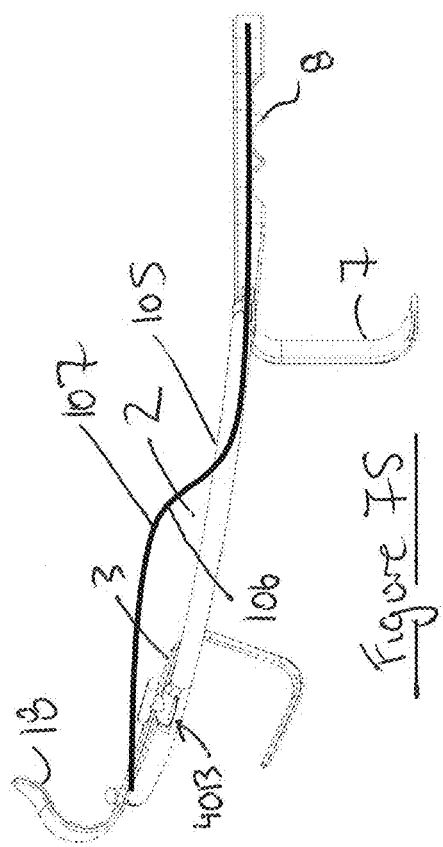
Figure 72:
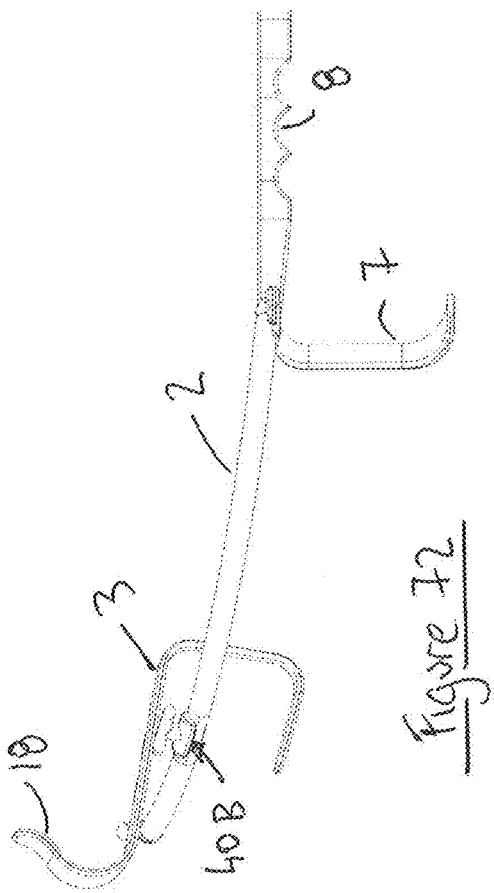
Figure 74:
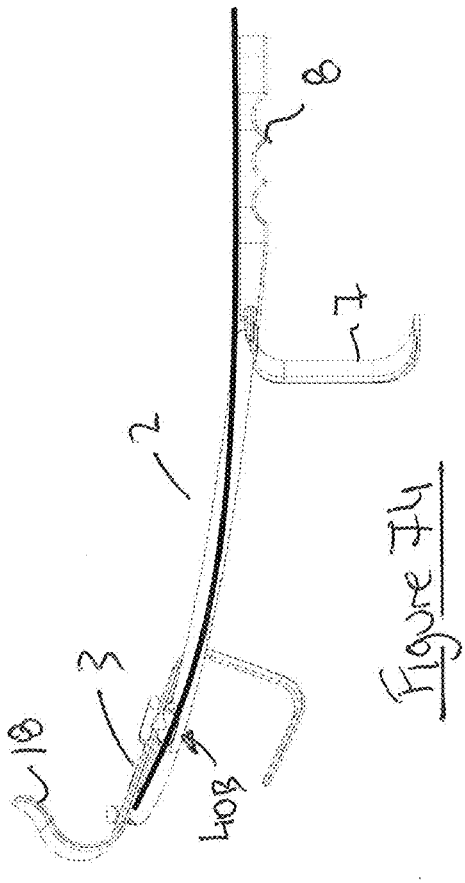

FIGS. 72 to 75 are side elevational views of supporting rings of the invention. In FIGS. 72 and 73, the supporting ring 2 has a curved profile that curves upwardly from the fixed retract end of the ring to an opposite end of the ring with the lip 18. In FIGS. 74 and 75, the curvature of the ring may have a first upward inflection 105 and second downward inflection 106 as illustrated by the bold line 107.

Figure 77:
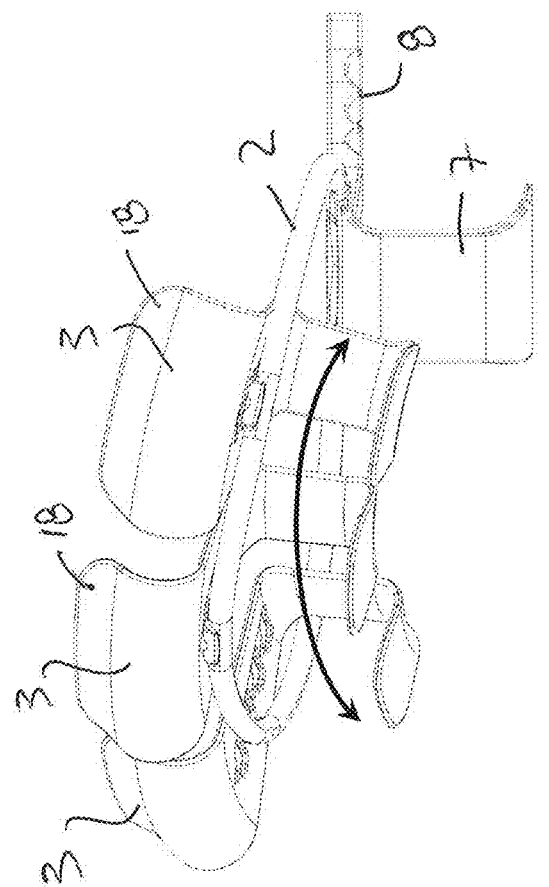
FIGS. 76 and 77 are perspective views from below of a system of the invention comprising a curved supporting ring and showing how the system can follow the curvature of the patient indicated by the arrows.
Figure 76:
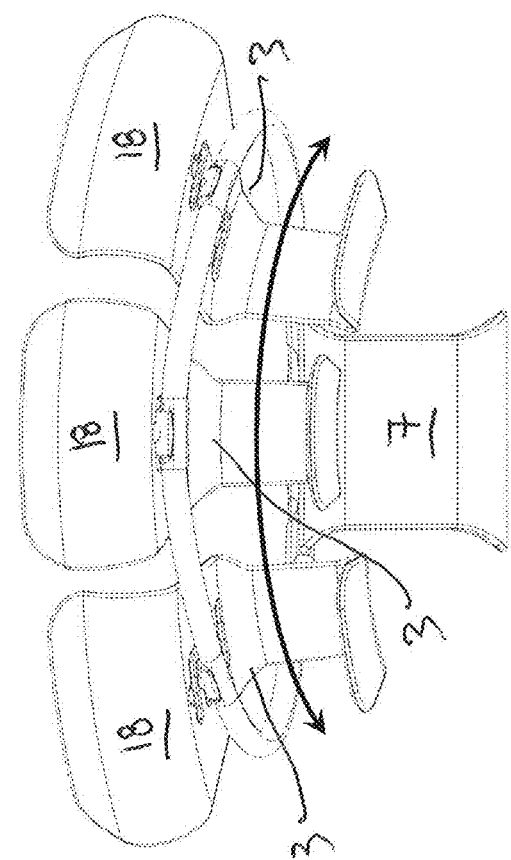

FIGS. 76 and 77 are perspective views from below of a system of the invention comprising a curved supporting ring and showing how the system can follow the curvature of the patient indicated by the arrows.

Figure 79:
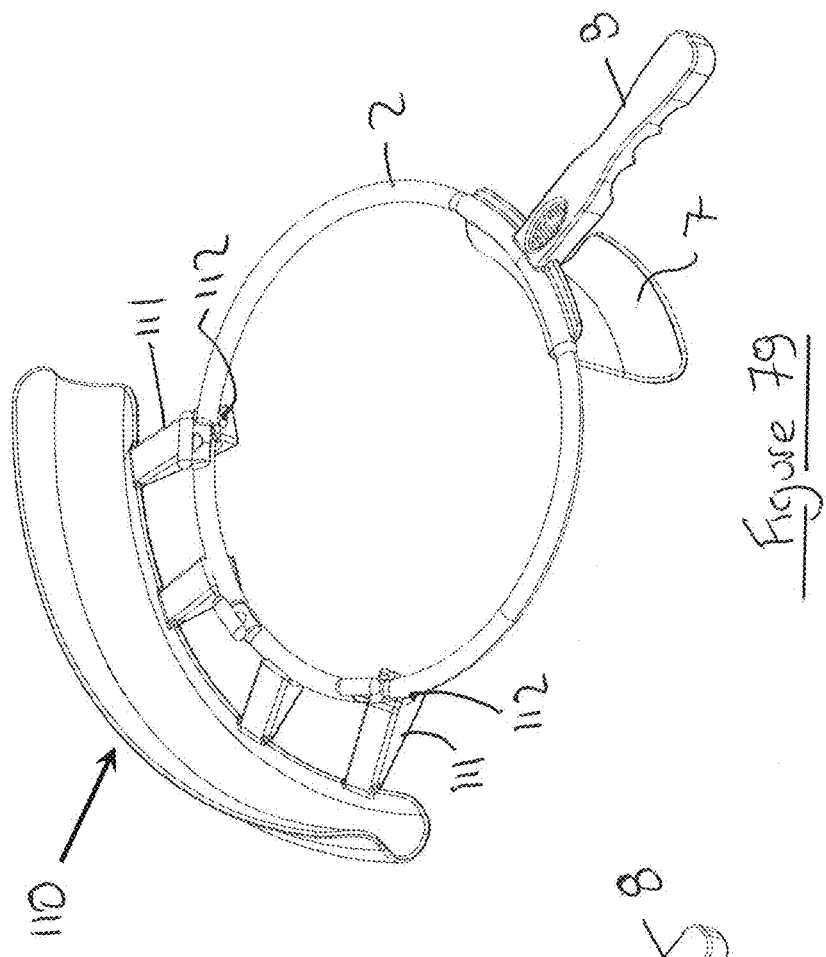
Figure 76:
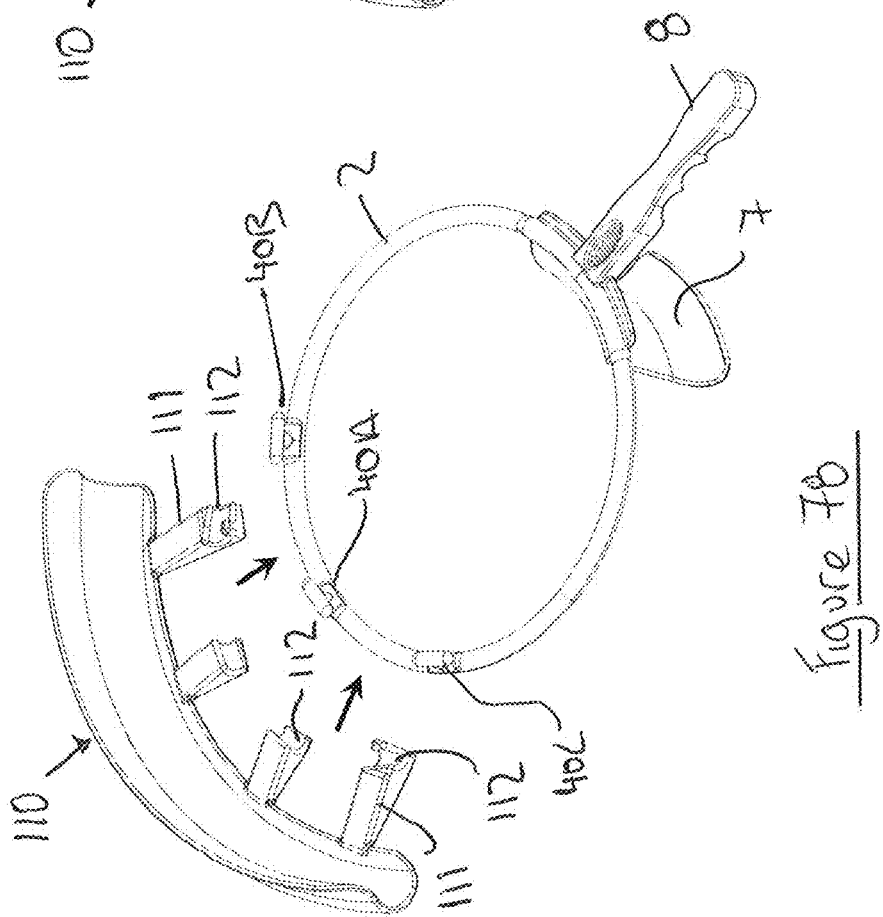

FIGS. 78 and 79 are elevational views of a system according to an alternative embodiment of the invention that incorporates a detachable elongated panniculus deflecting panel 110 configured for attachment to the ring outside and curved around a section of the ring opposite to the fixed retractor 7. In profile the panel 110 has the same s-shaped profile as illustrated previously for the integral lip 18, and has connecting arms 111 projecting radially inwardly with snap-fit connectors 112 on a distal end of each arm configured for snap-fit engagement with the connecting ring 2. The panel 110 is shown prior to attachment to the ring 2 in FIG. 78, and after attachment to the ring in FIG. 79.

FIGS. 80 and 81 are perspective views of a radially adjustable retractors 3 without a panniculus deflecting lip and for use with a system comprising a detachable panniculus deflecting panel 110. Apart from the absence of an integrally formed panniculus deflecting lip 18, the retractors 3 are substantially the same as those described previously.

FIG. 82 is a perspective view of the system of FIG. 79 with the radially adjustable retractor 3 attached to the ring 3 by an integrally formed T-shaped lug 40A which engages the radially outermost slot 44A and the panniculus deflecting panel 110 attached to the ring 2 by the arms 111 and connectors 112.

Figure 84:
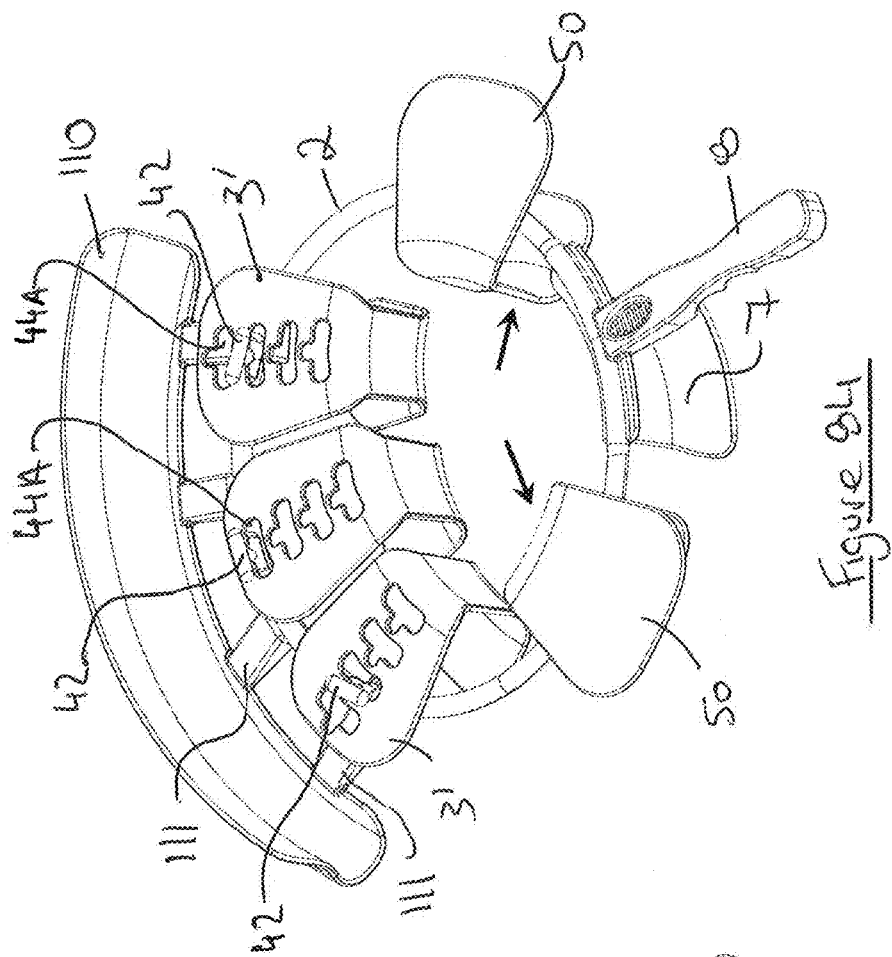
FIGS. 83 and 84 are perspective views of the system of FIG. 82 shown with additional radially adjustable retractors attached to the supporting ring.
Figure 83:
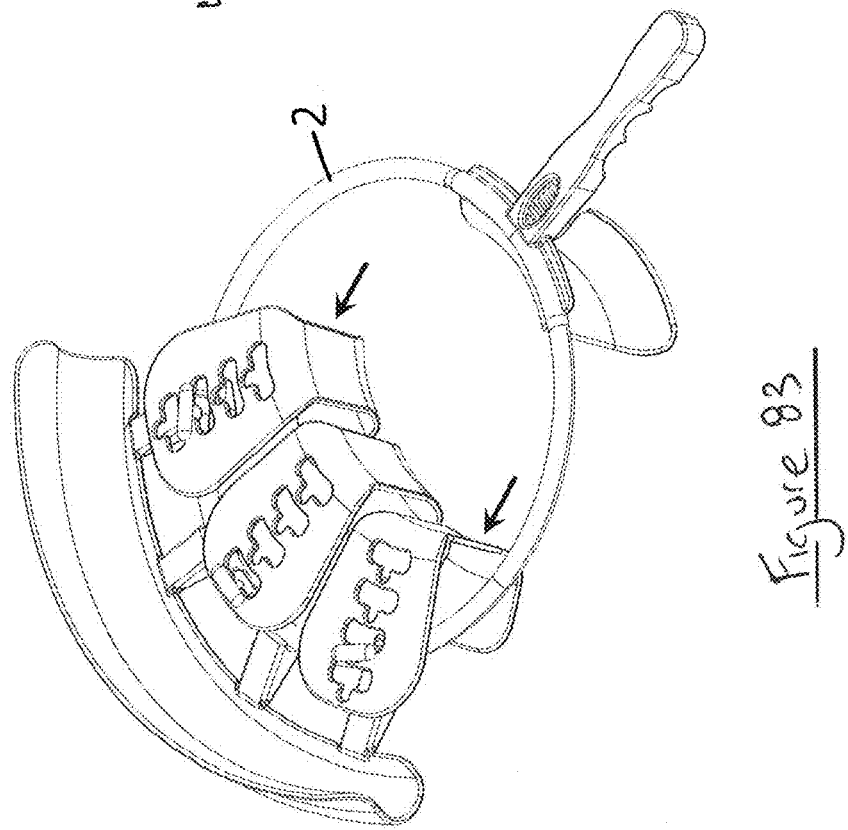

FIGS. 83 and 84 are perspective views of the system of FIG. 82 shown with additional radially adjustable retractors 3' and 50 attached to the supporting ring as described previously.

FIGS. 85 and 86 are perspective views of a radially adjustable retractor 3 with a hydrophilic surface coating 120 configured to absorb water making the surface slippery to aid passage of a neonate during delivery.

Figure 88:
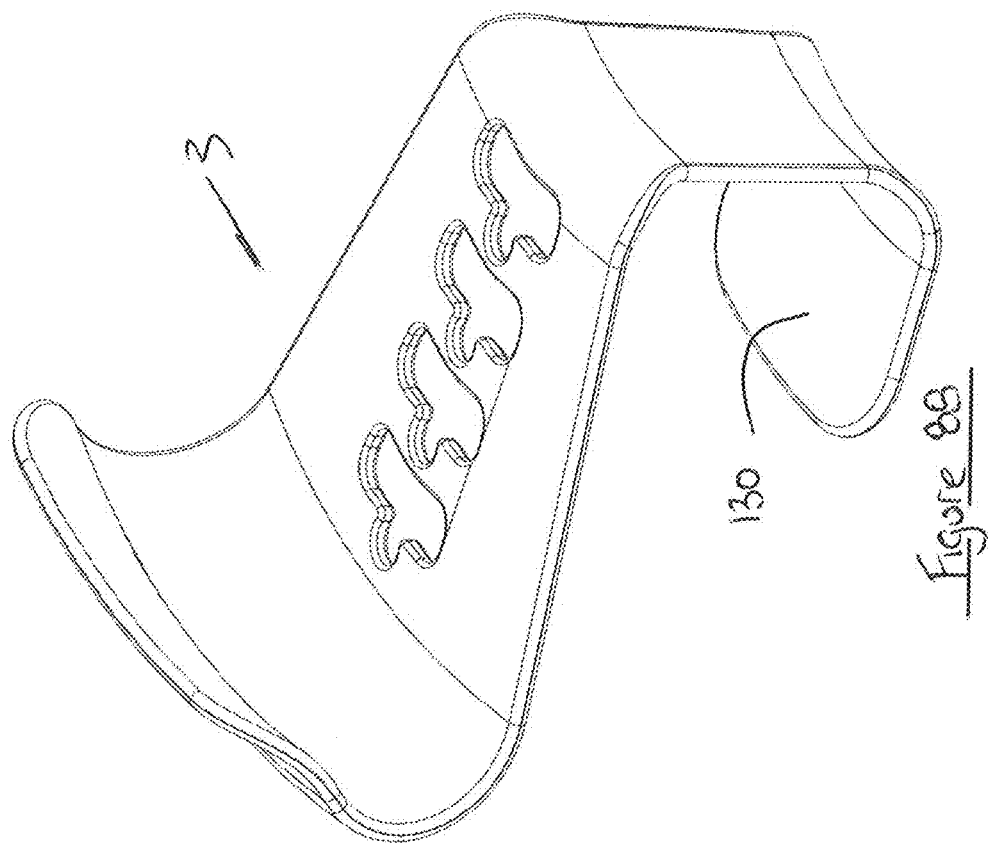
FIGS. 87 and 88 are perspective view of a radially adjustable retractor with parts of the tissue-engaging surface of the retractor incorporating a roughened surface to improve purchase on the tissue.
Figure 87:
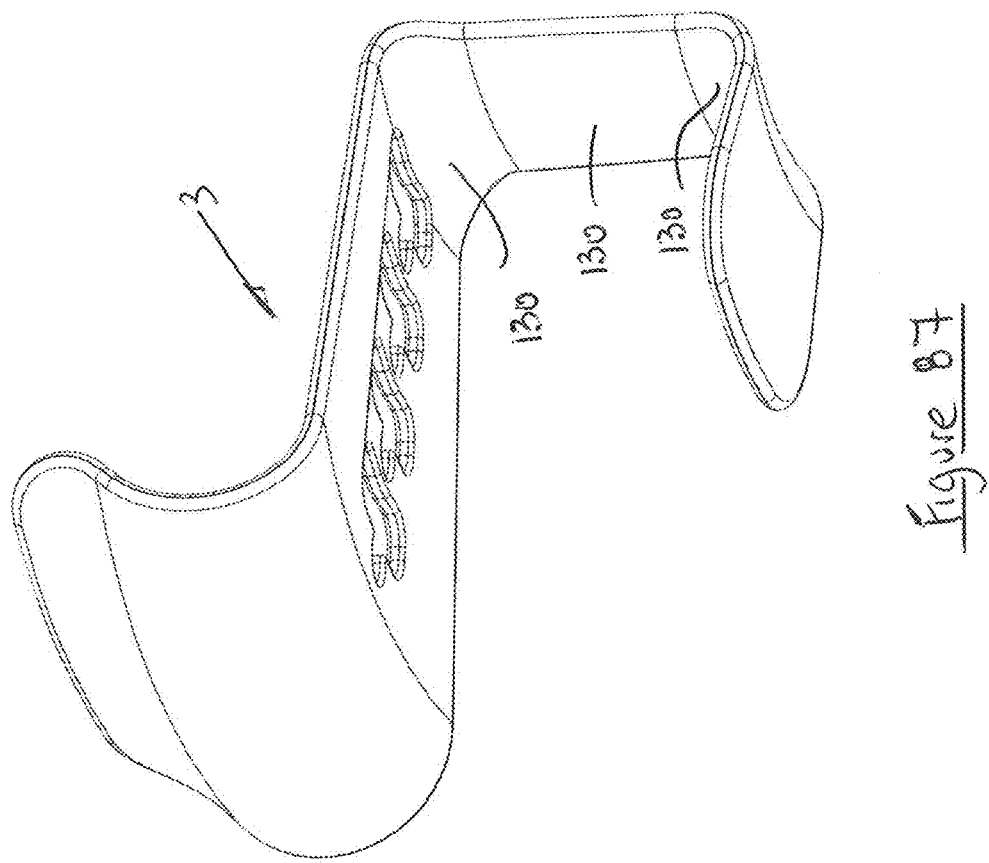

FIGS. 87 and 88 are perspective view of a radially adjustable retractor 3 with parts of the tissue-engaging surface of the retractor incorporating a roughened surface 130 to improve purchase when contacting abdominal tissue.

FIG. 89 is a side elevational view of a retractor showing how the lower panel 11 tapers upwardly away from the incision which assists the retractor grip or clasp abdominal tissue during use. The retractor 3 is also sufficiently resiliently deformable to allow the lower panel 11 flex upwardly and downwardly during use (arrow A)

FIG. 90 shows how the height h of the rear panel of the retractor can be varied during manufacture to take account of patients having abdominal tissue of different thickness.

Figure 91B:
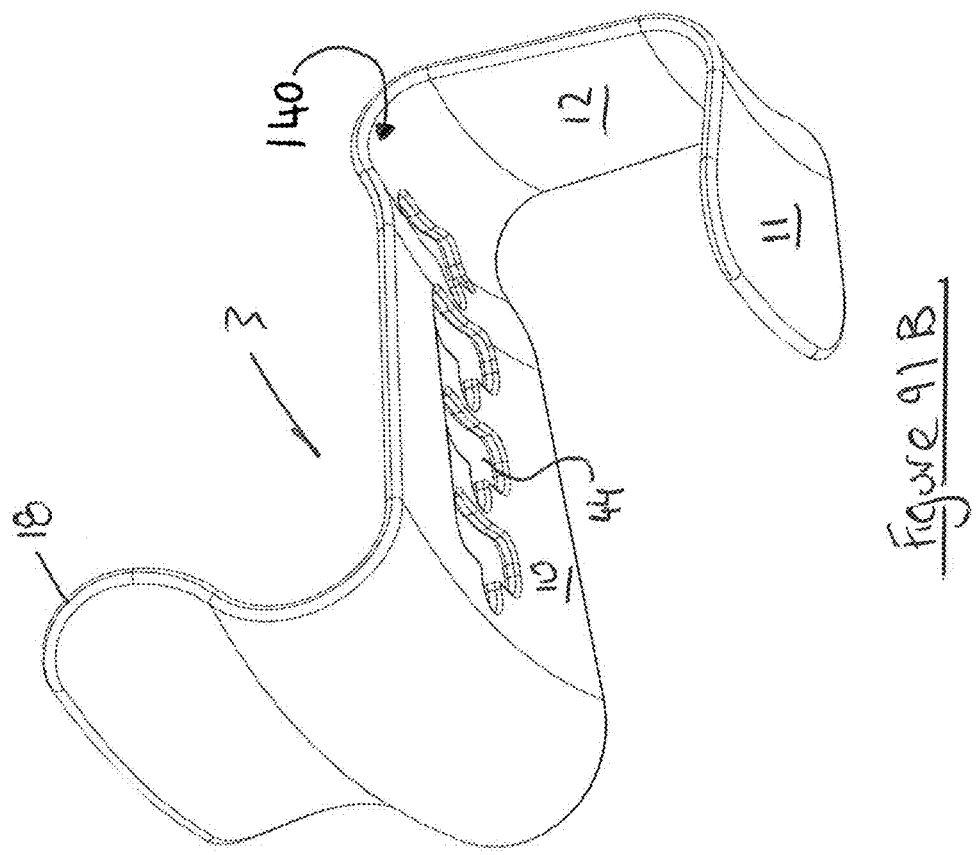
FIGS. 91A and 91B are perspective views of a radially adjustable paddle having an extended panniculus deflecting element and a skin incision stress relieving pocket formed at the inflection point between the upper and rear panels.
Figure 91A:
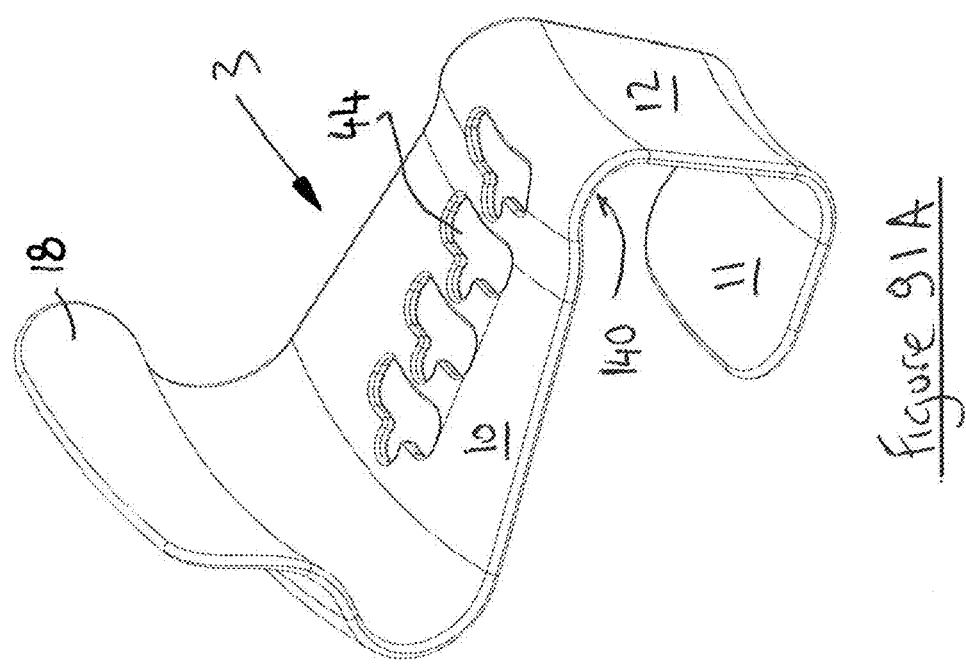
Figure 93:
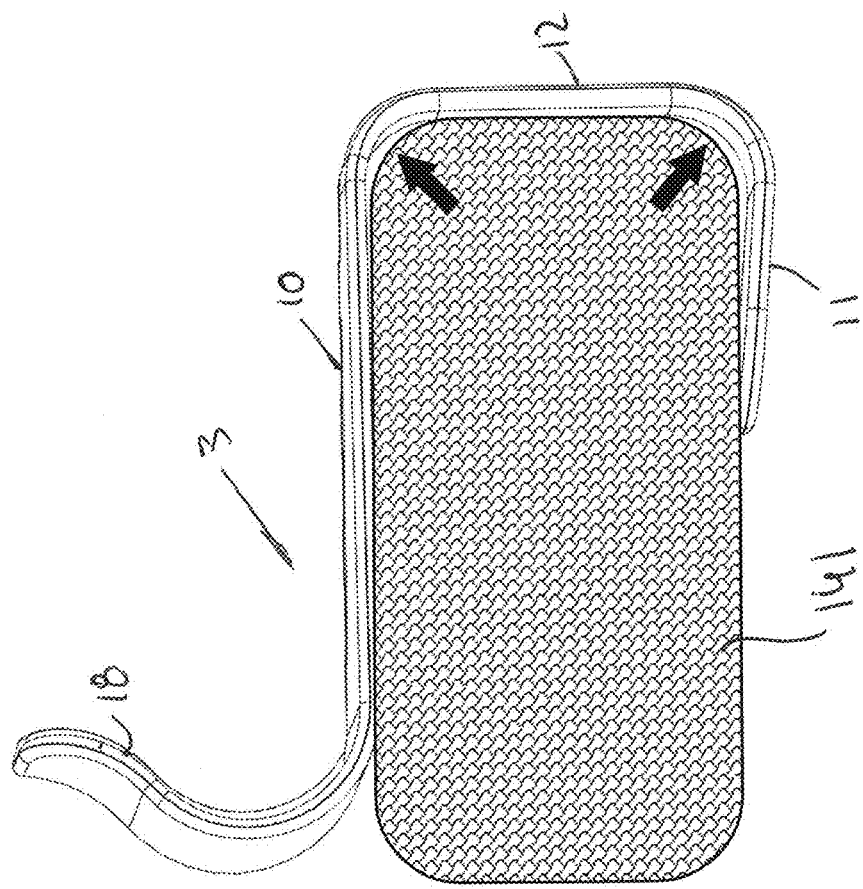
FIGS. 92 and 93 are sectional views of a retractor without a stress relieving pocket engaging and clasping abdominal tissue via an incision. The rectangular shape represents a cross-section through the abdominal wall. The arrow in FIG. 92 represents the direction of movement, as the paddle clasps and lifts open the abdominal incision. With the Pivot Paddle retracting the abdominal tissue under load, (which would also be the case with standard retractors) the edges of the abdominal tissue experience a higher degree of compression, due to the internal profile of the paddle (areas of increased tissue compression denoted by the arrows in FIG. 93). Increased levels of tissue compression are experienced, most especially the external layers of skin, where compression can lead to compromised blood flow within the tissue layers and subsequently increase the risk of tissue necrosis, depending on the duration of compression.
Figure 92:
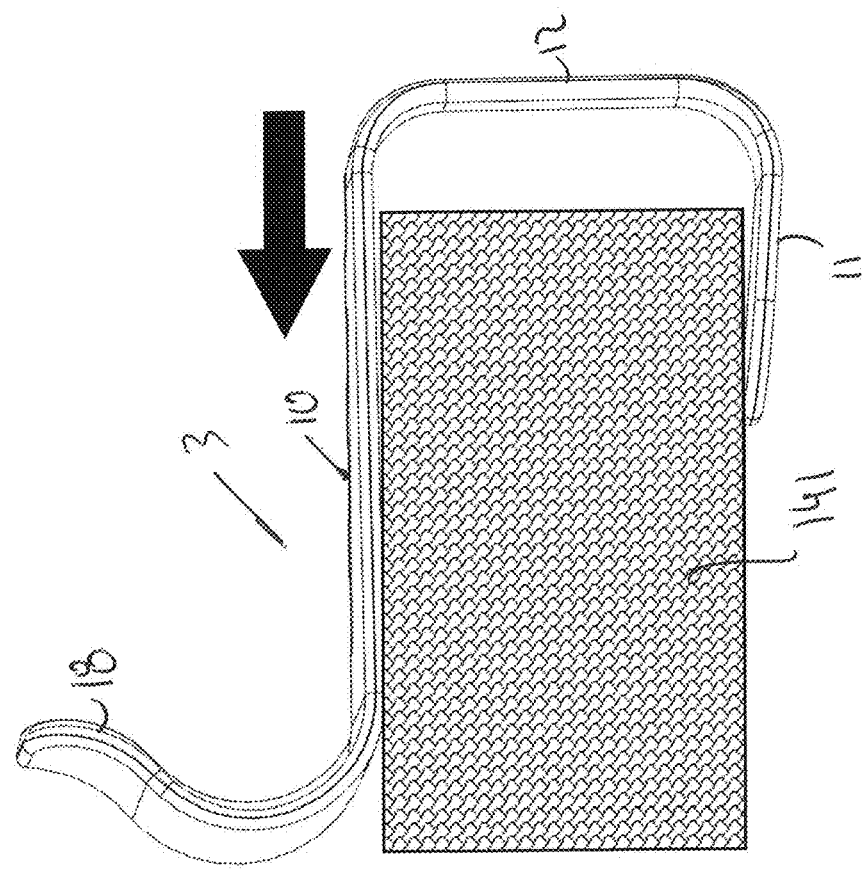
Figure 94:
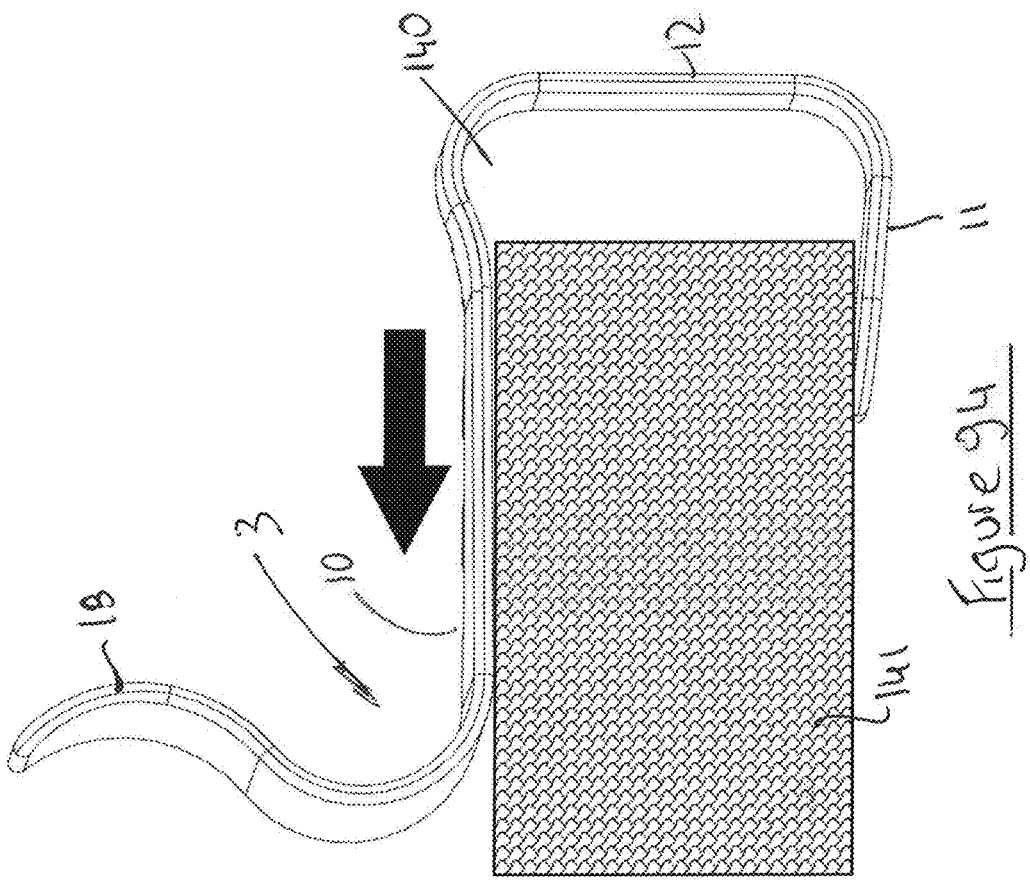

FIGS. 91A and 91B are perspective views of a radially adjustable paddle 3 having an extended panniculus deflecting element 18 and a skin incision stress relieving pocket 140 formed at the inflection point between the upper and rear panels 10, 12. FIGS. 92 to 94 show the configuration and technical effect of the stress relief pocket 140. First, FIGS. 92 and 93 are sectional views of a retractor 3 without a stress relieving pocket 140 engaging and clasping abdominal tissue 141 via an incision. The rectangular shape represents a cross-section through the abdominal wall. The arrow in FIG. 92 represents the direction of movement, as the retractor 3 clasps and lifts open the abdominal incision. With the retractor 3 retracting the abdominal tissue under load, (which would also be the case with standard retractors) the edges of the abdominal tissue experience a higher degree of compression, due to the internal profile of the paddle (areas of increased tissue compression denoted by the arrows in FIG. 93). Increased levels of tissue compression are experienced, most especially the external layers of skin, where compression can lead to compromised blood flow within the tissue layers and subsequently increase the risk of tissue necrosis, depending on the duration of compression.

Figure 95:
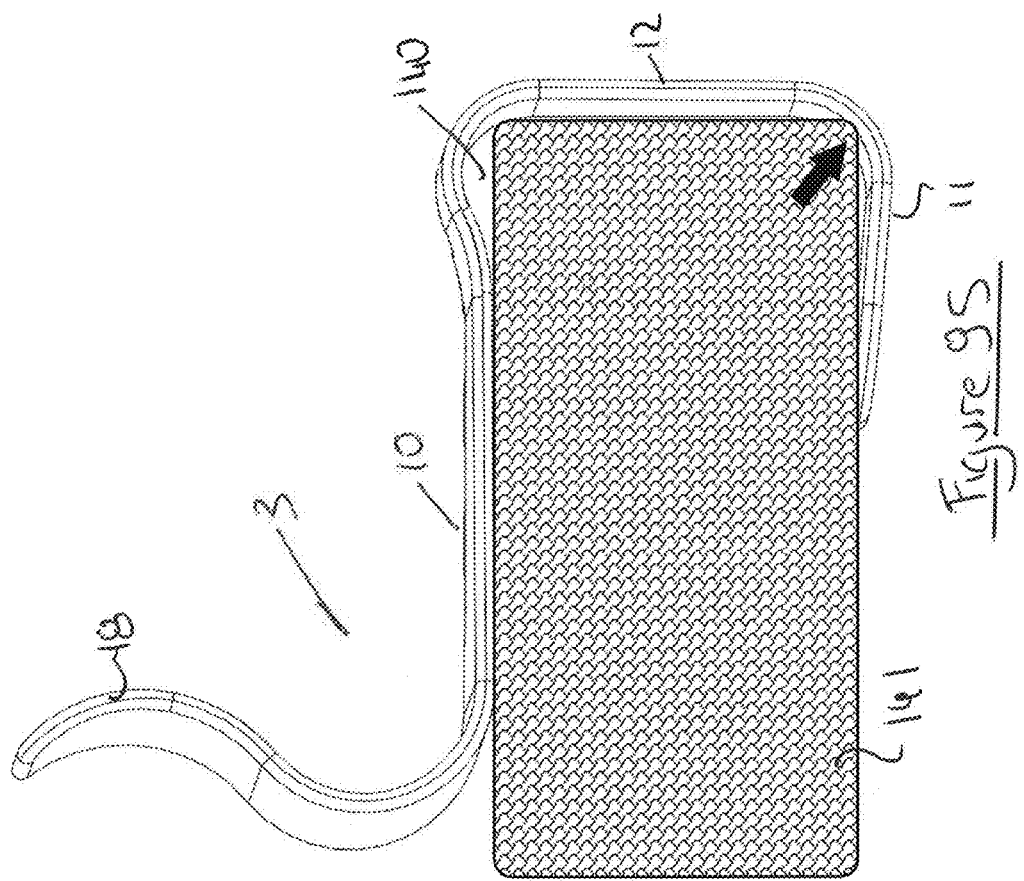
FIGS. 94 and 95 are sectional views of a retractor including a stress relieving pocket engaging and clasping abdominal tissue via an incision. The Stress-Relief Element of this paddle provides a pocket for the tissue edge, whereby the level of tissue compression is significantly reduced, due to the geometric shape of the paddle. This reduction in tissue compression therefore reduces the risks associated with restricted blood flow and the resultant tissue damage. The top arrow in FIG. 93 represents the external epidermis layers, where the most benefit will be attained from the stress-relief feature. The bottom arrow would still be under the same degree of compression as the retractor of FIG. 93, however, the internal layers do not present the same risk of necrosis. A further stress-relief feature could be incorporated for the internal tissue edge, if deemed appropriate.

FIGS. 94 and 95 are sectional views of a retractor including a stress relieving pocket engaging and clasping abdominal tissue via an incision. The Stress-Relief Element of this paddle provides a pocket for the tissue edge, whereby the level of tissue compression is significantly reduced, due to the geometric shape of the paddle. This reduction in tissue compression therefore reduces the risks associated with restricted blood flow and the resultant tissue damage. The top arrow in FIG. 93 represents the external epidermis layers, where the most benefit will be attained from the stress-relief feature. The bottom arrow would still be under the same degree of compression as the retractor of FIG. 93; however, the internal layers do not present the same risk of necrosis. A further stress-relief feature could be incorporated for the internal tissue edge, if deemed appropriate.

Figure 97:
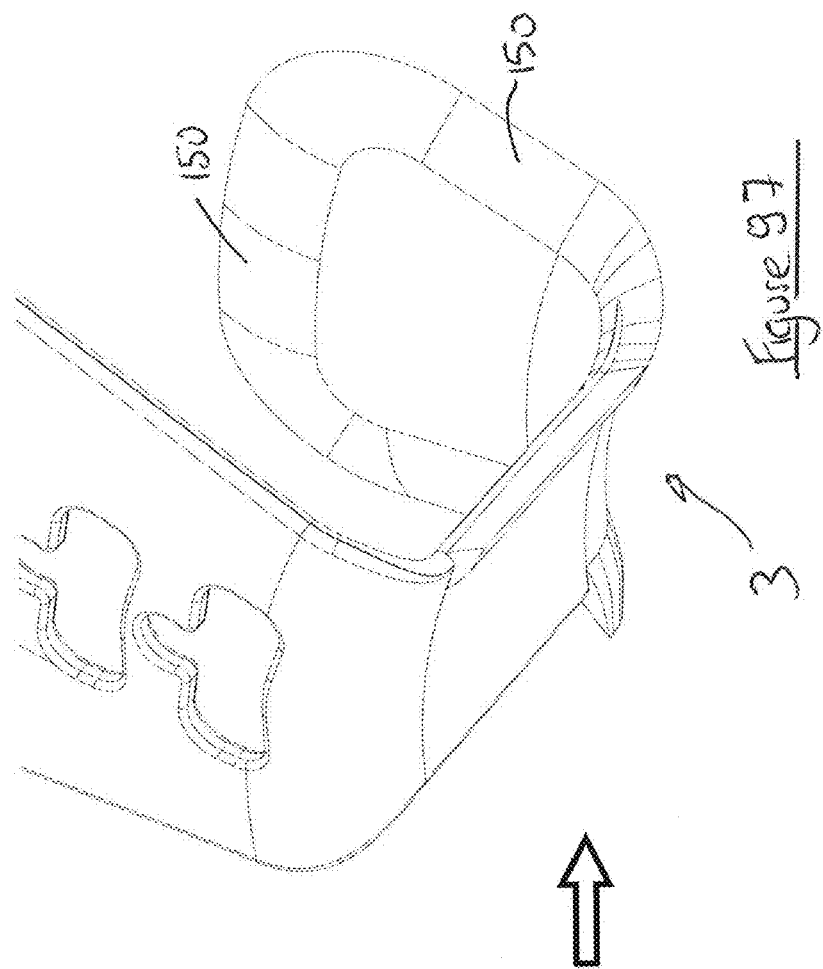
FIGS. 96 and 97 are sectional elevational views of a radially adjustable retractor with soft elastomeric or silicone edging.
Figure 96:
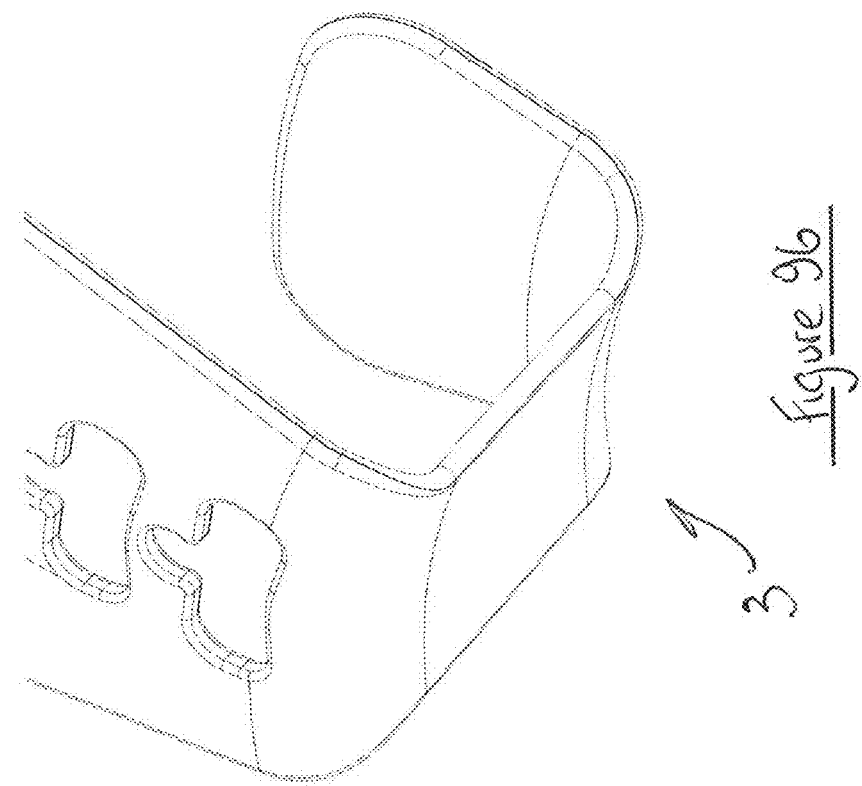
Figure 9A:
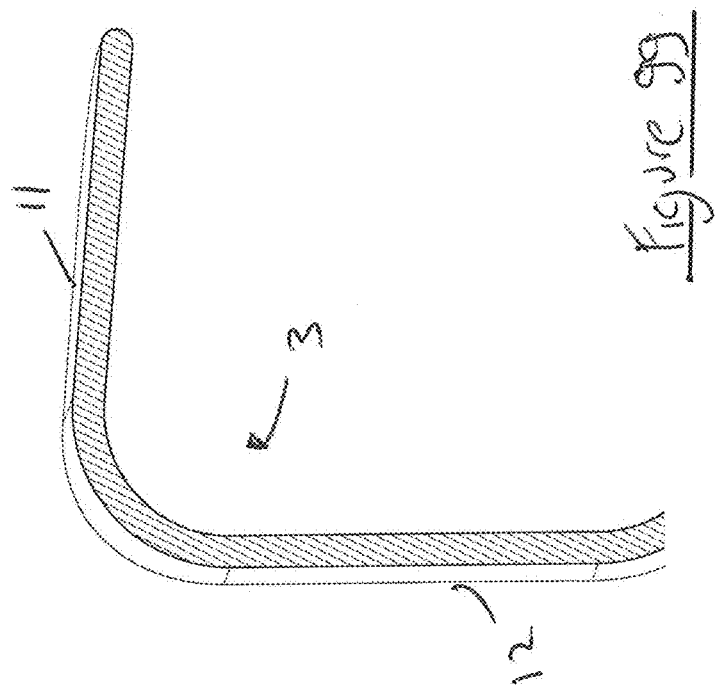
Figure 9B:
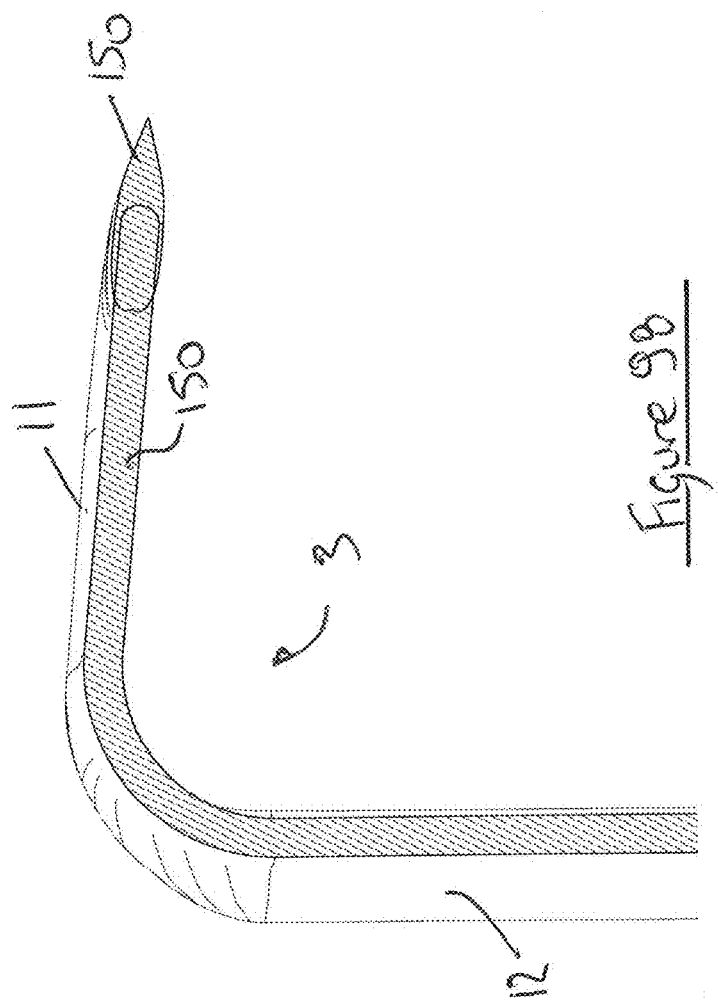

FIGS. 96 and 97 are sectional elevational views of a radially adjustable retractor 3 without (FIG. 96) and with (FIG. 97) soft elastomeric or silicone edging 150. FIG. 98 is a side elevational view of the retractor of FIG. 96 with the edging and FIG. 99 is a side elevational view of a retractor without the soft elastomeric or silicone edging.

Figure 100:
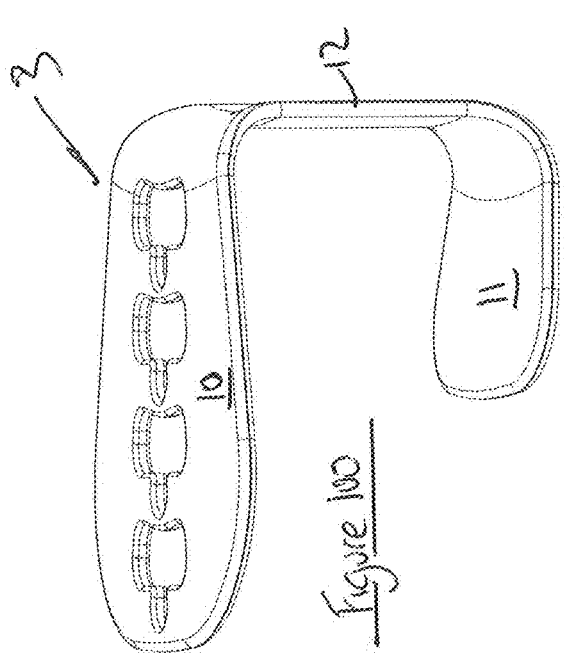
FIGS. 100 and 101 are perspective and side elevational views of a radially adjustable retractor (for reference).
Figure 101:
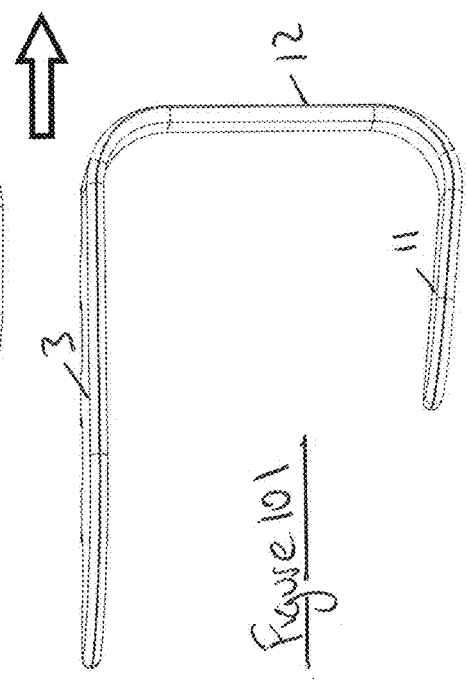

FIGS. 100 and 101 are perspective and side elevational views of a radially adjustable retractor without a panniculus deflecting lip.

Figure 102:
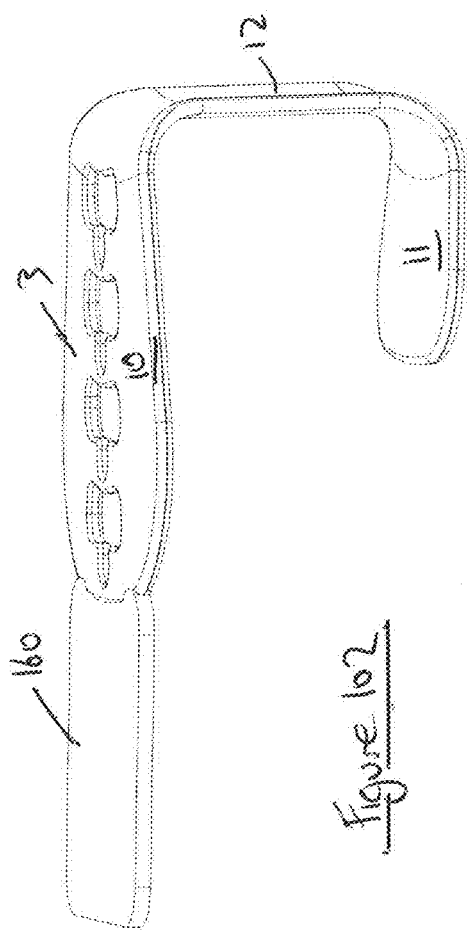
FIGS. 102 and 103 are perspective and side elevational views of a radially adjustable retractor with an adjustable panniculus deflecting lip that can be shaped by the user.
Figure 103:
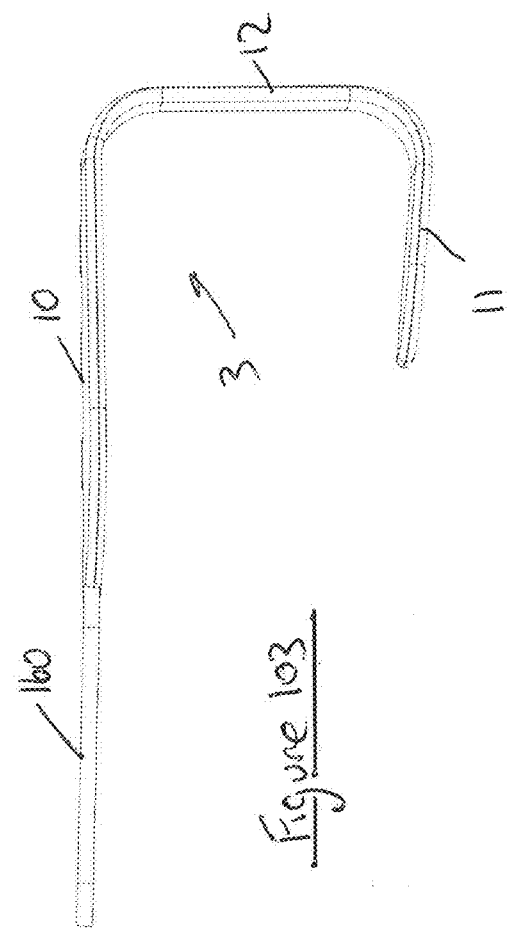

FIGS. 102 and 103 are perspective and side elevational views of a radially adjustable retractor 3 with an adjustable panniculus deflecting lip 160 that can be shaped by the user. FIGS. 104 and 105 are perspective views of the retractor of FIG. 102 with the panniculus deflecting lip being formed into two different shapes.

FIGS. 106 and 107 are perspective views of the retractor 3 prior to attachment to a supporting ring showing how the shapeable lip 160 can be formed into a panniculus shape prior to attachment to the ring 2.

Figure 109:
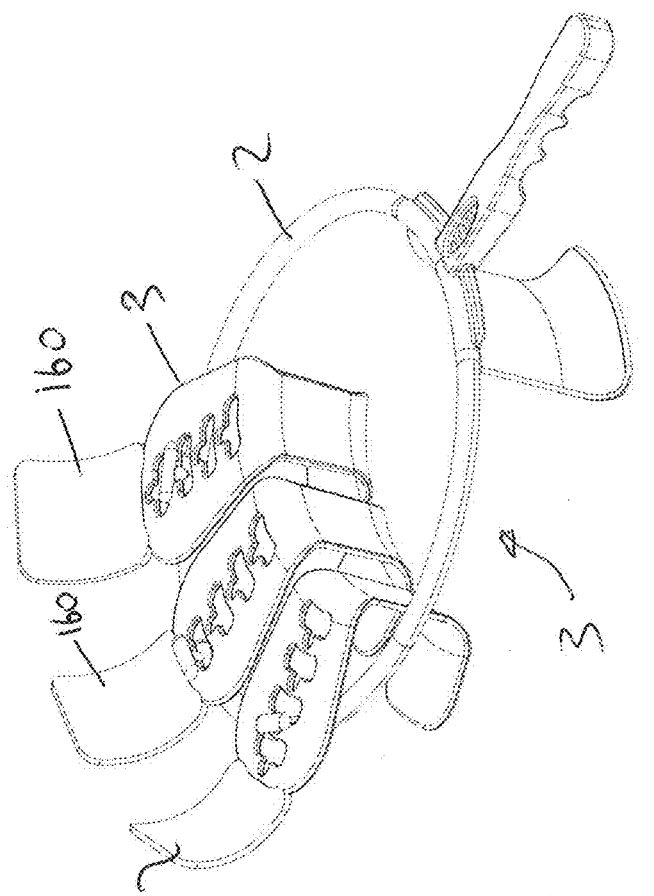
FIGS. 108 and 109 are perspective views of the retractor of FIG. 104 attached to a supporting ring.
Figure 108:
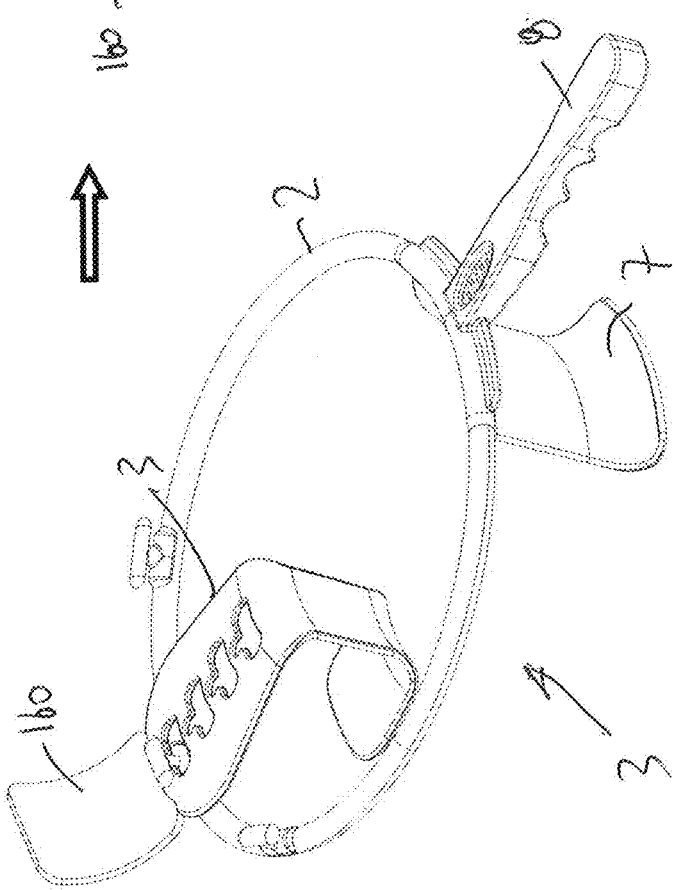

FIGS. 108 and 109 are perspective views of the retractor of FIG. 104 attached to a supporting ring and FIG. 110 is a perspective view of a system of the invention with a number of retractors each having an adjustable panniculus deflecting lip 160 which is deployed upwardly in three of the retractors and folded down out of the way in two of the retractors.

FIG. 111 illustrates the use of a system of the invention to hold back an obese woman's panniculus during a Caesarean section procedure. The image shows the ring 3 anchored to the woman's abdomen by the fixed retractor 7 and opposed retractor 3, and the panniculus deflecting lip 18 holding the panniculus of the woman and keeping it out of the surgical field for the duration of the procedure.

EQUIVALENTS

The foregoing description details presently preferred embodiments of the present invention. Numerous modifications and variations in practice thereof are expected to occur to those skilled in the art upon consideration of these descriptions. Those modifications and variations are intended to be encompassed within the claims appended hereto.

What is claimed is:

1. A surgical access system adapted to facilitate access to a neonate through a Caesarean incision in a patient's abdomen by holding open the incision, the system comprising:
    a supporting ring dimensioned to allow delivery of the neonate through the supporting ring;
    a non-adjustable retractor fixed to the supporting ring comprising an atraumatic lower portion, the non-adjustable retractor configured to cover and hold back a bladder during a Caesarean section procedure;
    an outwardly projecting handle fixed to the supporting ring adjacent the non-adjustable retractor;
    at least one radially adjustable retractor comprising a saddle shape configured to cup and manually retract a section of abdominal tissue at the incision, wherein the radially adjustable retractor comprises an atraumatic lower portion; and
    one or more first coupling elements positioned on the supporting ring, the coupling element configured for retrofitting the at least one radially adjustable retractor to the supporting ring in a tissue-retracting position, to thereby facilitate access to the neonate.

2. A surgical access system according to claim 1, wherein the first coupling element comprises a first formation disposed on a top of the supporting ring and the radially adjustable retractor comprises a second coupling element comprising a corresponding second formation on the radially adjustable retractor configured to couple with the first formation, wherein the first formation and the second formation are configured to allow the radially adjustable retractor to move in a pitch direction and/or a yaw direction relative to the supporting ring when the radially adjustable retractor is fitted to the supporting ring in a tissue retracting position.

3. A surgical access system according to claim 2, in which the first formation and the second formation are configured to allow the radially adjustable retractor to achieve a degree of roll relative to the supporting ring when the retractor is fitted to the supporting ring in a tissue retracting position.

4. A surgical access system according to claim 2, in which the first formation on the supporting ring is a projecting lug and the second formation on the radially adjustable retractor is a lug-receiving slot.

5. A surgical access system according to claim 2, in which the first formation on the supporting ring is a projecting lug and the second formation on the radially adjustable retractor is a lug-receiving slot, and in which the lug-receiving slot comprises a radially inward slot portion dimensioned to receive the lug and a radially outward slot portion configured for snap-fit engagement with the lug.

6. A surgical access system according to claim 2 in which the first formation on the supporting ring is a projecting lug and the second formation on the radially adjustable retractor is a lug-receiving re-entrant slot, in which the lug-receiving slot comprises a radially inward slot portion dimensioned to receive the lug and a radially outward slot portion configured for snap-fit engagement with the lug, in which the lug comprises a stem part dimensioned for snap-fit engagement with the radially outward slot portion and a head part that is oversized in relation to the radially outward slot portion but dimensioned to fit comfortably through the radially inward slot portion, and in which the radially inward slot portion is dimensioned to receive the head part when the head part is misaligned with the radially inward slot portion by up to 10° in the yaw direction.

7. A surgical access system according to claim 1, comprising at least two radially adjustable retractors.

8. A surgical access system according to claim 1, in which the radially adjustable retractor comprises an upwardly depending lip configured to deflect panniculus of an obese woman away from the surgical site during use.

9. A surgical access system according to claim 1, in which the radially adjustable retractor comprises an upper panel, a lower panel and a rear panel configured to cup a section of tissue, and in which the rear panel has a convex curvature to match the curvature of an opened incision.

10. A surgical access system according to claim 1, in which the radially adjustable retractor comprises an upper panel, a lower panel and a rear panel configured to cup a section of tissue, and in which the lower panel has a curved profile to match the curvature of an underside of the abdominal wall of the woman.

11. A surgical access system according to claim 1, in which the radially adjustable retractor is sufficiently resiliently deformable so as to allow a user to cup and clasp tissue when held in the hand.

12. A surgical access system according to claim 1, including a circumferentially adjustable saddle-shaped retractor configured to cup and manually retract a section of abdominal tissue at the incision, wherein the first coupling element is configured for retrofitting the circumferentially adjustable saddle-shaped retractor to the supporting ring in a tissue-retracting position.

13. A surgical access system according to claim 1, comprising a circumferentially adjustable saddle-shaped retractor including an integral second coupling element configured for direct engagement with the supporting ring at a plurality of different circumferential positions along the ring.

14. A surgical access system according to claim 1, comprising a circumferentially adjustable saddle-shaped retractor comprising a plurality of integral second coupling elements that are radially spaced apart to allow radial adjustment of the retractor on the ring.

15. A surgical access system according to claim 1, in which the supporting ring and the radially adjustable retractor are formed from polymer and are disposable.

16. A surgical access system according to claim 1, including a panniculus deflection element configured for retrofitting to the supporting ring and comprising an elongated curved panel and connection elements for connecting the panel to the supporting ring in a panniculus deflection orientation in which the elongated curved panel curves around an outer periphery of at least part of the supporting ring and projects upwardly relative to a plane of the supporting ring to deflect panniculus of the patient away from the surgical site.

17. A surgical access system as claimed in claim 16, in which the connection elements comprise a plurality of radial arms configured for snap-fit engagement with the supporting ring.

18. A surgical access system according to claim 16, in which the panniculus deflection element is formed from a transparent material.

19. A surgical access system according to claim 1, in which the radially adjustable retractor comprises an upper panel, a lower panel and a rear panel configured to cup a section of tissue, and in which the lower panel has a curved profile comprising one or more inflection curves to match a curvature of an underside of the abdominal wall of the woman, wherein the one or more inflection curves join the rear panel with the upper and lower panel, and wherein an external surface of the radially adjustable retractor comprising the inflection curves has a smooth or hydrophilic surface.

20. A surgical access system according to claim 1, in which the radially adjustable retractor comprises an upper panel, a lower panel and a rear panel configured to cup a section of tissue, and in which the lower panel has a curved profile to match the curvature of an underside of the abdominal wall of the woman, and in which one or more edges of the rear panel and/or the lower panel comprises a soft and flexible beading which is optionally formed from a soft elastomer or silicone material.

\* \* \* \* \*